United States Patent
Ando et al.

(10) Patent No.: US 10,747,022 B2
(45) Date of Patent: Aug. 18, 2020

(54) DIFFRACTIVE MULTI-FOCAL LENS AND METHOD FOR MANUFACTURING DIFFRACTIVE MULTI-FOCAL LENS

(71) Applicant: MENICON CO., LTD., Nagoya-shi, Aichi (JP)

(72) Inventors: Ichiro Ando, Kasugai (JP); Atsushi Kobayashi, Kasugai (JP)

(73) Assignee: MENICON CO., LTD., Nagoya (JP)

( * ) Notice: Subject to any disclaimer, the term of this patent is extended or adjusted under 35 U.S.C. 154(b) by 675 days.

(21) Appl. No.: 15/500,688

(22) PCT Filed: Aug. 8, 2014

(86) PCT No.: PCT/JP2014/071113
§ 371 (c)(1),
(2) Date: Jan. 31, 2017

(87) PCT Pub. No.: WO2016/021075
PCT Pub. Date: Feb. 11, 2016

(65) Prior Publication Data
US 2017/0227789 A1 Aug. 10, 2017

(51) Int. Cl.
*G02C 7/06* (2006.01)
*A61F 2/16* (2006.01)
(Continued)

(52) U.S. Cl.
CPC ............. *G02C 7/06* (2013.01); *A61F 2/1618* (2013.01); *A61F 2/1654* (2013.01); *A61L 2/16* (2013.01);
(Continued)

(58) Field of Classification Search
CPC .......... G02C 7/02; G02C 7/028; G02C 7/101; G02C 7/04; G02C 7/061; G02C 7/083;
(Continued)

(56) References Cited

U.S. PATENT DOCUMENTS

| 4,936,666 A | 6/1990 | Futhey |
| 5,117,306 A | 5/1992 | Cohen |

(Continued)

FOREIGN PATENT DOCUMENTS

| EP | 2013-118499 | * 8/2013 | ............ G02C 7/049 |
| JP | H03-35502 U | 4/1991 | |

(Continued)

OTHER PUBLICATIONS

Feb. 14, 2017 English Translation of International Preliminary Report on Patentability issued in Patent Application No. PCT/JP2014/071113.

(Continued)

*Primary Examiner* — Bumsuk Won
*Assistant Examiner* — Grant A Gagnon
(74) *Attorney, Agent, or Firm* — Oliff PLC

(57) ABSTRACT

A diffractive multi-focal lens having a diffractive structure comprising a plurality of concentric circular zones, wherein: at least a portion of the diffractive structure is provided with an overlapping region in which at least two zone profiles overlap in the same region; in the overlapping region, at least a portion of a first zone profile has a zone pitch represented by a prescribed equation, and at least a portion of a second zone profile has a zone pitch represented by another prescribed equation; and an addition power $P_1$ given by the first zone profile and an addition power $P_2$ given by the second zone profile are determined by a prescribed relational expression, in which a and b are mutually different real numbers, and a value of a/b cannot be expressed by a natural number X or by 1/X.

28 Claims, 30 Drawing Sheets

(51) Int. Cl.
  *G02C 7/04* (2006.01)
  *A61L 2/16* (2006.01)
  *G02B 5/18* (2006.01)
  *A61L 27/00* (2006.01)

(52) U.S. Cl.
  CPC ............... *A61L 27/00* (2013.01); *G02B 5/18* (2013.01); *G02C 7/042* (2013.01); *G02C 7/044* (2013.01); *G02C 2202/20* (2013.01)

(58) Field of Classification Search
  CPC ............ G02C 2202/20; G02C 2202/18; G02C 7/027; G02C 2202/16; G02C 2202/22; G02C 7/12; G02C 7/022; G02C 7/024; G02C 7/044; G02C 7/102; G02C 7/041; G02C 7/06; G02C 13/005; G02C 1/02; G02C 7/042; G02C 7/068; G02C 7/088; G02C 13/001; G02C 13/003; G02C 1/023; G02C 1/10; G02C 2202/10; G02C 2202/24; G02C 5/00; G02C 7/025; G02C 7/047; G02C 7/049; G02C 7/063; G02C 7/066; G02C 7/085; G02C 7/086; G02C 7/10; G02C 7/104; G02C 7/105; G02C 11/02; G02C 11/12; G02C 1/00; G02C 1/04; G02C 1/06; G02C 1/08; G02C 2200/02; G02C 2200/08; G02C 2202/02; G02C 2202/04; G02C 2202/08; G02C 2202/12; G02C 5/02; G02C 7/046; G02C 7/048; G02C 7/08; G02C 7/108; G02C 7/14; G02C 7/16; G02B 1/041; G02B 1/105; G02B 1/14; G02B 1/18; G02B 27/0006; G02B 1/115; G02B 27/0172; G02B 3/12; G02B 1/16; G02B 2027/011; G02B 2027/0178; G02B 27/0075; G02B 27/4211; G02B 3/02; G02B 3/04; G02B 3/08; G02B 3/14; G02B 5/208; G02B 13/146; G02B 17/08; G02B 1/06; G02B 1/10; G02B 1/11; G02B 1/113; G02B 1/116; G02B 1/12; G02B 2027/0123; G02B 25/001; G02B 25/004; G02B 26/004; G02B 26/06; G02B 27/0018; G02B 27/0025; G02B 27/0037; G02B 27/2228; G02B 3/00; G02B 3/0062; G02B 3/0081; G02B 3/0087; G02B 5/00; G02B 5/1866; G02B 5/1876; G02B 5/188; G02B 5/1885; G02B 5/1895; G02B 5/286; G02B 5/3025; G02B 5/3033; G02B 6/10; A61F 2/1618; A61F 2/16; A61F 2/1613; A61F 2/1637; A61F 2/164; A61F 2/1654; A61F 2230/0006; A61F 2/1645; A61F 2002/1699; A61F 2/1451; A61F 2/1616; A61F 2/1624; A61F 2/1632; A61F 2/1648; A61F 9/045
  USPC ........................................................ 351/159
  See application file for complete search history.

(56) References Cited

U.S. PATENT DOCUMENTS

| | | |
|---|---|---|
| 6,829,093 B1 | 12/2004 | Nakai |
| 2007/0258143 A1 | 11/2007 | Portney |
| 2011/0270390 A1 | 11/2011 | Kobayashi et al. |
| 2012/0140166 A1 | 6/2012 | Zhao |
| 2012/0170122 A1 | 7/2012 | Hayashi et al. |
| 2012/0224138 A1 | 9/2012 | Cohen |
| 2014/0347624 A1 | 11/2014 | Ando et al. |
| 2015/0022775 A1 | 1/2015 | Ando et al. |

FOREIGN PATENT DOCUMENTS

| | | |
|---|---|---|
| JP | H03-278002 A | 12/1991 |
| JP | H05-297209 A | 11/1993 |
| JP | 2001-042112 A | 2/2001 |
| JP | 2006-139129 A | 6/2006 |
| JP | 2010-158315 A | 7/2010 |
| JP | 2013-517822 A | 5/2013 |
| JP | 2013-168195 A | 8/2013 |
| WO | 2010/079528 A1 | 7/2010 |
| WO | 2013-118176 A1 | 8/2013 |
| WO | 2013/118499 A1 | 8/2013 |
| WO | 2013/122175 A1 | 8/2013 |

OTHER PUBLICATIONS

Apr. 11, 2018 Partial Supplementary European Search Report issued in Patent Application No. 14899300.9.
Feb. 27, 2018 Office Action issued in Japan Patent Application No. 2016-508883.
Jul. 25, 2018 Search Report issued in European Patent Application No. 14899300.9.
Albero, Jorge et al. "Generalized diffractive optical elements with asymmetric harmonic response and phase control". Applied Optics, vol. 52, No. 15, 3637-3644, 2013.
Oct. 14, 2014 International Search Report issued in Patent Application No. PCT/JP2014/071113.

* cited by examiner

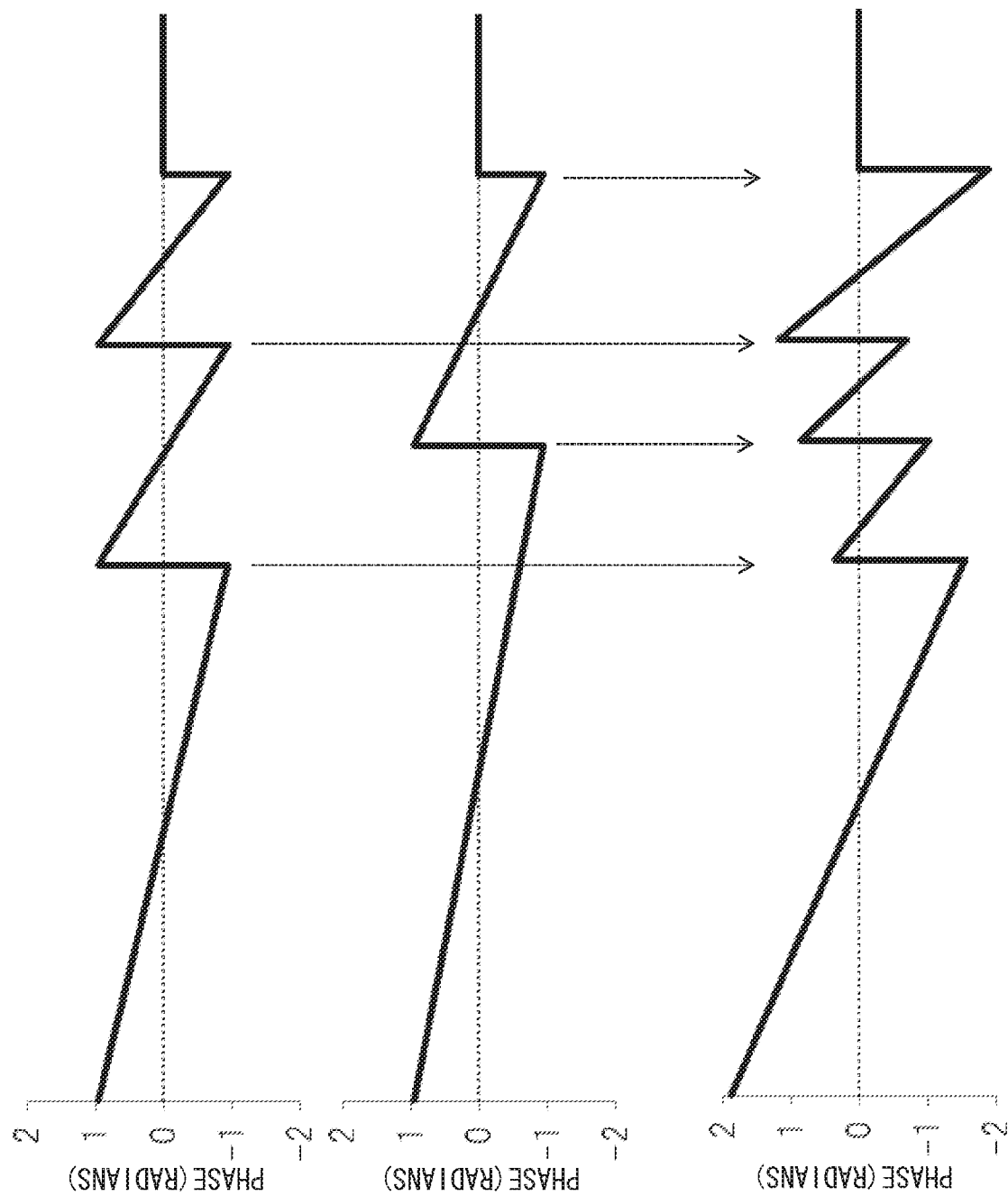

[COMPARATIVE EXAMPLE 1]

[COMPARATIVE EXAMPLE 2]
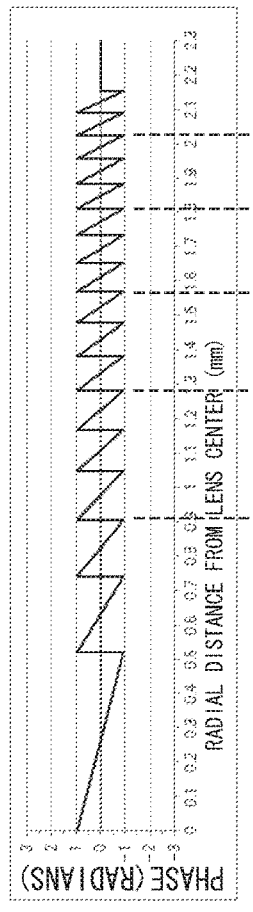
FIG.5A FIRST ZONE PROFILE
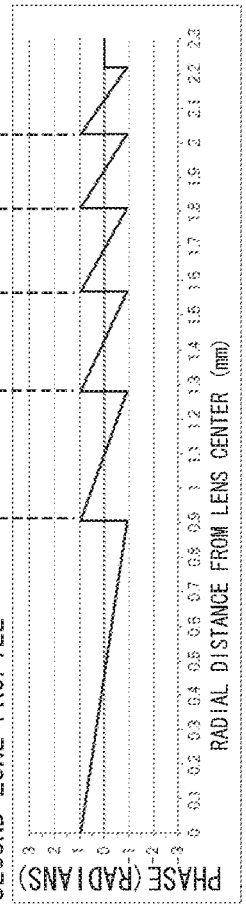
FIG.5B SECOND ZONE PROFILE
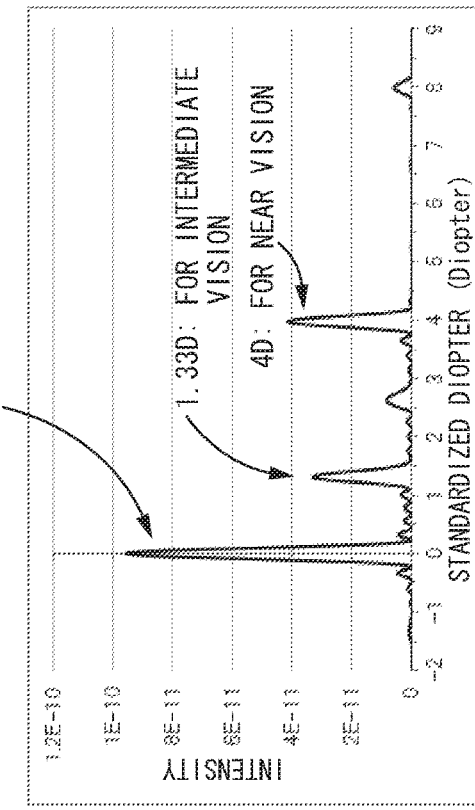
FIG.5D
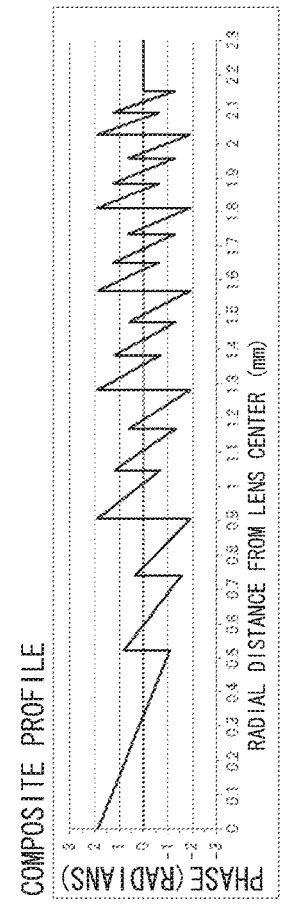
FIG.5C COMPOSITE PROFILE

[EXAMPLE 1]
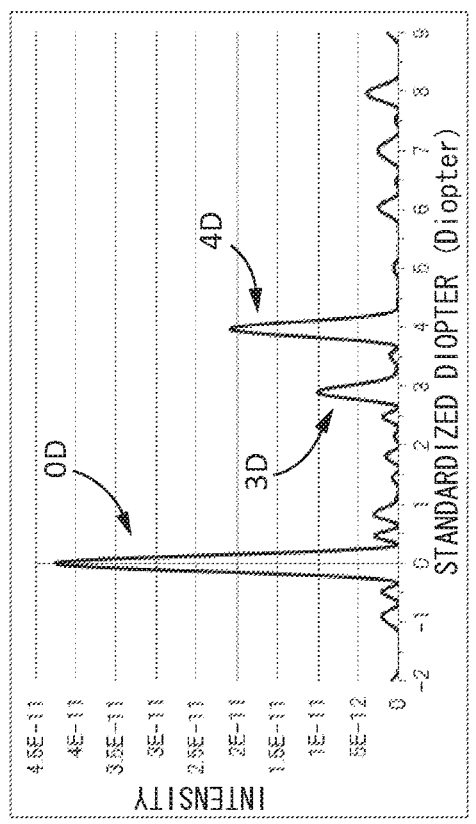
FIG.6A PROFILE(1)
FIG.6B PROFILE(2)
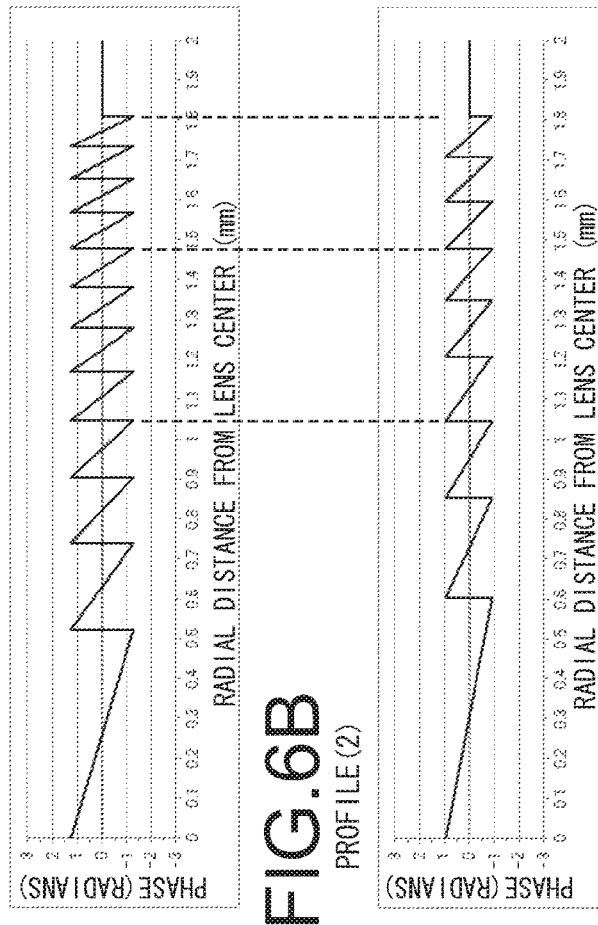
FIG.6C COMPOSITE PROFILE
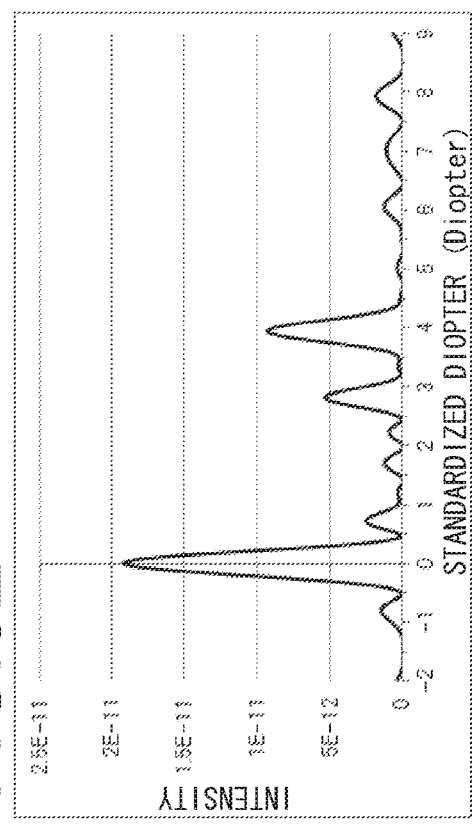
FIG.6D 1ST TO 18TH ZONE
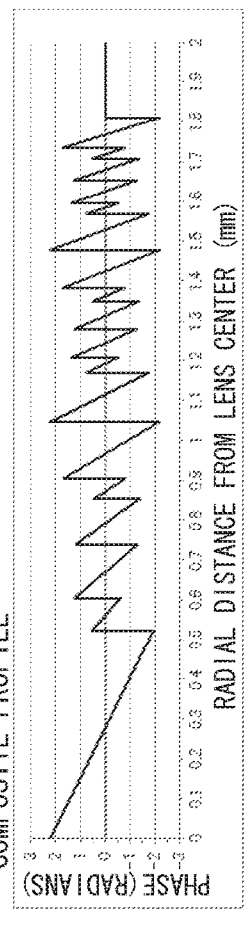
FIG.6E 1ST TO 12TH ZONE

[EXAMPLE 2]

PROFILE(1)

PROFILE(2)

COMPOSITE PROFILE

[EXAMPLE 3]

PROFILE(1)

PROFILE(2)

COMPOSITE PROFILE

[EXAMPLE 4]

PROFILE (1)

PROFILE (2)

COMPOSITE PROFILE

[EXAMPLE 5]
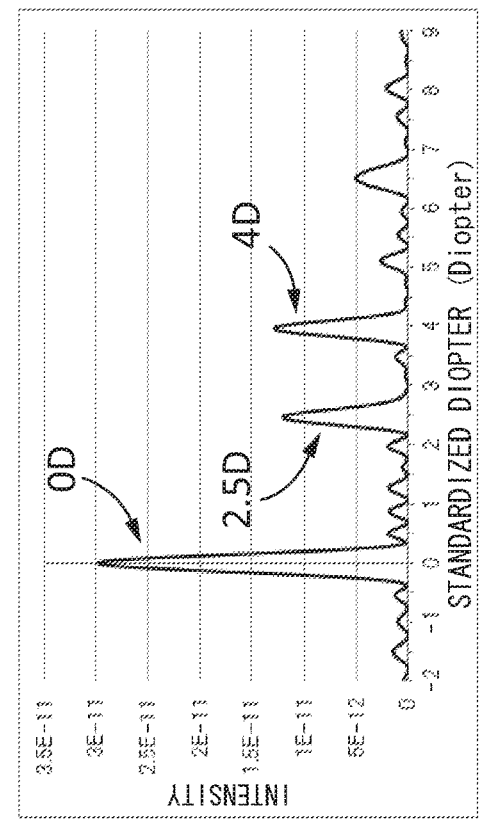
FIG.10A PROFILE(1)
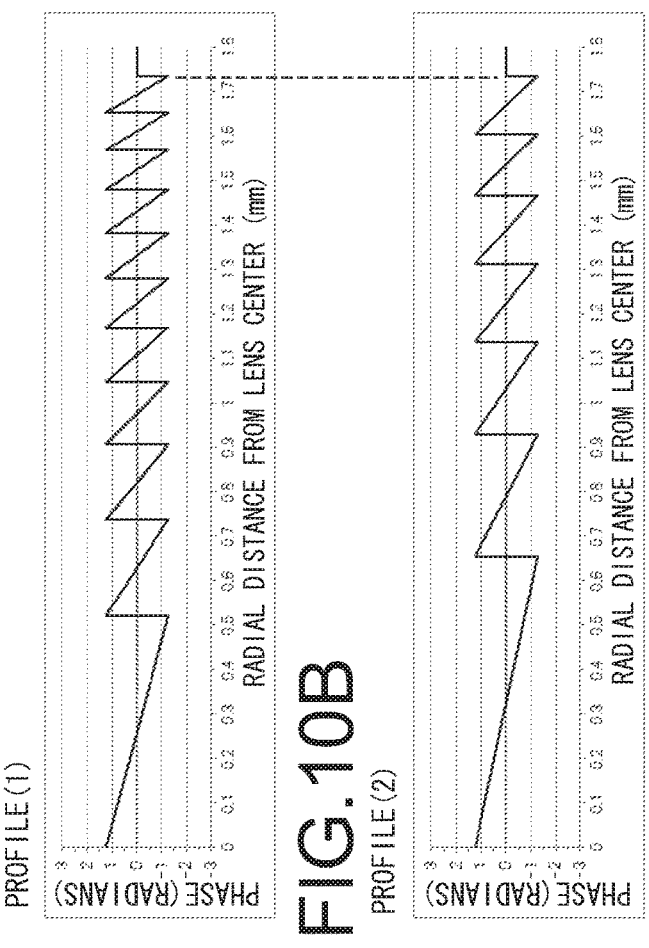
FIG.10B PROFILE(2)
FIG.10C COMPOSITE PROFILE
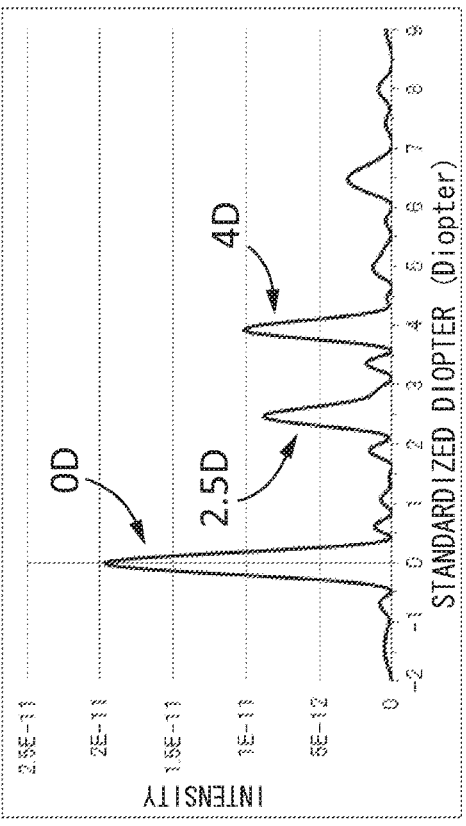
FIG.10D 1ST TO 17TH ZONE
FIG.10E 1ST TO 14TH ZONE

[EXAMPLE 6]

PROFILE(1)

PROFILE(2)

COMPOSITE PROFILE

[EXAMPLE 7]

PROFILE (1)

PROFILE (2)

COMPOSITE PROFILE

[EXAMPLE 8]

[EXAMPLE 9]
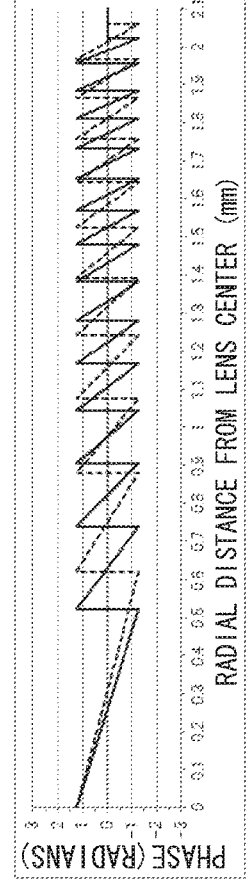
FIG.14A PROFILE(1) SOLID LINE PROFILE(2) DASHED LINE
FIG.14B COMPOSITE PROFILE
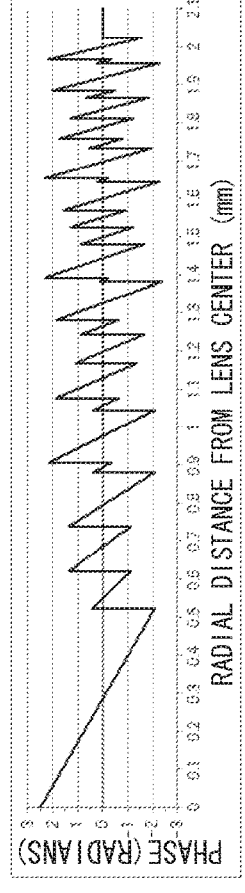
FIG.14C

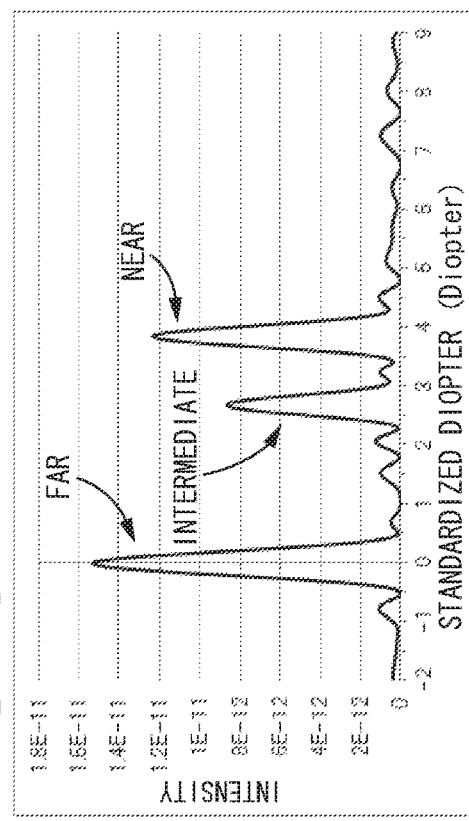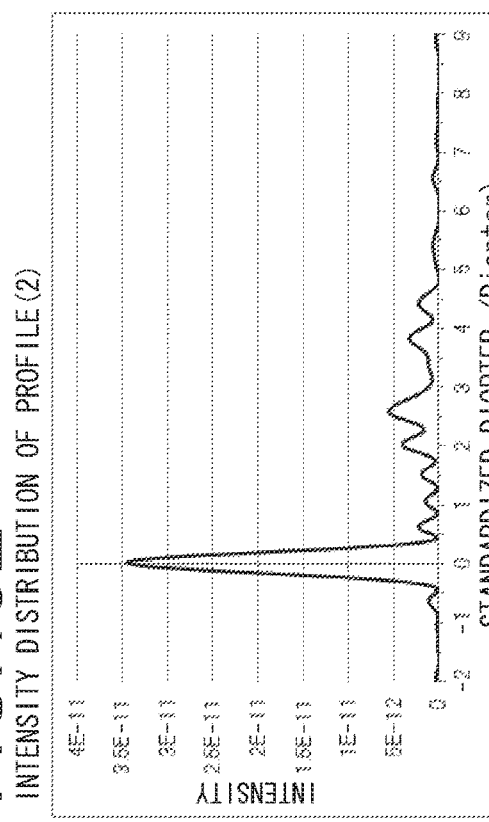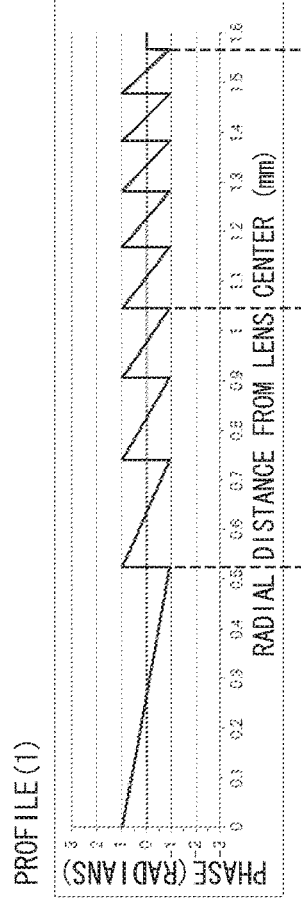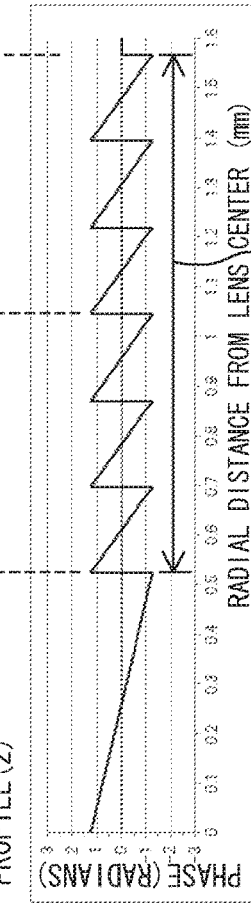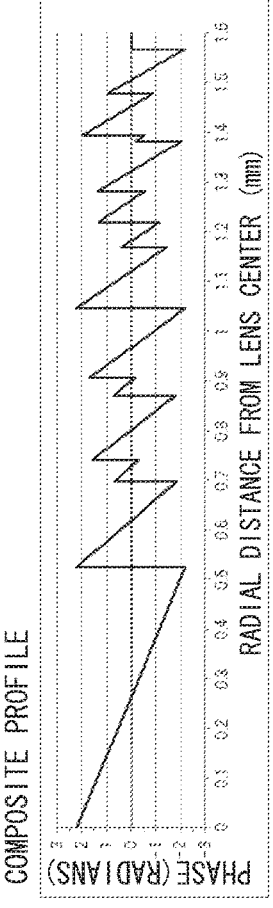

[EXAMPLE 11]

PROFILE(1)

PROFILE(2)

COMPOSITE PROFILE

[EXAMPLE 12]

PROFILE (1)

PROFILE (2)

PARTIAL COMPOSITE PROFILE   PROFILE(1)   COMPOSITE PROFILE

[EXAMPLE 13]

PROFILE (1)

PROFILE (2)

PARTIAL COMPOSITE PROFILE    PROFILE (1) COMPOSITE PROFILE

[EXAMPLE 14]
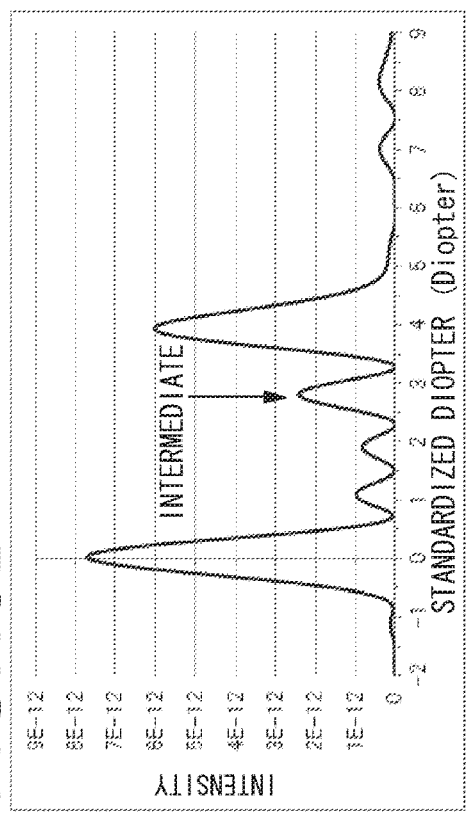
FIG. 19A PROFILE (1)
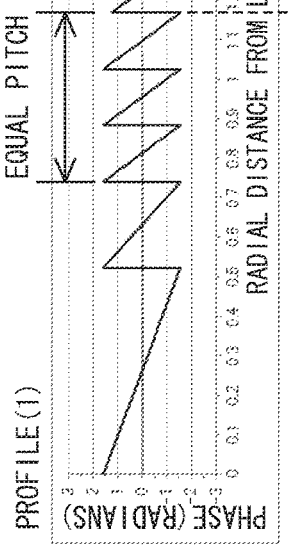
FIG. 19B PROFILE (2)
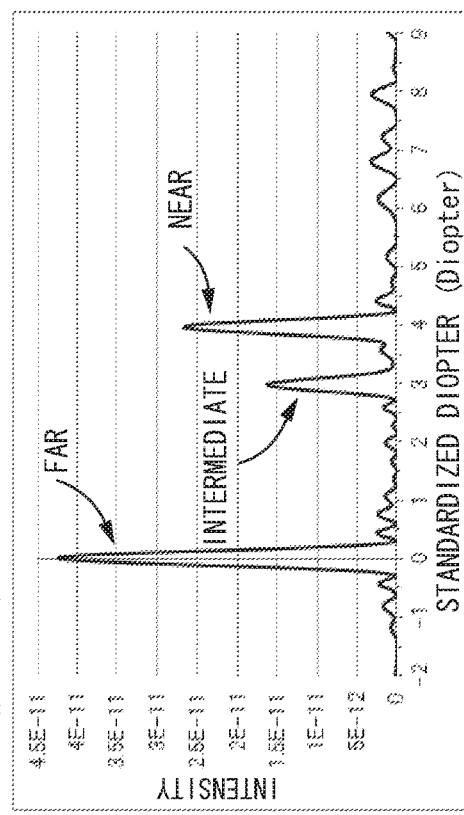
FIG. 19D
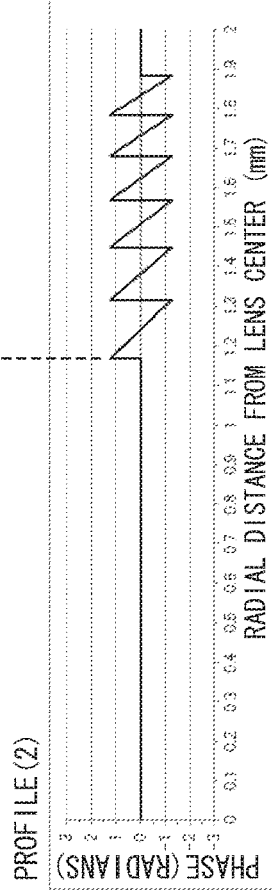
FIG. 19C PARTIAL COMPOSITE PROFILE
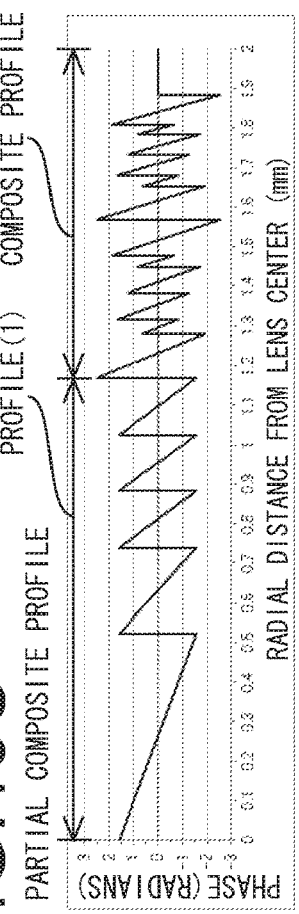
FIG. 19E

[EXAMPLE 15]

PROFILE(1)

PROFILE(2)

COMPOSITE PROFILE

[EXAMPLE 16]
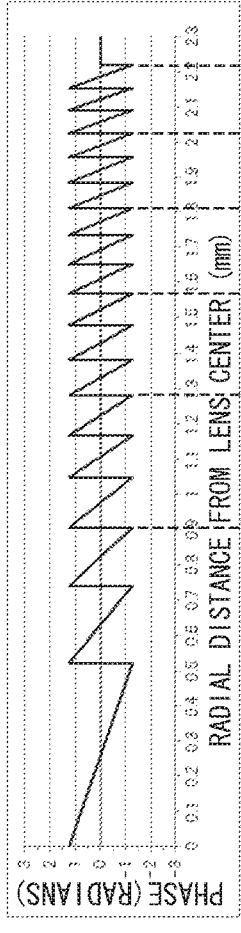
FIG.21A PROFILE (1)
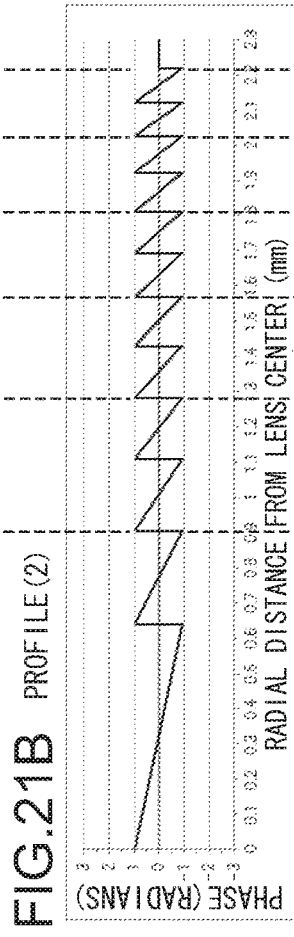
FIG.21B PROFILE (2)
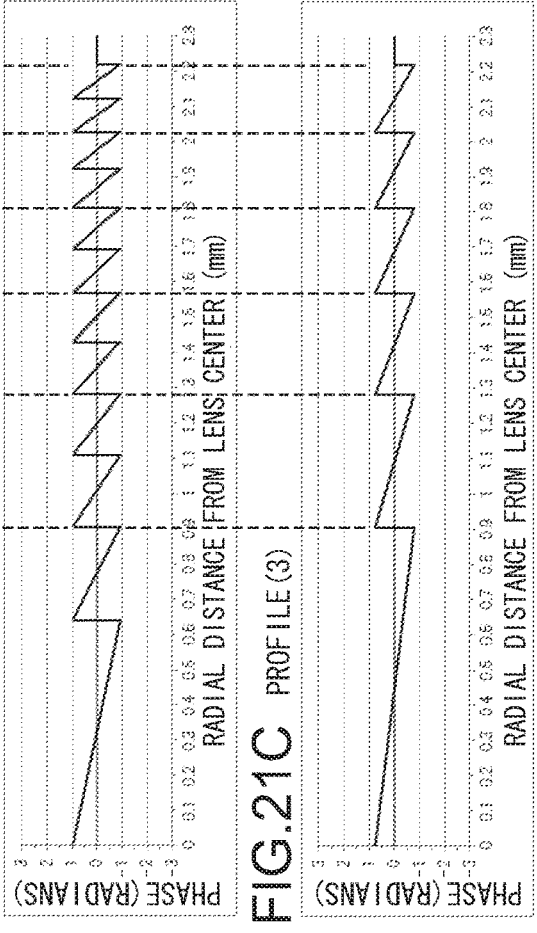
FIG.21C PROFILE (3)
FIG.21D COMPOSITE PROFILE
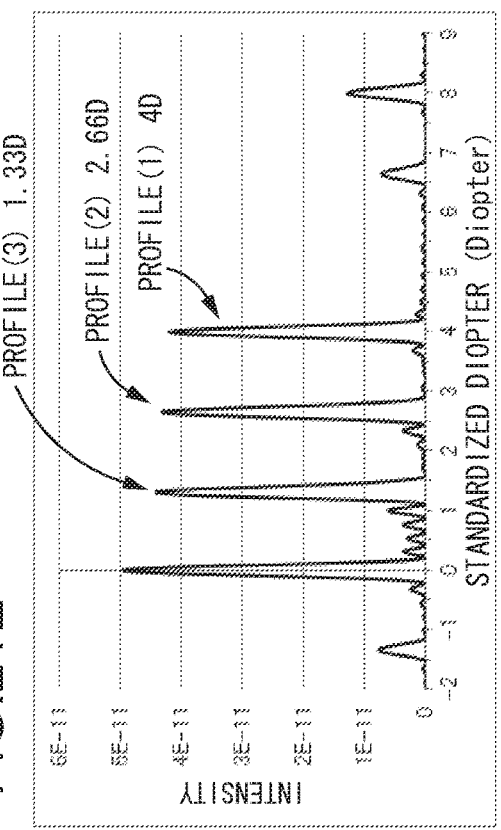
FIG.21E
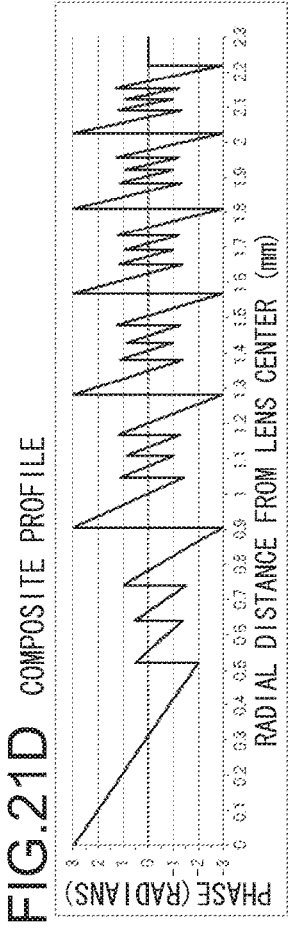

[EXAMPLE 17]
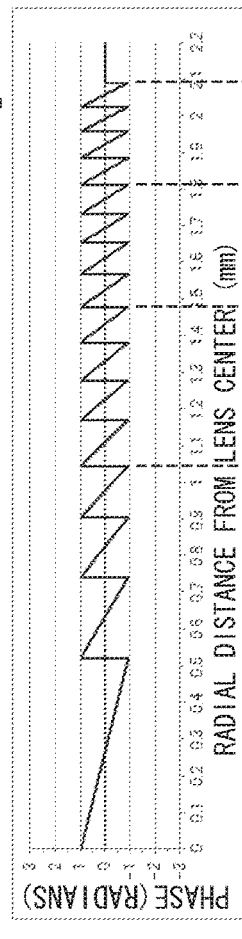
FIG.22A PROFILE (1)
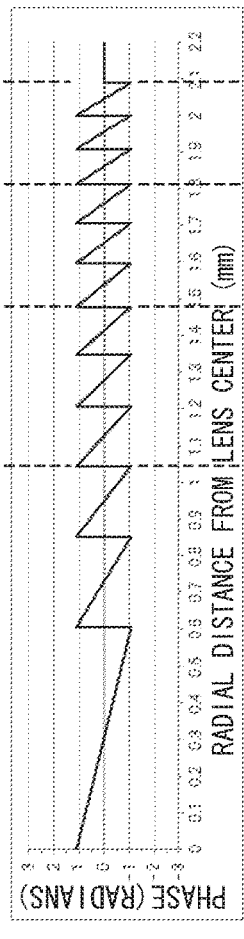
FIG.22B PROFILE (2)
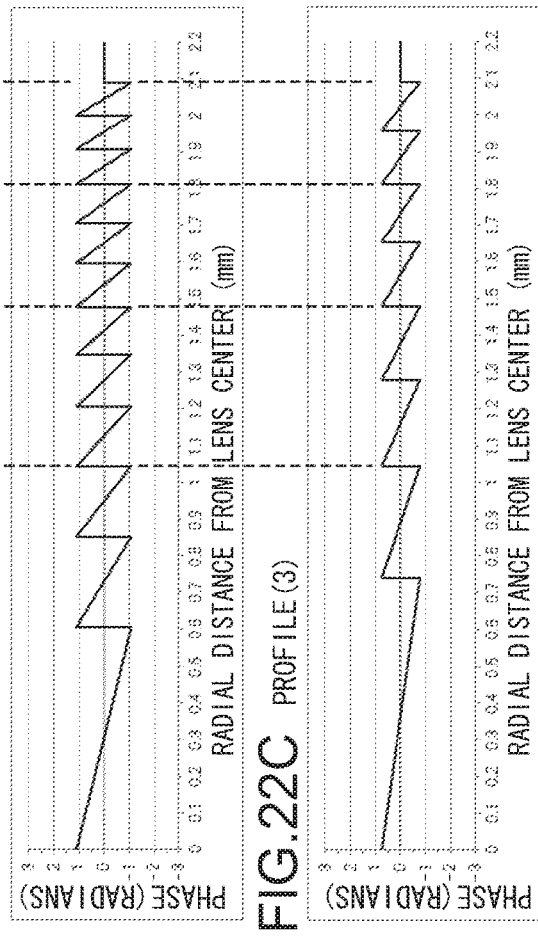
FIG.22C PROFILE (3)
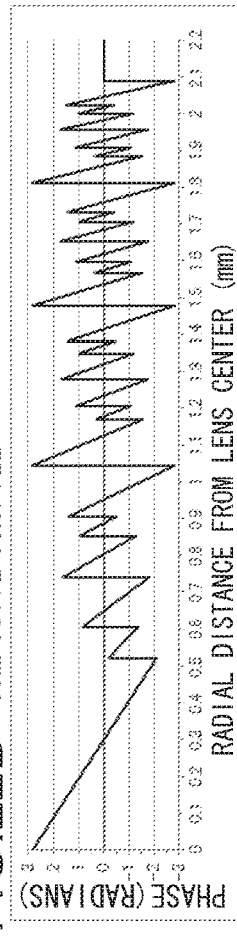
FIG.22D COMPOSITE PROFILE
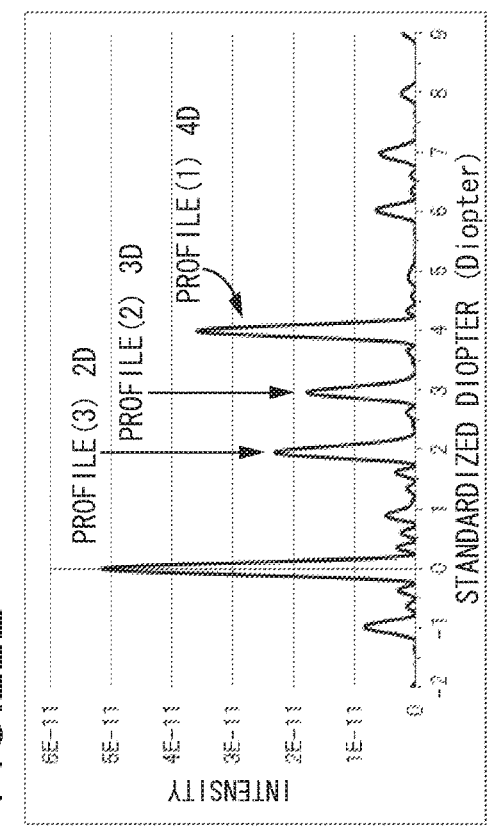
FIG.22E

[EXAMPLE 18]
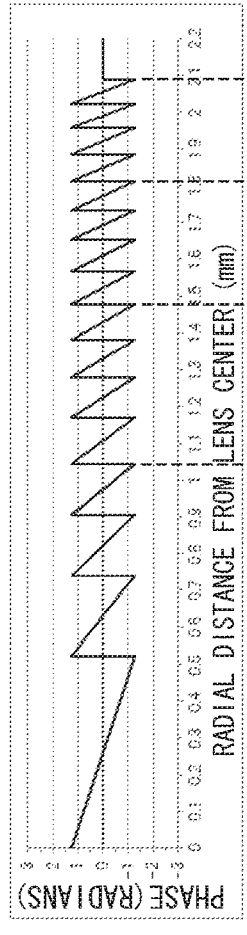
FIG.23A PROFILE(1)
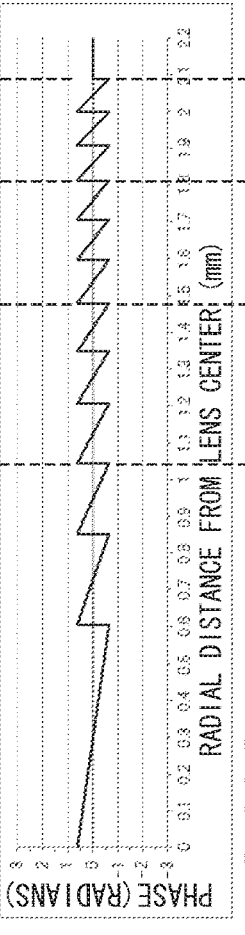
FIG.23B PROFILE(2)
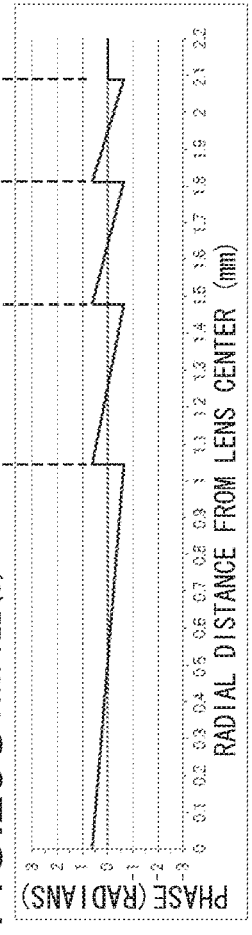
FIG.23C PROFILE(3)
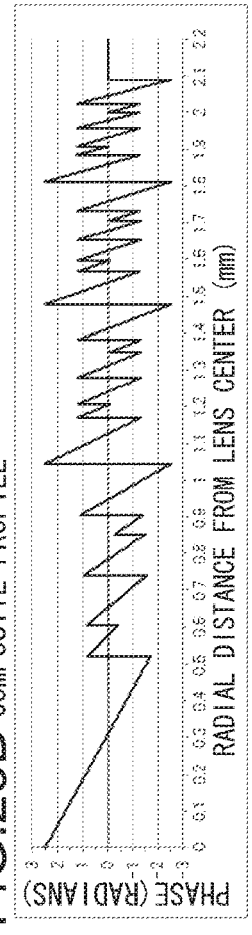
FIG.23D COMPOSITE PROFILE
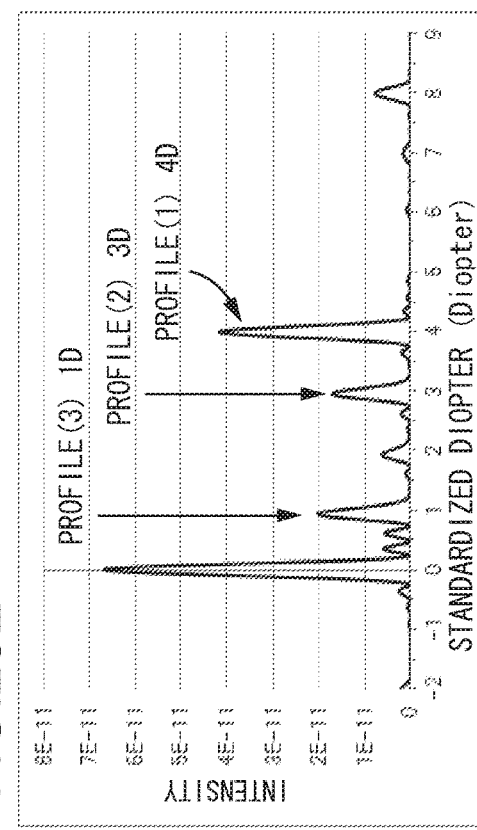
FIG.23E

[EXAMPLE 19]
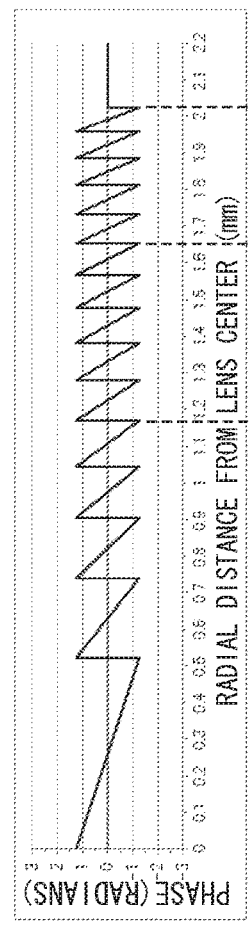
FIG.24A PROFILE (1)
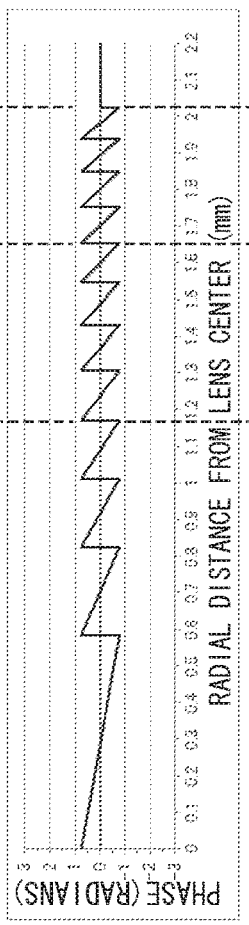
FIG.24B PROFILE (2)
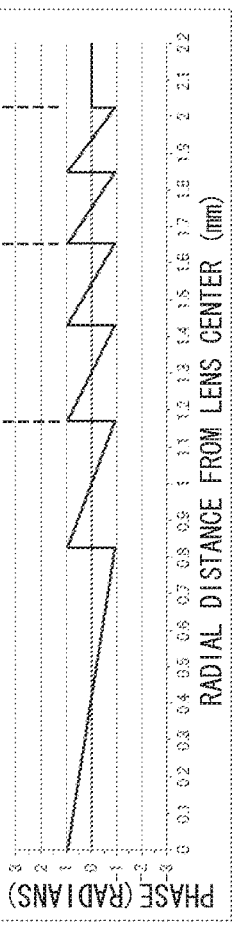
FIG.24C PROFILE (3)
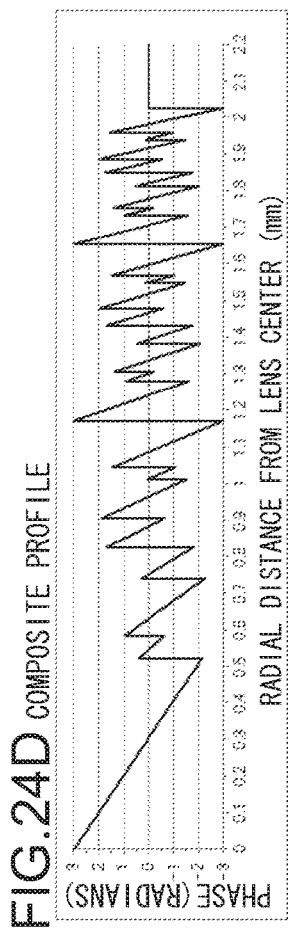
FIG.24D COMPOSITE PROFILE
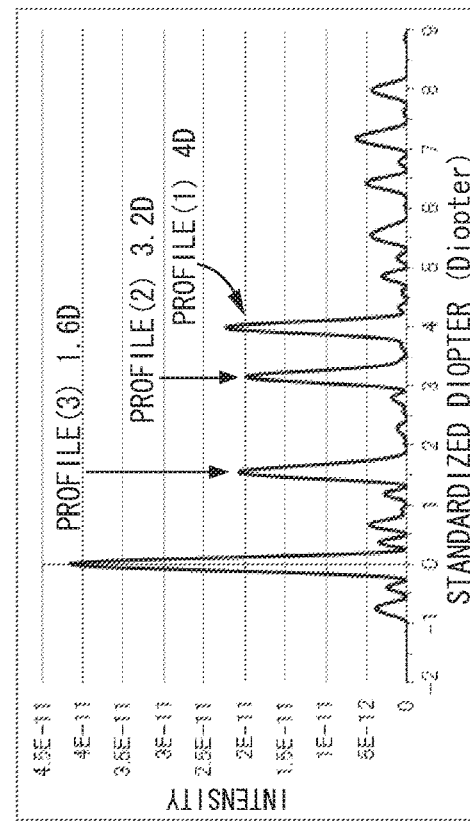
FIG.24E

[EXAMPLE 20]
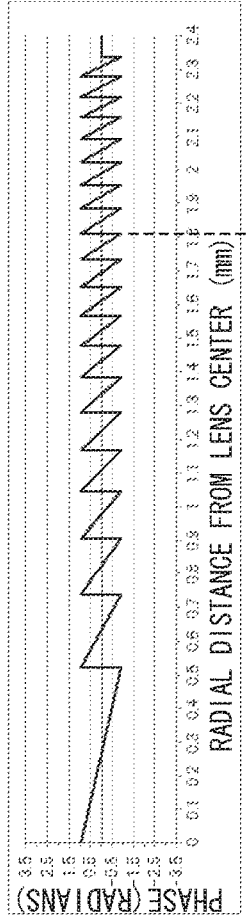
FIG.25A PROFILE(1)
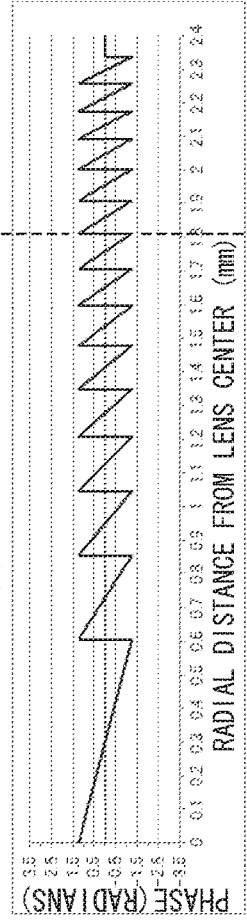
FIG.25B PROFILE(2)
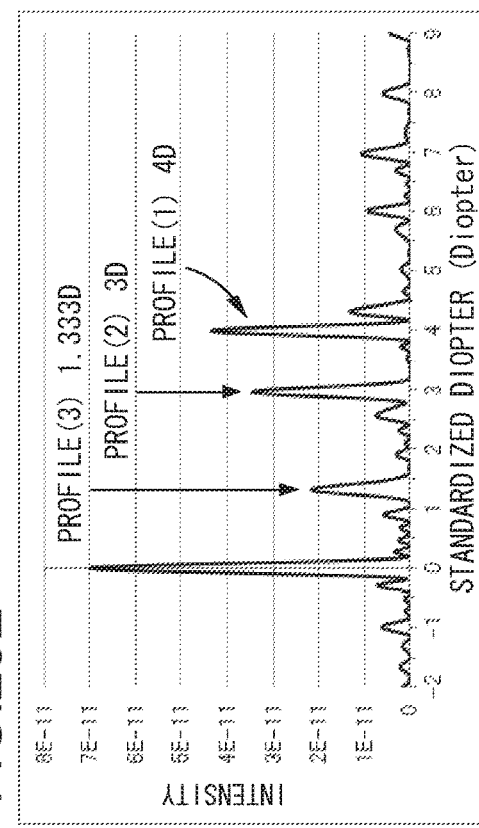
FIG.25E
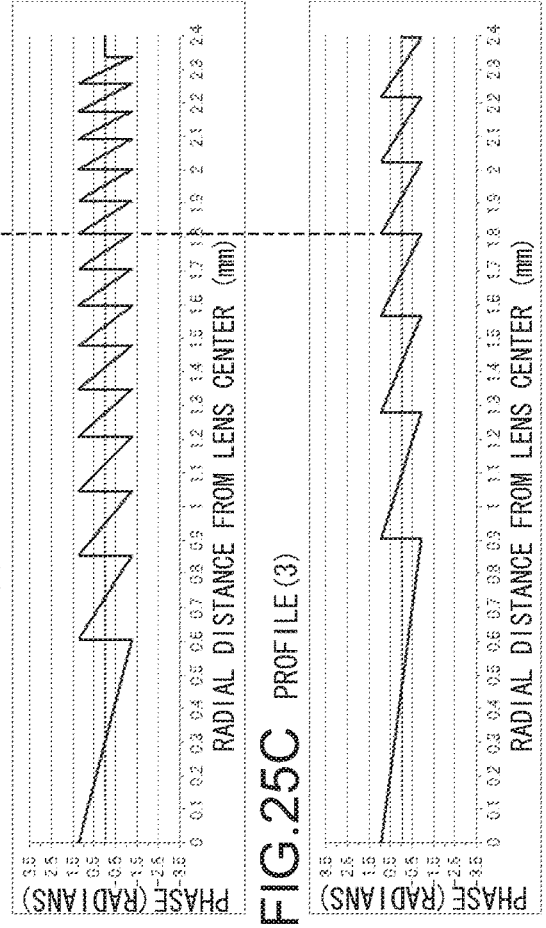
FIG.25C PROFILE(3)
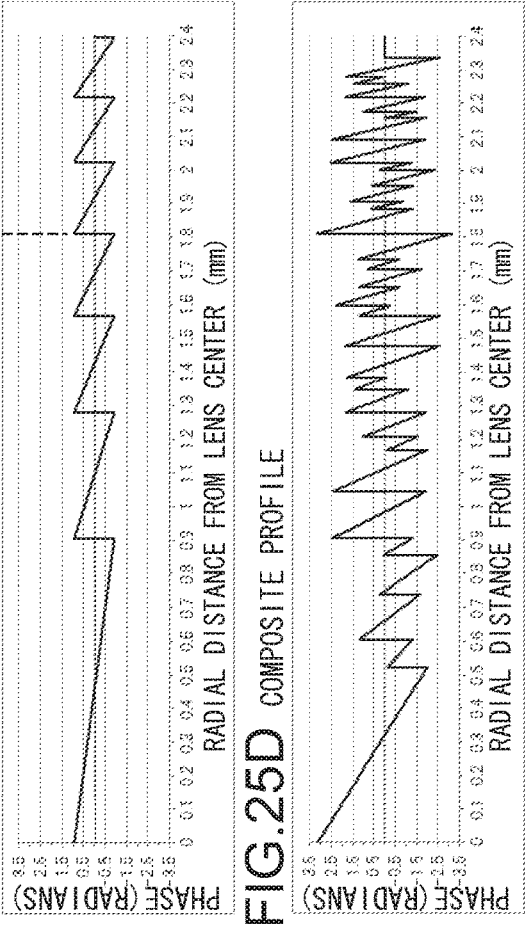
FIG.25D COMPOSITE PROFILE

[EXAMPLE 21]
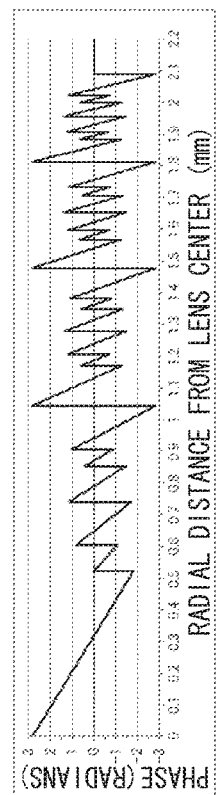
FIG.26E COMPOSITE PROFILE
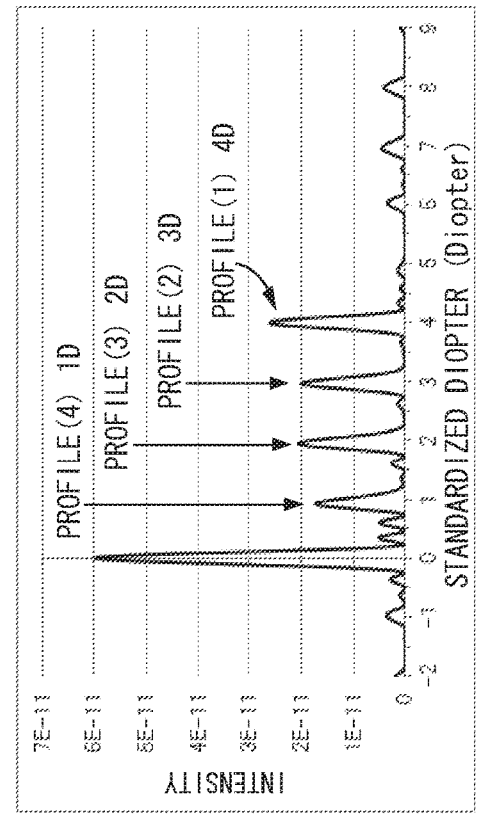
FIG.26F
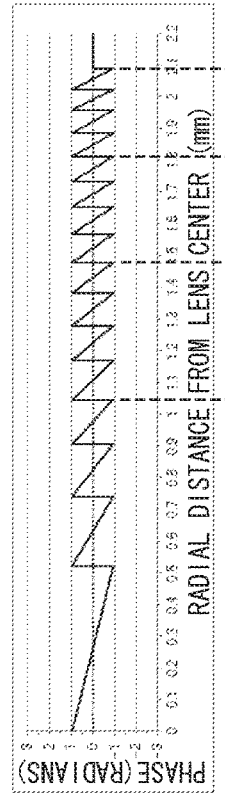
FIG.26A PROFILE (1)
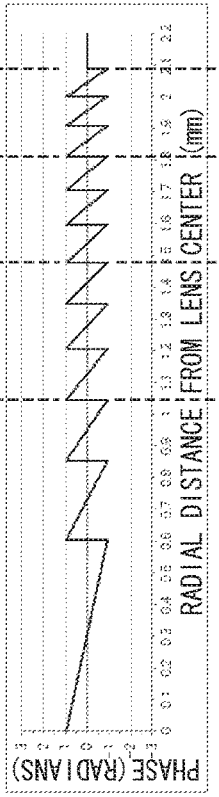
FIG.26B PROFILE (2)
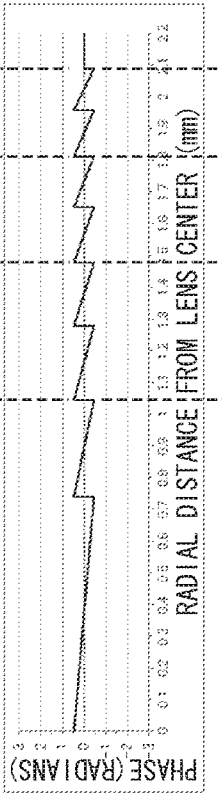
FIG.26C PROFILE (3)
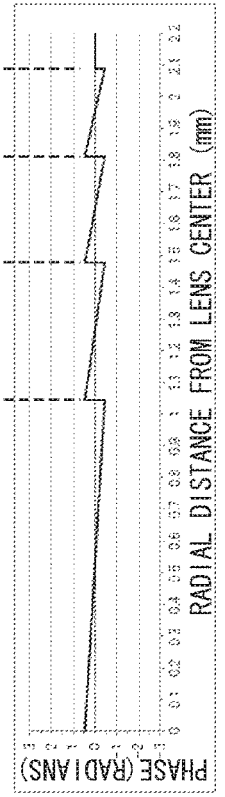
FIG.26D PROFILE (4)

[EXAMPLE 22]
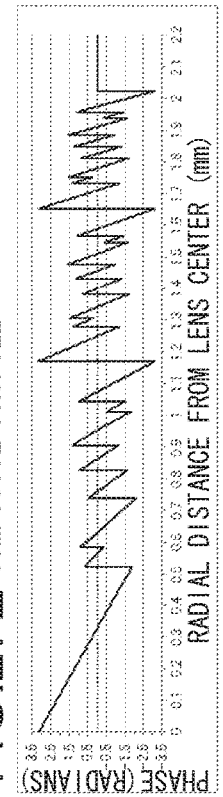
FIG.27E COMPOSITE PROFILE
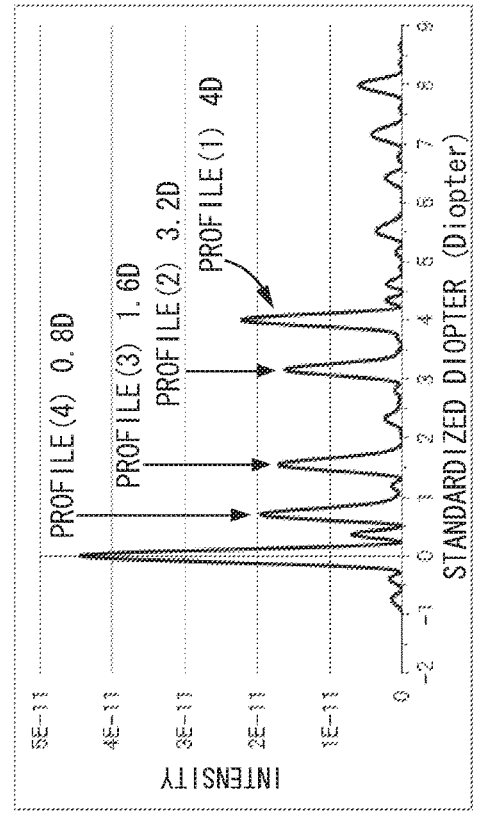
FIG.27F
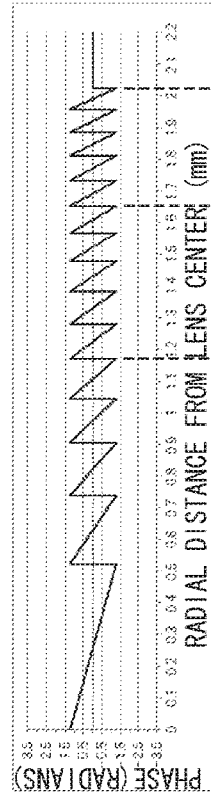
FIG.27A PROFILE(1)
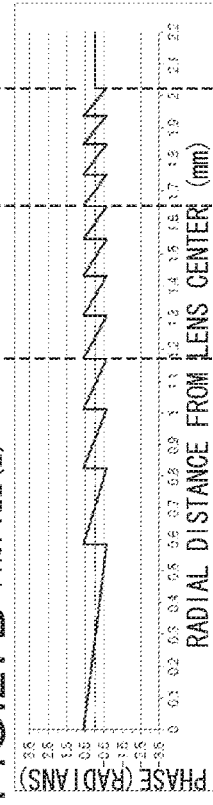
FIG.27B PROFILE(2)
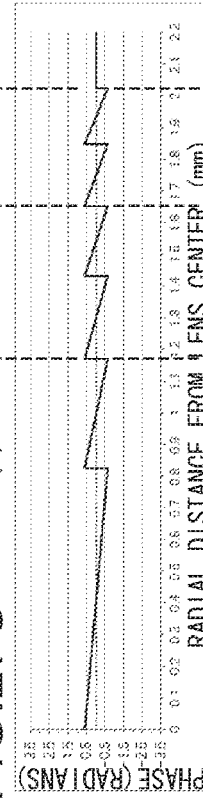
FIG.27C PROFILE(3)
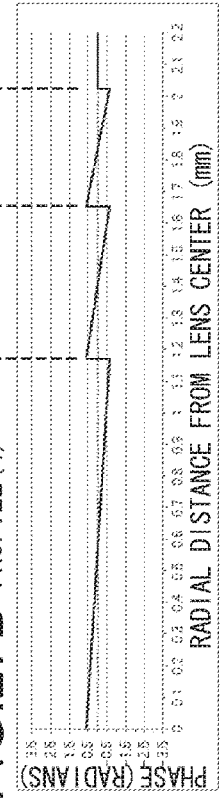
FIG.27D PROFILE(4)

[EXAMPLE 23]
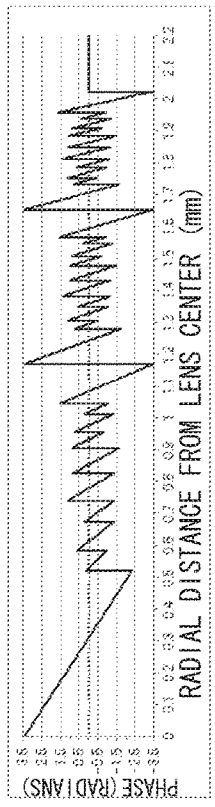
FIG.28F COMPOSITE PROFILE
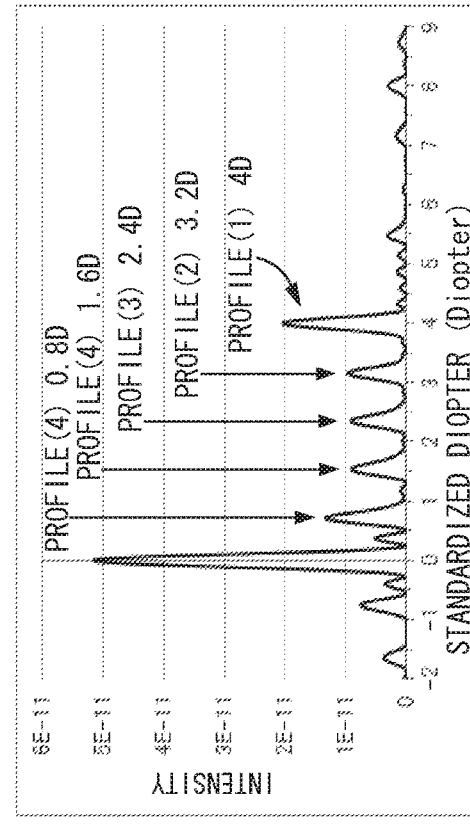
FIG.28G
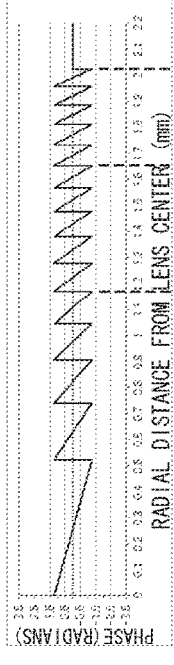
FIG.28A PROFILE(1)
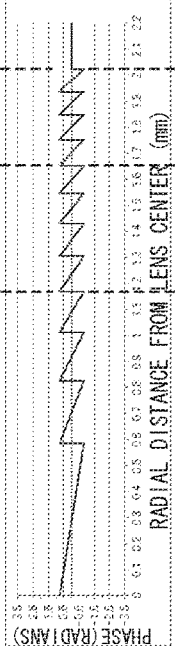
FIG.28B PROFILE(2)
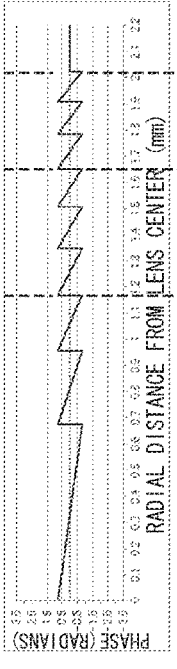
FIG.28C PROFILE(3)
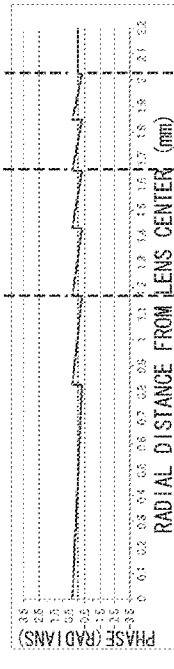
FIG.28D PROFILE(4)
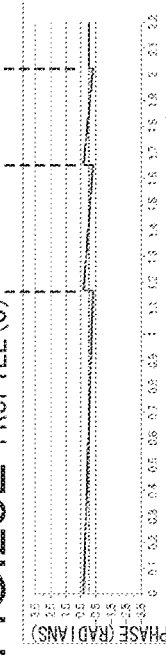
FIG.28E PROFILE(5)

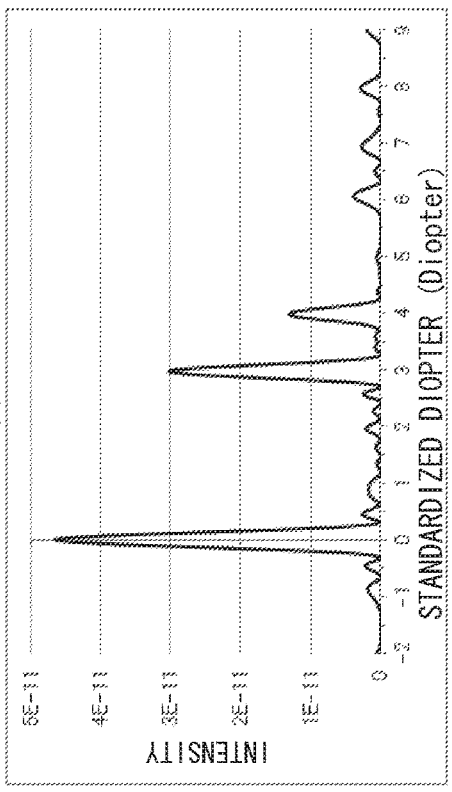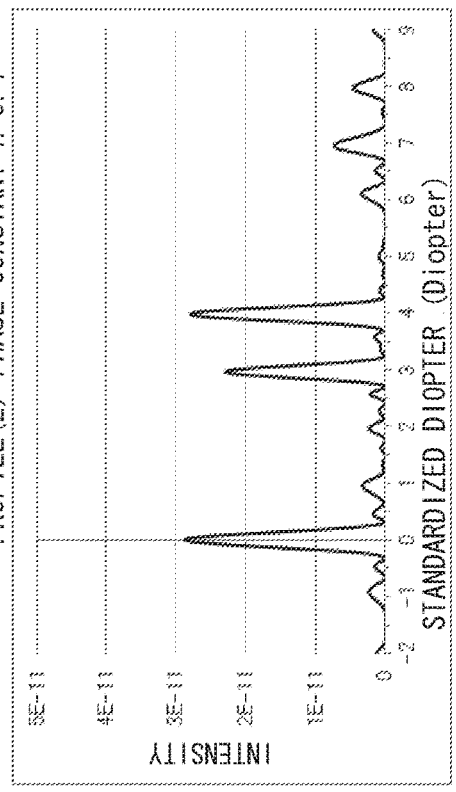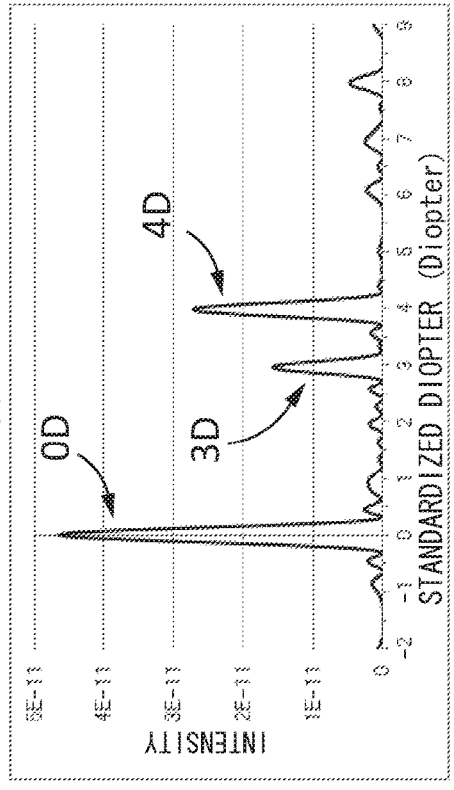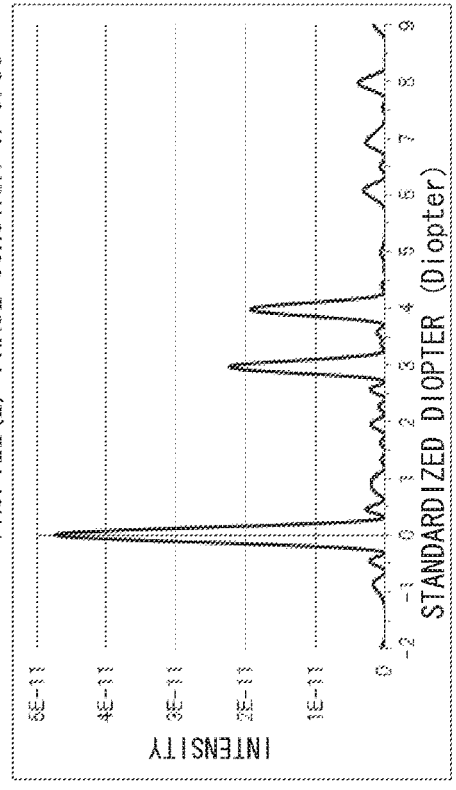

DIFFRACTIVE MULTI-FOCAL LENS AND METHOD FOR MANUFACTURING DIFFRACTIVE MULTI-FOCAL LENS

TECHNICAL FIELD

The present invention relates to a diffractive multi-focal lens that generates at least three focal points using diffracted light, and a method for manufacturing a diffractive multi-focal lens.

BACKGROUND ART

Multi-focal type optical lenses having a plurality of focal points are known from the past, and have been applied to various optical systems such as the human eye optical system, camera optical systems, or the like. For example, with contact lenses used as corrective optical elements for refractive error, alternative optical elements after lens extraction or the like with the optical system of the human eye, or with intraocular lenses used for insertion in the human eye, by applying multi-focal lenses, it is possible to compensate for the decrease or loss of accommodation function of eye in the human body.

Particularly in recent years, there is an increase in people continuing to use contact lenses even when they reach the age of having presbyopia. People with presbyopia have a decrease in focus accommodation function, so a symptom appears of having difficulty focusing on nearby items. Thus, multi-focal contact lenses which can also focus on nearby items become necessary for presbyopia patients. Also, for patients who have undergone cataract surgery, the lens which is in charge of the adjustment function is removed, so even if an intraocular lens is inserted as a replacement, the symptom of difficulty seeing close up remains. A multi-focal function that offers a plurality of focal points is necessary for that intraocular lens as well. Thus, there is a great increase in the need for multi-focal lenses reflecting the aging society of recent years.

However, as a method for realizing this multi-focal lens, examples are known of a refraction type multi-focal lens for which a plurality of focal points are formed based on the principle of refraction, and of a diffractive type multi-focal lens for which a plurality of focal points are formed based on the principle of diffraction. With the latter diffractive type multi-focal lens, equipped are a plurality of diffractive structures formed in concentric circle formed on the optical part of the lens, and a plurality of focal points are given by the mutual interference effect of light waves that passed through the plurality of diffractive structures (zones). Thus, compared to the refraction type lens with which a focal point is given by the refraction effect of light waves at a refracting surface comprising boundary surfaces with different refractive indexes, with the diffractive type multi-focal lens, there are advantages such as being able to set a high lens power while inhibiting an increase in lens thickness.

Typically, the diffractive type multi-focal lens has a diffractive structure by which the diffractive zone pitch gradually becomes smaller as it goes from the lens center toward the periphery according to a rule called the Fresnel zone, and this has multiple focal points by using different orders of diffracted light generated from that structure. When using a diffractive multi-focal lens as a contact lens or an intraocular lens, normally, 0th order diffracted light is the focal point for far vision, and +1 order diffracted light is the focal point for near vision. By distribution of this diffracted light, it is possible to make a bifocal lens having focal points for far and near vision. The general Fresnel zone constitution is basically the zone pitches having the zone outer diameter radius determined by Equation 1 below. This Equation 1 is hereafter called a Fresnel zone setting equation.

$$r_n = \sqrt{\frac{nK}{P}} \quad \text{[Equation 1]}$$

$r_n$ is the outer diameter radius of the nth zone obtained from Equation 1. K is a constant. P is addition power for setting the focus point of first order diffracted light with the focus point of 0th order diffracted light as a reference, and by varying this, it is possible to change the focal point position of the first order diffracted light.

For example when the focal point by 0th order diffracted light is a focal point for far vision, and first order diffracted light is set as the focal point for near vision, when P (the addition power noted above) is made larger, the focal point position for near vision moves closer to the lens. Specifically, when using that lens for the human eye, items that are closer become visible. Conversely, when P is made smaller, the focal position for near vision recedes away from the lens. In this case, when the lens is used in the human eye, the near points that are visible recede away.

For patients with advanced presbyopia, or patients who have an intraocular lens inserted, power of accommodation of the crystalline lens decreases or is lost, so it is preferable to use a lens for which the focal point is matched in the nearer direction as with the former example. In other words, an item is needed for which the addition power is set to be large. On the other hand, for patients for which the power of accommodation has not decreased that much, even if the near focal point position is not made that near, it is possible to see near objects by joint use with one's own residual power of accommodation, so there are cases when large addition power does not need to be set. Taking into consideration the status of the eyes of these patients, it is possible to obtain bifocal lenses that can be suitably used at different required powers for each patient by setting P.

However, with this bifocal type lens, we found that the problems to be resolved noted below remain.

With bifocal lenses, there are two focal points existing together, the far focal point and near focal point, and between these points, there is a blank region in which no focal point exists. The larger the addition power is made, the more this blank region expands. For patients with decreased power of accommodation, a diffractive multi-focal lens having large addition power is suitable, but when using that lens, there is the problem that though both far and near objects are visible, when objects between those focal points are viewed, they cannot be seen clearly.

Power of accommodation decreases as age increases. The power of accommodation is typically defined using numerical values expressed in diopter units in the opthalmological field, and the larger the numerical value, the greater the power of accommodation. The residual power of accommodation differs for each person, but a typical trend is said to be for the residual power of accommodation to decrease to approximately 2 to 3 diopters in the mid forties, approximately 1.5 diopters in the fifties, and less than 1 diopter in the sixties. Hereafter, diopters are noted as D as the refractive power unit.

Normally, when viewing an object 30 cm in front of oneself, the power of accommodation of the human eye that is required is approximately 3.3 D, and for example when a person in his fifties views an object at that point, the power of accommodation is insufficient by approximately 1.8 to 2 D. When such a patient uses bifocal lenses, addition power of approximately 1.8 to 2 D is needed. Also, for patients with an intraocular lens inserted, the crystalline lens as been removed, so there is almost no residual power of accommodation. With such patients, addition power of 3 to 3.5 D is necessary. When setting the addition power for the lens with an intraocular lens as a multi-focal lens, it is necessary to further change the addition power given to the lens by the set position of the intraocular lens within the eye, and for eyes with an intraocular lens inserted, to give the addition power of 3 to 3.5 D noted above, it is necessary to give addition power of 3.5 to 4 D to the lens itself.

When a patient with advanced presbyopia or a patient with an intraocular lens inserted uses a bifocal lens set so as to have this addition power, there is a new problem of having it be difficult to see the intermediate region between the far and near range. A multi-focal lens is needed that is capable of generating a focal point in this blank region as well.

Considering these problems, even with the conventional diffractive multi-focal lens, items with a further increase in the number of focal points have been proposed. As specific examples, proposed previously by this patent applicant, there are Japanese Unexamined Patent Publication No. JP-A-2010-158315 (Patent Document 1) and PCT Japanese Translation Patent Publication No. JP-A-2013-517822 (Patent Document 2) showing the subordinate concepts thereof.

Patent Document 1

In Japanese Unexamined Patent Publication No. JP-A-2010-158315 (Patent Document 1), disclosed is the following: "A method for manufacturing an aphakic intraocular lens installed within the lens capsule for which a diffraction grating is provided having reliefs extending in concentric circles on the lens surface, wherein as the reliefs, used are a plurality of types of reliefs for which their respective diffractive primary light gives mutually different focal point distances, and for each grating pitch of the relief for which the grating pitch is maximum with the reliefs set overlapping each other, a synchronous structure is set for which the grating pitches with the other reliefs overlap periodically, and the obtained reliefs are formed on the lens surface."

Patent Document 2

In PCT Japanese Translation Patent Publication No. JP-A-2013-517822, disclosed is the following: "An intraocular lens (1) having a front surface (4) and a back surface (5) while also being equipped with a front-back optical axis (6), wherein one of the front surface (4) and the back surface (5) has a first diffraction profile (9) for which at least one first order +1 diffractive focal point (11) is formed on the optical axis (6), and a second diffraction profile (10) for which n order +1 second diffractive focal point (12) different from the order +1 first diffractive focal point (11) on the optical axis (6) is formed on the optical axis (6), wherein at least a portion of the second diffraction profile (10) overlaps at least a portion of the first diffraction profile (9) so that the order +2 of the second diffraction profile (10) is added to the order +1 of the first diffraction profile (9)."

As shown by the disclosed contents described above, the invention noted in Patent Document 1 features a diffractive structure for which in relation to the maximum grating pitch, the pitch of the other reliefs is set to periodically overlap. In other words, there is a request for a plurality of zones to periodically overlap one zone.

Also, the invention noted in Patent Document 2 features overlapping of a diffraction profile that gives diffraction +1 order light (called profile 1) and a diffraction profile for which diffraction +2 order light matches the focal point position of the +1 order diffracted light of the profile 1 (called profile 2). The structural relationship of profiles 1 and 2 in this case is a structure with which two zones of profile 2 are allocated to one zone of profile 1, and is a dependent invention limiting the invention noted in Patent Document 1.

However, with the conventional diffraction multi-focal type ophthalmic lenses noted in these Patent Documents 1 and 2, so as to give a detailed description with a specific example of a comparison example according to the background art structure with the Summary of the Invention section described later, when setting the addition power corresponding to intermediate vision in addition to near vision and far vision, there was the problem of intermediate focal point setting position limitations with which there was a restriction on the freedom of setting the focal point position for intermediate vision.

BACKGROUND ART DOCUMENT

Patent Document

Patent Document 1: JP-A-2010-158315
Patent Document 2: JP-A-2013-517822

SUMMARY OF THE INVENTION

Problem the Invention Attempts to Solve

[i] Definition of Terms

Following, before describing the summary of the present invention, terminology and the like used with the present invention is defined as follows.

The amplitude function (distribution) is a function (distribution) for which the characteristics as a light wave are described mathematically, and in specific terms, is expressed by Equation 2.

$$\text{Amplitude function} = \alpha e^{i\phi(x)} \text{ or Amplitude function} = \alpha \cos\{\phi(x)\} \quad \text{[Equation 2]}$$

x: Variable

Phase correlates to $\phi(x)$ in Equation 2, and is one parameter showing the status of light as a wave, and in specific terms, establishes the position of the valleys or peaks of the waves, or the positions for each elapsed time segment. Also, by changing the phase, the progress of the wave is advanced or delayed. With the present invention, phase is noted by $\phi$, and the unit is radians. For example, one wavelength of light is expressed as $2\pi$ radians, and half a wavelength as $\pi$ radians.

Phase modulation is the collective name for the structure or method provided on a lens so as to give changes in the phase by any method on light made incident to that lens.

Phase function is a function expressing phase change in the exponent part or the cos function of Equation 2. With the present invention, the phase function variable is used mainly as an item that has the radial direction position r from the center of the lens, and expresses the lens phase $\phi$ at the r point, and in specific terms, is expressed by the r–$\phi$ coordinate system shown in FIG. 1. Also, an item for which the phase distribution of the entire region in which the phase modulation structure is provided is expressed with the same coordinate system is called the phase profile, or simply a profile or zone profile. Note that the r axis of $\phi=0$ is the reference line, and at the point of $\phi=0$, it means that the incident light is emitted without changing the phase. Then, when a positive value is used for $\phi$ for this reference line, the light progress is delayed by that phase amount, and when a negative value is used for $\phi$, the light progress advances by that phase amount. With an actual ophthalmic lens, a refracting surface with no diffractive structure given correlates to this reference line (surface).

The optical axis is the lens rotation symmetrical axis, and here, means an axis for which the lens center extends to the object space and image side space.

0th order focal point means the focal point position of 0th order diffracted light. Hereafter, the +1 order diffracted light focal point position is called the +1 order focal point, the +2 order diffracted light focal point position is called the +2 order focal point, and so on.

A zone is used here as the minimum unit for the diffractive structure. For example, a region for which one blaze is formed is called one zone or zone region.

A blaze is one mode of a phase function, and indicates an item for which the phase is changing in a roof form shape, for example. With the present invention, the blaze is basically an item which changes in a straight line between the peaks (ridge lines) and valleys (trough lines) of the shed roof shapes in one zone shown in FIG. 2A which shows the cross section shape, but also included in the concept of a blaze with the present invention are items which, between the peaks and valleys, change in a parabola type curved line (FIG. 2B), irregular shapes (square wave shapes) (FIG. 2C), and the like. Also included in the blaze concept of the present invention are items which, between the peaks and valleys, are connected so as to change at a portion of the sine wave function (FIG. 2D), and items which are connected so as to change within an interval with no extrema. With the present invention, as shown in FIG. 2A, unless specifically noted, with the blaze of the ith zone, as a rule, with the absolute value of phase $\phi_i$ of the position of outer diameter radius $r_i$ of the zone and the absolute value of phase $\phi_{i-1}$ of the position of inner diameter radius $r_{i-1}$ set to be equal in relation to the reference surface (line), in other words, set so as to have $|\theta i|=|\phi_{i-1}|$, when the blaze is shifted in the 0 axis direction in relation to the reference line, the blaze position is determined by setting the phase shift t as shown in FIG. 2E. In other words, in the drawing, when the blaze is shifted upper than the reference line (plus direction), $\tau$ is a positive value, and when it is shifted lower than the reference line (minus direction), $\tau$ is a negative value. Based on this definition, the blaze phase function $\phi$ (r) is expressed as shown with Equation 3. The unit of the phase shift $\tau$ in Equation 3 is the radian. The notations for the peak and valley position phases when the phase shift $\tau$ is set and the blaze is shifted in the $\phi$ axis direction in relation to the reference line are respectively $\phi_i'$ and $\phi_{i-1}'$ in relation to the default setting phase $\phi_i$ and $\phi_{i-1}$ as shown in FIG. 2E. Specifically, there is a relationship of $\phi_i'=\phi_i+\tau$, $\phi_{i-1}'=\phi_{i-1}+\tau$.

$$\phi(r) = \frac{\phi_i - \phi_{i-1}}{r_1 - r_{i-1}} \times r + \frac{\phi_{i-1} \times r_i - \phi_i \times r_{i-1}}{r_1 - r_{i-1}} + \tau \qquad \text{[Equation 3]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift Phase constant means the constant h defined with Equation 4 for blaze shaped phase functions.

$$h = \frac{\phi_{i-1} - \phi_i}{2\pi} \qquad \text{[Equation 4]}$$

h: Phase constant
$\phi_{i-1}-\phi_i$: Phase difference between the phase of the inner diameter position and the phase of the outer diameter position of the ith diffraction zone For a plurality of profiles, a profile having a new phase function obtained by overlapping and adding the phase of each profile onto the same region of the radial direction of a zone is called a composite profile. When blaze shaped phase functions are synthesized, as shown in FIG. 3, blazes of profiles (1) and (2) are added in the radial direction and a blaze having new peaks and valleys are generated (FIG. 3C). The function expressing that blaze shaped phase is expressed similarly by Equation 3. With a composite profile, there are many cases when the newly generated blaze is shifted in the $\phi$ direction in relation to the reference line, so the notation of the blaze peak and valley positions with the composite profile is noted as $\phi_{i-1}'$, $\phi_i'$ as noted previously.

A relief is a generic name for the micro-uneven shaped structure reflecting the optical path length correlating to the phase established by the phase profile, specifically, formed on the surface of a lens by converting to the actual shape of the lens. The specific method for converting the phase profile to the relief shape is as noted hereafter.

When light enters into a medium with a certain refractive index, its speed is reduced according to the refractive index. The light wavelength change as much as the change in speed resulting in a phase change. Since a positive phase in the phase profile means reduced speed of light, incident light into a region of high refractive index is equivalent to bringing it to a positive phase. The terms positive and negative phases are relative expressions, and comparing the phases of $-2\pi$ and $-\pi$ for example, the latter lags behind the former even with the same sign, thus setting a region of higher refractive index than the former.

For example, when there is a blaze shaped phase function, the actual shape blaze step is expressed by Equation 5. That relief shape can be provided on the lens surface by machining it with a precision lathe or by a molding method.

$$\text{Blaze step} = h \times \frac{\lambda}{n_s - n_m} \qquad \text{[Equation 5]}$$

h: Phase constant
$\lambda$: Wavelength
$n_s$: Refractive index of the lens's base material
$n_m$: Refractive index of the medium facing the lens Intensity distribution is the intensity of light after passing through the lens plotted over a certain region, and is expressed as a conjugate absolute value of the amplitude function.

[ii] Problems the Present Invention is to Solve

The present invention was created with the background of the problems as described previously of having the degree of freedom for setting the intermediate focal point position being limited with diffractive type multi-focal lenses of a conventional structure, and the problem it is to address is to provide a diffractive type multi-focal lens of a novel structure and a novel method for manufacturing the same, which is a diffractive type multi-focal lens that can generate at least three focal points, and has a high degree of freedom in setting the focal point positions.

Here, to properly understand the technical significance of the present invention, in accordance with the inventions noted in Patent Documents 1 and 2, we will show the phase profile for the diffractive structure with one zone of the first zone profile synchronized and overlapped with two zones of the second zone profile, and a graph expressing the intensity distribution in the optical axis direction thereof, and will point out the specific problems of the background art.

Comparison Example 1

As comparison example 1, FIG. 4 shows a composite profile obtained based on Background art Documents 1 and 2, as well as the intensity distribution thereof. The first and second zone profiles having the blaze shapes shown separately in FIGS. 4A and 4B are overlapped to make the composite profile shown in FIG. 4C. Specifically, comparison example 1 is the zone profile shown in FIG. 4C that is synthesized by allocating the two blazes shown in FIG. 4A on one blaze shown in FIG. 4B, and in this case, when the addition power of the first zone profile is set as 4 D, the addition power of the second zone profile can be set as 2 D. Therefore, with this composite profile, a focal point peak for intermediate vision is generated at the 2 D point as shown in FIG. 4D. With the background art documents, it was not possible to form the focal point for intermediate vision at points of that refractive power or greater.

Comparison Example 2

As comparison example 2, FIG. 5 shows a specific example of a composite profile for which three blazes are allocated for one blaze based on Background art Document 1. The first and second zone profiles having the blaze shapes shown separately in FIGS. 5A and 5B are overlapped to make the composite profile shown in FIG. 5C. Specifically, comparison example 2 is the zone profile shown in FIG. 5C that is synthesized by allocating the three blazes shown in FIG. 5A to one blaze shown in FIG. 5B, and in this case, when the addition power of the first zone profile is set as 4 D, the addition power of the second zone profile can be set as 1.33 D. Therefore, with this composite profile, as shown in FIG. 5D, the focal point peak for intermediate vision is generated at the point of 1.33 D. With comparison example 2 as well, it is not possible to form a focal point at refractive power points greater than 2 D. Also, intermediate vision focal points are formed only at points of (1/X) times (X is a natural number) of the addition power 4 D of the first zone profile, in other words, to points limited to 1.33 D, 1 D, and 0.8 D, and it is not possible to form focal points at other than those points.

As can be understood from comparison examples 1 and 2 above, with the background art structure diffractive lenses shown in Patent Documents 1 and 2 which are the background art, as the addition power for intermediate vision, due to theoretical reasons described later, as shown by 1/2, 1/3, 1/4, . . . times the near addition power, it is only possible to set a maximum of 1/2 the addition power. For example, when assuming application to an intraocular lens, when the near focal point addition power is set to approximately 4 D as the guideline for the reading position, the intermediate focal point position can only be set to a position correlating to 4×(1/2)=2 D addition power at the maximum (the position closest to the near focal point). The focal point position when an intraocular lens set in this way is inserted into the human eye is approximately 35 cm in front with the near focal point, and the intermediate focal point position correlates to the position of approximately 65 to 70 cm to the front.

However, in recent years, as the use of personal computers has increased, there is also an increase in people of advanced age having opportunities to view personal computer monitor screens. Typically the average screen position when viewing a monitor screen is a position approximately 50 to 60 cm in front, so with the intermediate focal point position that can be set with the background art structure diffractive multi-focal lenses noted in Patent Documents 1 and 2, the intermediate focal point has to be set at a position further away than the monitor screen. Because of that, it is necessary to recede the position of the eye further from the monitor screen to clearly view the monitor screen, and this forces one to be in an uncomfortable posture. Also, if receding farther away, the text and the like on the monitor becomes smaller by that amount, ultimately causing the problem of that being difficult to see. To solve this kind of problem, there is a demand for a diffractive multi-focal lens of a novel specification for which it is possible to set the intermediate focal point more to the front than with the diffractive multi-focal lens realized using the inventions noted in Patent Documents 1 and 2.

In addition, with the diffractive multi-focal lens realized using the inventions noted in Patent Documents 1 and 2, when the addition power for near vision set with the power for far vision as the reference is diopter A, it is only possible to set the addition power for intermediate vision by a discontinuous value expressed by A/X (X is a natural number), and since it is difficult to make fine settings for addition power, there was the problem that there are cases when it is difficult to set an intermediate focal point to match the needs of the patient or user.

[iii] Other Problems that the Present Invention can Solve Optionally as Needed

As described above, as a result of intense research by the inventors to address the problems, they became aware of other problems intrinsic to the diffractive lenses of the background art structure described previously, and for those other problems as well, it became clear that it is possible to solve those using the present invention as needed. Therefore, with the present invention, in addition to the problems described above, it also able to suitably handle as necessary other problems noted hereafter as well.

As another problem for the present invention to optionally solve, with the diffractive type multi-focal type lens, for example, there are cases of handling a demand to suitably realize preferred focal points to match the status of the user (patient). Specifically, when wearing or inserting in the eye an ophthalmic lens such as a contact lens, intraocular lens or the like, the light flux that is emitted from the ophthalmic lens or that is made incident on the lens is determined by the size of the pupil of the eye. Therefore, for the effective aperture diameter of the lens side that substantially determines the incident and emission of light, if the pupil changes, that also changes correspondingly. The diffractive multi-focal lenses of the Background art Documents noted above have as a basic characteristic the fact that the number of focal points and the position of the focal points do not change even if the aperture diameter changes.

That characteristic sometimes brings the problem of a decrease in energy efficiency of the light due to the generation of unnecessary focal points.

The size of the pupil changes with the brightness of the light, with the pupil becoming smaller when it is bright, and becoming larger when it is dark. The pupil has the function of adjusting the amount of light that enters the eye, and it also has the function of adjusting the depth of focus. Typically in environments in which the light illuminance is very high, such as in fine weather outdoors or the like, the human pupil becomes quite small. When the pupil becomes smaller, the depth of focus becomes deeper, so for example in such an environment, even with a monofocal lens for which the focal point is for far, it is sometimes possible to focus as far as in the intermediate region. Similarly, even in a case of using a bifocal lens for which there are focal points both for both far and near, in fine weather outdoors or the like, the respective focal depths both become deeper. As a result, the intermediate region is compensated not only by the far vision depth of focus but also by the near vision depth of focus, and it is sufficiently possible to see objects in the intermediate region even with a bifocal lens with only two focal points for far and near vision. In other words, in this environment, it is not in fact necessary to provide an intermediate focal point. On reflection, with the diffractive lenses of the Background art Documents, because there is the characteristic of the intermediate focal point being generated regularly regardless of the size of the aperture diameter, the intermediate focal point is generated even in a situation like that noted above when the intermediate focal point is not necessary. An increase in the number of focal points means distributing from other focal points the energy volume for light for generation of the newly set focal points, and there are cases when there is a decrease in brightness or contrast when viewing an object at the distribution source focal point. There is a risk that this decrease in brightness or contrast will lead to reduced quality of vision, so it is preferable to not set unnecessary focal points when not necessary.

When we think of the task of using the personal computer as the subject task when viewing the intermediate region, the environment for performing that work is mainly standard indoor illuminance (brightness under fluorescent light). With this environment, the illuminance is lower than the environment of fine weather outdoors, so accordingly, the pupil dilates to some degree. When the pupil dilates, the depth of focus becomes shallower, so it becomes difficult to cover the intermediate region using the depth of focus. Therefore, first it is necessary to provide specifications for generating an intermediate focal point in the lens aperture region corresponding to the pupil diameter in that environment. If the aperture region for which the intermediate focal point needs to be generated is regarded as a transition region, it is preferable to use the following specifications: for the aperture diameter smaller than the transition region, the lens is designed to have only two focal points at far and near distances so as not to deteriorate the quality of vision; and for the transition region, the lens is designed to have a diffractive structure such that the intermediate focal point starts to be generated in addition to the two focal points.

Such specifications by which a plurality of different focal points are separately given to the regions within the lens are sometimes required in addition to the case where the far and near focal points are combined with the intermediate focal point. That is the case for providing a diffractive lens for giving the far and near focal points as well as the focal points to an even nearer position. With initial stage presbyopia patients who still have about 2 D of power of accommodation remaining, it is possible to see from the far focal point to the point at about 50 cm in front. Therefore, since the necessity and importance of the specifications for generating the intermediate focal point are not that high, the basic prescription of a multi-focal lens for such a patient is the far and near two focal points. However, for those patients as well, yet a further focal point in some cases becomes necessary at a position different from far and near. In environments in which the illuminance has decreased such as dimly lit indoors or the like, there is generally a tendency for the contrast of the object to decrease. In this case, even if a focal point is provided for near vision, there are cases when it is not possible to sufficiently see items positioned closer depending on the text size or contrast. In that situation, in many cases, the person takes the physiological action of coming closer to the object to view it more closely. In this case, in addition to the two focal points for far and near, if a separate focal point is given at a point positioned even nearer, it is possible to give clearer vision when coming even closer to an object. In that situation, the lens aperture diameter corresponding to the pupil diameter for twilight level brightness is regarded as the transition region. Therefore, as a multi-focal lens for this situation, within the transition region, bifocal specifications for far and near visions are basically set, and to the region outside the transition region, it is preferable to set the specifications that are able to give another near focal point for viewing even closer objects. That multi-focal lens needs to generate a nearer focal point in the lens region corresponding to the diameter when the pupil is dilated (this will probably be the peripheral part with the diffractive structure).

There is also a desire for provision of a diffractive multi-focal lens with the necessary focal points arranged effectively in each lens region according to the patient's use environment and requirement, but with the background art structure diffractive type multi-focal lens, it was extremely difficult to handle that kind of demand.

Means for Solving the Problem

The characteristic modes of the present invention created with the object of addressing the Problems the Present Invention Is to Solve of [ii] described above are expressed as follows using the terminology defined as described previously. The Other Problems That The Present Invention Can Solve Optionally As Needed of [iii] described previously are not problems for which it is essential to be solved by the present invention. Therefore, the problems of [iii] are not problems to be solved for all the modes noted hereafter or the examples described later, but rather are to be understood as items for which it is sufficient to be solved with a portion of the modes or a portion of the examples.

The first mode of the present invention is a diffractive multi-focal lens having a diffractive structure comprising a plurality of zones in a concentric circle form, characterized in that: the diffractive structure includes an overlapping region for which at least two zone profiles are overlapped on the same region in at least a portion thereof; and at the overlapping region, at least a portion of a first zone profile of the at least two zone profiles has a zone pitch expressed by Equation 6, and at least a portion of a second zone profile of the at least two zone profiles has a zone pitch expressed by Equation 7, and an addition power $P_1$ given by the first zone profile and an addition power $P_2$ given by the second zone profile are determined by a relational expression of Equation 8, where a and b are mutually different real numbers, and a value of a/b is a value that cannot be expressed by a natural number X or by 1/X. The setting equations of the zone pitches expressed by Equation 6 and Equation 7 when making explanations hereafter shall be called "general setting equations."

$$r_n = \sqrt{r_1^2 + \frac{2\lambda(n-1)}{P_1}}$$ [Equation 6]

$\lambda$: Design wavelength
$r_n$: nth zone radius of the first zone profile
$r_1$: First zone radius of the first zone profile
$P_1$: Addition power of the first zone profile
n: Natural number $$r_m = \sqrt{r_1'^2 + \frac{2\lambda(m-1)}{P_2}}$$ [Equation 7]

$\lambda$: Design wavelength
$r_m$: mth zone radius of the second zone profile
$r_1'$: First zone radius of the second zone profile
$P_2$: Addition power of the second zone profile
m: Natural number $$P_2 = \frac{a}{b} \times P_1$$ [Equation 8]

With the diffractive multi-focal lens having a structure according to this mode, as is clear from the analysis and examples described hereafter, it is possible to set at least three focal points with a large degree of freedom of design and high precision for the focal point positions on the optical axis.

Specifically, by performing many experiments and studies, the inventors obtained the novel knowledge. That is, the synchronous conditions proposed previously by the invention described in Patent Document 1 were limited conditions in which a plurality of zones were synchronized with one zone. Meanwhile, the present invention makes it possible to further expand such synchronous conditions. Also, with the present invention that was completed based on this knowledge, the ratio of the relative period count relationship of the mutually overlapping zone region of the first zone profile and the zone region of the second zone profile is obtained without limit compared to the invention noted in Patent Document 1, and by satisfying the condition that when a and b expressed by Equation 8 are used as a/b and that a/b must be other than X or 1/X (X is a natural number), it becomes possible to set the position of the intermediate focal point with a great degree of freedom of design. In specific terms, the examples described later can be referenced, with the first zone profile that gives the addition power $P_1$ and the second profile that gives the addition power $P_2$, the addition power $P_1$ and $P_2$ are determined by Equation 8, and by constituting a zone profile with those overlapped and synthesized (composite profile), in addition to the addition power by the first zone profile, it is possible to additionally set easily and with high precision a suitable diopter value of an addition power of a different diopter value from that.

As is described later, a region for which first and second zone profiles are overlapped and provided is not necessary across the entire lens optical region, and it is acceptable to provide it partially in the lens radial direction. For example, it is also possible to form the first zone profile along the entire lens optical region, and overlap the second zone profile only on limited regions of the lens radial direction on the first zone profile. Also, as is described later with the ninth mode, in regions for which the first and second zone profiles are overlapped, it is also possible to further provide a third zone profile overlapping.

The second mode of the present invention is the diffractive multi-focal lens according to the first mode, wherein a and b in Equation 8 are mutually different integers of zero or greater, and quotients when a and b are divided by a mutual greatest common divisor thereof are both an integer other than 1.

According to this mode, with Equation 8 that determines the addition power $P_2$ given by the second zone profile, by having a and b be an integer of zero or greater, it is possible to mutually correlate the number of zones constituting the first and second zone profiles and the addition power $P_1$ and $P_2$ with integers a and b as described later. Then, as a result, the profile that is overlapped and synthesized as a result has a repeated structure of periodic zones, and it becomes possible to obtain a diffractive multi-focal lens for which the generation of at least three focal points is reliably expressed across the entire region of the composite profile.

With this mode, in the lens radial direction, it is possible to have a synchronous structure by which the zone diameter of the first zone profile and the zone diameter of the second zone profile match, or as shown with example 8 described later, it can also have an asynchronous structure for which none of the zone diameters match. Regardless of whether synchronous or asynchronous, with profiles that have been overlapped and synthesized, it is possible to form a periodic structure, and with this structure, it is possible to obtain a diffractive multi-focal lens that can realize at least three focal points. With this periodic structure, it is not necessary for one period or greater to be formed in the lens radial direction, and it is possible to have a first and second zone profile provided overlapping in a radial direction region that is not one full period. Specifically, as long as the target focal points are realized, a mode having only one zone in a region for which at least one of the first zone profile and the second zone profile is overlapped is also included.

The third mode of the present invention is the diffractive multi-focal lens according to the first or second mode, wherein a and b in Equation 8 are set to be a/b>1/2.

With this mode, for example by setting a relationship for which the addition power $P_2$ by the second zone profile in relation to the addition power $P_1$ by the first zone profile is set to be $P_2 > P_1 \times (1/2)$, the focal point set at a position in the intermediate between far and near can be set even closer to the near focal point, and for example with an ophthalmic lens, when near vision is used for reading, it is possible to set the focal point at a position suitable for viewing a personal computer screen. As is described also with the fourth mode described later, with this mode, the b-number of zone regions of the first zone profile and the a-number of zone regions of the second zone profile having a mutually synchronous relationship, for example, can be realized advantageously by setting with a relationship of a/b>1/2.

The fourth mode of the present invention is the diffractive multi-focal lens according to any of the first to third modes, wherein in regards to a and b in Equation 8, a synchronous structure, for which a b-number of zone pitches that are continuous in the first zone profile and an a-number of zone pitches that are continuous in the second zone profile are mutually the same within the same region, is set for at least a portion of the overlapping region of the diffractive structure.

With this mode, since zone pitches having a mutually synchronous structure for the first and second zone profiles are provided in the same overlapping region, it is possible to obtain a simplified composite profile structure.

The fifth mode of the present invention is the diffractive multi-focal lens according to any of the first to fourth modes, wherein a first zone radius rj of the first zone profile and a first zone radius $r_1'$ of the second zone profile are expressed respectively by Equation 9 and Equation 10.

$$r_1 = \sqrt{\frac{2\lambda}{P_1}} \quad \text{[Equation 9]}$$

$$r_1' = \sqrt{\frac{2\lambda}{P_2}} \quad \text{[Equation 10]}$$

In accordance with this mode, it is possible to set the first and second zone pitches using a more simplified Fresnel pitch, and possible to easily perform design of the diffractive structure, and also possible to efficiently confirm with good precision the diffracted light using a method such as simulation or the like.

Specifically, in a case when the diffractive structure is constituted from concentric circle zones having Fresnel pitches, for the first zone profile for which the addition power is $P_1$ and the second zone profile for which the addition power is $P_2$, by using Equation 9 and Equation 10, it is possible to express their respective zone radii $r_n$ and $r_m$ using Equation 11 and Equation 12 noted below.

nth zone radius of the first zone profile [Equation 11]

$$r_n = \sqrt{\frac{2n\lambda}{P_1}}$$

mth zone radius of the second zone profile [Equation 12]

$$r_m = \sqrt{\frac{2m\lambda}{P_2}}$$

When Equation 8 which is the relational expression of the addition power $P_1$ of the first zone profile and the addition power $P_2$ of the second zone profile is substituted with Equation 12, for the mth zone radius of the second zone profile, Equation 13 noted below is obtained.

$$r_m = \sqrt{\frac{2bm\lambda}{aP_1}} \quad \text{[Equation 13]}$$

Here, when $r_n$ and $r_m$ are made to be equal, from Equation 11 and Equation 13, the relational expression of Equation 14 noted below is obtained.

$$\sqrt{\frac{2n\lambda}{P_1}} = \sqrt{\frac{2bm\lambda}{aP_1}} \quad \text{[Equation 14]}$$

Furthermore, from Equation 14 noted above, the relational expression of Equation 15 is obtained.

$$a \times n = b \times m \quad \text{[Equation 15]}$$

Here, n and m express zone numbers, and an integral value must be used. When a and b are integral values of zero or greater, there will always be a combination of n and m for which both sides of the equal sign of Equation 15 are equal. In other words, for n and m, $a \times b \times \Omega$ ($\Omega$ is a natural number) which is a common multiple of a and b are divided respectively by a or b. Therefore, the zone radius that matches between the first and second zone profile can be specified using the zone numbers n and m with Equation 16 and Equation 17.

$$n = b \times \Omega (\Omega: \text{Natural number}) \quad \text{[Equation 16]}$$

$$m = a \times \Omega (\Omega: \text{Natural number}) \quad \text{[Equation 17]}$$

Said another way, the addition power of the second zone profile is expressed by Equation 8, and by having a and b be mutually different integers of zero or greater, based on Equation 15, it is possible to set a zone count so that the zone radius between zone counts n and m match, in other words, so that the zones are synchronized. Specifically, it is possible to set a zone count by which the zones are synchronized.

For example, when the addition power of the second zone profile is $P_2 = P_1 \times (3/4)$, a=3 and b=4, so . . . from Equation 16 and Equation 17, the zone radii of the respective diffraction profiles for every zone count of n=4, 8, 12, . . . , m=3, 6, 9, are synchronized and matched (see example 1 described later (FIGS. 6A, 6B). By overlapping these profiles that can be synchronized with each other, the diffractive structure of the present invention is constituted, and using this overlapping diffractive structure, the diffractive multi-focal lens having a focal point at a specific intermediate position is realized. Incidentally, in regards to this kind of theoretical relationship of addition power and the synchronous zone count, with the background art document group, since they have a structure in which a plural b-number of zones are allocated to one zone (a=1), the addition power is limited to 1/b, in other words, 1/2, 1/3, 1/4, . . . .

With the examples described later, the setting equation that determines the zone pitches with Equation 11 and Equation 12 will be called the "standard setting equation."

Regardless of Equation 15 noted above, the numerical expression that specifies the present invention expresses the technical concept and is a design guideline, but it also generates errors with manufacturing processes and the like, for example. Because of that, as a requirement of the diffractive multi-focal lens provided by being manufactured with a structure according to the present invention, it is sufficient as long as each numerical expression requirement is satisfied so as to achieve the target technical effect, and in regards to the dimensions of the diffractive structure with the diffractive multi-focal lens which is a product, a strict mathematical interpretation is not required, and it is sufficient as long as the optical operational effects that are the object of the present invention are exhibited. For example, by setting a/b mathematically to an irrational number or the like, even with a mode for which there is not a complete mathematical match of the zone radii of designated periods that are synchronous in the radial direction, by there being a synchronous structure for which it is regarded as being essentially synchronous in a range for which there are no optical problems, it is possible to realize a multi-focal intraocular lens equipped with optical characteristics that achieve the object of the present invention. Said another way, the technical concept of whether a/b is a rational number or irrational number being expressed mathematically is clear, but it is not necessary for the diffractive lens to be a specific structure, and as long as the target optical characteristics are achieved, this can be thought of as being included not only in the first mode of the present invention, but also in the scope of any of the second to fifth modes (see example 9 described later (FIG. 14) and the like).

Also, with the description above, with the first zone profile and the second zone profile, a mode was used for which the zone radii matched for each synchronous designated zone, but with the present invention, it is not essential that the zone radii match for each synchronous zone count. For example, it is also possible to have the zone radii of synchronous positions be different from each other by having the zone radii shifted overall (see example 8 described later (FIG. 13)).

The sixth mode of the present invention is the diffractive multi-focal lens according to any of the first to fifth modes, wherein in the overlapping region, at least one type of equal-pitch zone is provided for which two or more zones are provided at equal pitches on at least one of the first zone profile and the second zone profile.

With the diffractive multi-focal lens constituted according to this mode, in the overlapping region, an equal-pitch zone is set for both or one of the first and second zone profiles.

Also, with the diffractive multi-focal lens of this mode, for example as also shown with example 10 described later (FIG. 15), though the composite profile is a regularly repeating item in the equal-pitch zone overlapping region, by setting a synchronous relationship for the first zone profile and the second zone profile, it is also possible to set an intermediate focal point. Also, for the addition power $P_2$ that is the intermediate focal point as well, in cases when the zone count b of the first zone profile and the zone count a of the second zone profile are synchronous, by adjusting the relative relationship of a and b, it is possible to adjust and set the value of addition power $P_2$ that gives the intermediate focal point in relation to the addition power $P_1$ of the near focal point.

It is possible to interpret this mode by understanding it as a combination with the m=1 Fresnel pitch with Equation 7 with the first mode of the present invention. Specifically, though when m=1 with Equation 7 the addition power $P_2$ does not have a specific value, by interpreting this as correlating to a case of a=0 with Equation 8, since this does not deviate from each numerical expression specifying the first mode, this mode is also included within the scope of the present invention specified by the first mode. Incidentally, a mode for which the entire region of the overlapping region for the first and second zone profiles is set as a same pitch zone can also be expressed using a numerical expression that specifies the first mode as a mode for which m=1 with Equation 7 and all the zones have equal pitches at $r_1'$, and therefore is included within the scope of the present invention. When overlapping either of the first and second zone profiles as an equal-pitch zone, the definition of the addition power based on the Fresnel pitch setting equation no longer applies, but for example with Equation 8, by grasping an item for which with a or b as 0, the addition power is zero or infinity as being an expediently addition power for equal pitches, the establishment of the numerical expressions described above is not negated.

The seventh mode of the present invention is the diffractive multi-focal lens according to the sixth mode, wherein the equal-pitch zone is provided adjacent in a lens radial direction in relation to at least one of the region for which the zone pitch is represented by Equation 6 with the first zone profile, and the region for which the zone pitch is represented by Equation 7 with the second zone profile.

With the diffractive multi-focal lens of this mode, the equal-pitch zone region is provided aligned in the lens radial direction with the Fresnel pitch zone region for at least one of the first zone profile and the second zone profile, and with the optical characteristics of the composite profile obtained by overlapping the first and second zone profiles, it is possible to reflect both the optical characteristics caused by the equal-pitch zone and the optical characteristics caused by the Fresnel pitch zone.

The eighth mode of the present invention is the diffractive multi-focal lens according to the sixth or seventh mode, wherein the at least one type of equal-pitch zone comprises a plurality of types of equal-pitch zones for which mutually different zone pitches are set.

With the diffractive multi-focal lens of this mode, by suitably combining and using the plurality of types of equal-pitch zones for which mutually different zone pitches are set, it is possible to realize an even greater degree of freedom of design for optical characteristics such as optical axis direction light intensity distribution and the like (see example 11 (FIG. 16)).

The ninth mode of the present invention is the diffractive multi-focal lens according to any of the first to eighth modes, wherein in addition to the first zone profile and the second zone profile, a third zone profile is set, and the diffractive structure includes the first, second, and third zone profiles overlapped on the same region.

In accordance with this mode, for example as is shown in examples 16 to 20 (FIG. 21 to 25) described later, a composite profile for which at least three types of zone profiles having a synchronous relationship in relation to mutually different zone profiles overlapping is used for at least a portion of the diffractive structure. By working in this way, by having at least three types of zone profile overlapped, it is possible to set the position of the plurality of intermediate focal points corresponding to each of the overlapped zone profiles. In particular, by having a plurality of other zone profiles set all having a synchronous relationship to the first zone profile, it is possible to more easily and efficiently perform setting of the positions of the plurality of intermediate focal points.

The tenth mode of the present invention is the diffractive multi-focal lens according to the ninth mode, wherein at least a portion of the third zone profile has a zone pitch given by Equation 18, and an addition power $P_3$ given by the third zone profile is different from both of the addition powers given by the first and second zone profiles.

$$r_q = \sqrt{r_1''^2 + \frac{2\lambda(q-1)}{P_3}} \qquad \text{[Equation 18]}$$

$\lambda$: Design wavelength
$r_q$: qth zone radius of the third zone profile
$r_1''$: First zone radius of the third zone profile
$P_3$: Addition power of the third zone profile
q: Natural number In accordance with this mode, in addition to the first and second zone profiles, the third zone profile also has at least a portion of the zone region set with the Fresnel pitch, and by doing that, when setting a composite profile with three types or more of zone profiles overlapping, it is possible to more easily and with good precision perform optical characteristics adjustment and design.

The eleventh mode of the present invention is the diffractive multi-focal lens according to the tenth mode, wherein a first zone radius $r_1''$ of the third zone profile is expressed by Equation 19.

$$r_1'' = \sqrt{\frac{2\lambda}{P_3}} \qquad \text{[Equation 19]}$$

In accordance with this mode, the zone pitch setting equation of Equation 18 of the third zone profile shown with the tenth mode is expressed as a more simplified standard setting equation of Equation 20, and in addition to it being possible to easily perform design of the diffractive structure, it is also possible to with good precision and efficiently confirm the diffracted light with a method such as simulation or the like.

$$r_q = \sqrt{\frac{2q\lambda}{P_3}} \qquad \text{[Equation 20]}$$

The twelfth mode of the present invention is the diffractive multi-focal lens according to any of the ninth to eleventh modes, wherein at least a portion of the diffractive structure has a synchronous structure for which, with $c_1$, $c_2$ and $c_3$ all being mutually different natural numbers, a $c_3$-number of zone pitches continuous in the third zone profile is the same as either a $c_1$-number of zone pitches continuous in the first zone profile or a $c_2$-number of zone pitches continuous in the second zone profile.

With the diffractive multi-focal lens constituted according to this mode, the addition power $P_3$ of the third zone profile is set having the synchronous zone pitch expressed by the relationship $P_3=(c_3/c_1)\times P_1$ or $P_3=(c_3/c_2)\times P_2$ in relation to at least one of the addition power $P_1$ of the first zone profile or the addition power $P_2$ of the second zone profile.

With this mode, the first, second, and third zone profile zone regions can also respectively be set having an asynchronous relationship with one zone region of any other zone profile, but on the other hand, with the relational expression of $P_3=(c_3/c_1)\times P_1$ or $P_3=(c_3/c_2)\times P_2$, by having $c_3$, or $c_1$ or $c_2$ be 1, the third zone profile and the first or second zone profile can also be set to be synchronous having a relationship of a zone count of 1:X (or X:1) with X being a natural number. In this way, the synchronous relation of the zone region of the third zone profile in relation to the first and second zone profiles can be set with a high degree of freedom, and based on that, it is also possible to ensure a high degree of freedom for setting the focal point position given by the third zone profile.

The thirteenth mode of the present invention is the diffractive multi-focal lens according to any of the ninth to twelfth modes, wherein an addition power $P_3$ given by the third zone profile is determined by Equation 21, and with a greatest common divisor being z for three integers of (b×e), (a×e), and (b×d) expressed using d and e in Equation 21 and a and b in Equation 8, at least a portion of the diffractive structure has a synchronous structure for which a (b×e)/z-number of continuous zone pitches in the first zone profile, an (a×e)/z-number of continuous zone pitches in the second zone profile, and a (b×d)/z-number of continuous zone pitches in the third zone profile are mutually the same.

$$P_3 = \frac{d}{e} \times P_1 \qquad \text{[Equation 21]}$$

(d, e: Mutually different integers of zero or greater)

With the diffractive multi-focal lens constituted in accordance with this mode, by using the greatest common divisor z, based on the relationship of addition powers $P_1$, $P_2$, and $P_3$ given respectively by the first, second, and third zone profiles, it is possible to simplify and easily understand the synchronous relationship mutually between each zone pitch of the first, second, and third zone profiles. Also, by using the concept of this mode, for example as shown in example 19 described later, in cases when there is a different number of rational number denominators shown by Equation 8 and Equation 21 for setting the addition power of the first, second, and third zone profiles, by arranging the rational number denominators of each zone profile using the least common multiple, it is possible to understand the number of numerators as a number of synchronous zones of a repeated structure.

The fourteenth mode of the present invention is the diffractive multi-focal lens according to any of the ninth to thirteenth modes, wherein in addition to the first zone profile, the second zone profile, and the third zone profile, a fourth zone profile is also set, and the diffractive structure includes the first, second, third, and fourth zone profiles overlapped on the same region.

The fifteenth mode of the present invention is the diffractive multi-focal lens according to the fourteenth mode, wherein in addition to the first zone profile, the second zone profile, the third zone profile, and the fourth zone profile, a fifth zone profile is also set, and the diffractive structure includes the first, second, third, fourth, and fifth zone profiles overlapped on the same region.

With the diffractive multi-focal lens constituted in accordance with the fourteenth and fifteenth modes of the present invention, by setting regions with four or more types of zone profiles having mutually different zone pitches overlapped for at least a portion of the diffractive structure, by setting five or more or six or more focal point positions on the optical axis or the like, it is possible to ensure an even greater degree of freedom of adjusting the light intensity distribution on the optical axis, and for example it is possible to also make clearer the field of vision with a broader focal point position.

The sixteenth mode of the present invention is the diffractive multi-focal lens according to any of the first to fifteenth modes, wherein the diffractive structure is formed with a diffractive structure characterized by a phase function to modulate a phase of a light.

With the diffractive multi-focal lens of this mode, for example by wavelength order depth unevenness or refractive index distribution or the like being formed on the lens surface or lens interior periodically or quasi-periodically in the lens radial direction, a phase modulation type diffractive structure is used. As a result, compared to an amplitude modulation type diffractive structure that modulates amplitude a of Equation 2, it is possible to prevent loss of incident light and have good diffraction efficiency for converting to diffracted light.

The seventeenth mode of the present invention is the diffractive multi-focal lens according to the sixteenth mode, wherein the phase function comprises a blaze shaped function.

In accordance with this mode, it is possible to set the first order diffraction efficiency to be sufficiently large by using a blaze shape that is typically called a serrated shape, and it is also possible to easily and with good precision design the diffractive structure using a well known arithmetic expression. With the diffractive multi-focal lens of this mode, as this blaze shaped phase function $\phi(r)$, for example, the items shown with the eighteenth mode below can be preferably used, for example.

Specifically, the eighteenth mode of the present invention is the diffractive multi-focal lens according to the seventeenth mode, wherein the blaze shaped phase function $\phi(r)$ is expressed by Equation 22.

$$\phi(r) = \frac{\phi_i - \phi_{i-1}}{r_1 - r_{i-1}} \times r + \frac{\phi_{i-1} \times r_i - \phi_i \times r_{i-1}}{r_1 - r_{i-1}} + \tau \quad \text{[Equation 22]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift The nineteenth mode of the present invention is the diffractive multi-focal lens according to any of the first to eighteenth modes, wherein the diffractive structure comprises a relief structure reflecting an optical path length correlating to a phase.

For the relief that gives diffracted light with this mode, it is especially preferable to use a surface relief type such as an uneven type, a film thickness modulation type or the like. Also, by using the relief type diffractive structure in accordance with this mode, it is possible to generate diffracted light with good precision using a geometrical uneven shape, so it is possible to improve the focal point design and precision.

As the relief in accordance with this mode, when forming an uneven surface such as the blaze shape described previously or the like, aside from a method using machining processing such as cutting or the like, in addition to processing of optical elements such as a glass substrate or the like using developing processing using electron beam resist and electron beams, it is possible to use various types of well known relief processing technology such as processing technology of the optical elements using repetition of a semiconductor process of film thickness lamination using photolithography and etching or the like.

The twentieth mode of the present invention is the diffractive multi-focal lens according to any of the first to nineteenth modes, wherein the diffractive multi-focal lens is an ophthalmic lens.

With the diffractive multi-focal lens constituted according to this mode, by being thinner than the refraction type, for example when using as an ophthalmic lens such as an intraocular lens, contact lens or the like, while maintaining the excellent points of the diffractive type multi-focal lens of reducing the burden on the patient, being easy to handle by the practitioner or the like, by improving the degree of freedom of tuning the optical characteristics such as the focal point position or the like, it is possible to put into practical use an ophthalmic lens with high quality vision commensurate with the high level demanded by patients.

The twenty-first mode of the present invention is the diffractive multi-focal lens according to any of the first to twentieth modes, wherein the diffractive multi-focal lens is able to generate at least three focal points.

With this mode, for example in addition to having one of the three focal points be a far focal point, another focal point is a near focal point. Also, by following the present invention as noted in the first mode, between the far focal point using 0th order diffracted light and the near focal point using the addition power by the first zone profile, it is possible to also set an intermediate focal point at a position further toward the far focal point or further toward the near focal point than the intermediate position, for example, and it is possible to easily set the diopter value corresponding to each required focal point with a high degree of freedom.

The twenty-second mode of the present invention is the diffractive multi-focal lens according to the twenty-first mode, wherein the diffractive multi-focal lens is an ophthalmic lens for which of the three focal points, one focal point is used for far vision, and another focal point is used for near vision, and the other focal point is used for intermediate vision.

With this mode, for example by applying the present invention to an ophthalmic lens such as a contact lens, intraocular lens, eyeglasses or the like, in addition to the focal point for far vision used for when driving a car or the like and the focal point for near vision used for reading or the like, it is possible to set a focal point for intermediate vision used for personal computer work or the like. In light of that, the focal point position for intermediate vision can also be set at a position near the focal point position for near vision, for example, so considering the user's living environment or the like, it is possible to suitably set each focal point position with a high degree of freedom so as to realize a focal point position suited for the user.

The twenty-third mode of the present invention is the diffractive multi-focal lens according to the twenty-second mode, wherein the focal point for far vision is given by a 0th order diffracted light of the diffractive structure, and the focal point for near vision and the focal point for intermediate vision are given by a +1 order diffracted light by the first zone profile and the second zone profile.

With the diffractive multi-focal lens constituted according to this mode, with at least three focal points, the focal point for far, the focal point for near, and the focal point for intermediate region between those are given by the diffractive structure 0th order or +1 order diffracted light, so it is even easier to set the concentrated light and thus the light energy for each focal point.

The twenty-fourth mode of the present invention is the diffractive multi-focal lens according to any of the twenty-first to twenty-third modes, wherein at least three focal points given by the overlapping region for which the first zone profile and the second zone profile are overlapped are generated with a lens aperture diameter of a predetermined setting diameter or greater.

With this mode, considering the fact that when the lens aperture diameter is made smaller, the depth of focus becomes deeper, for example, while three focal points are realized in a state for which the lens aperture diameter is larger and the depth of focus is shallower, by having one or two focal points in a state for which the lens aperture diameter is small and the depth of focus is deep, it is also possible to increase the light condensing rate of the light energy to those few focal point positions.

In particular by applying this mode to an ophthalmic lens, considering the fact that when the pupil contracts according to the level of brightness in the environment, the depth of focus becomes deeper, by essentially eliminating the optical characteristics by the composite profile at the optical diameter of diameter of 2 mm or less, for example, the focusing function for intermediate vision in fine weather outdoors or the like is suppressed, and it is possible to improve the contrast by efficiently ensuring the light energy volume at each required focal point for far and near. When applying this mode to an ophthalmic lens, it is preferable to set the setting diameter relating to the lens aperture diameter to a suitable value within a range of 0.8 to 3 mm, such as 2 mm or the like, for example.

The twenty-fifth mode of the present invention is the diffractive multi-focal lens according to any of the first to twenty-fourth modes, wherein with a position of an outer diameter radius of an nth zone, n being a natural number, of the first zone profile being a boundary radius position, at one side of an inner circumference side and an outer circumference side of the boundary radius position, the diffractive structure of the first zone profile is provided but the diffractive structure of the second zone profile is not provided, and at the other side of the inner circumference side and the outer circumference side of the boundary radius position, the diffractive structure for which the first zone profile and the second zone profile are overlapped is provided.

With this mode, at the boundary radius position of the composite profile for which the first and second zone profile are overlapped, and the non-composite profile for which only one of the first or second zone profile is provided, it is not necessary for the radii of the first zone profile and the second zone profile to match each other (see example 12 described later), but with a specific mode of this mode, the zone radius with the second zone profile is set to be synchronous at the position of the nth zone radius with the first zone profile, and these are positioned using the same zone radius (see example 13 described later).

The twenty-sixth mode of the present invention is the diffractive multi-focal lens according to the twenty-fifth mode, wherein at the inner circumference side of the boundary radius position, the diffractive structure of the first zone profile is provided but the diffractive structure of the second zone profile is not provided, and at the outer circumference side of the boundary radius position, the diffractive structure for which the first zone profile and the second zone profile are overlapped is provided.

With the diffractive multi-focal lens of this mode, for example in a case for which the size of the lens effective aperture is changed by the optical device stop, the iris of the eye or the like, when the size of the effective aperture is made smaller, the focal point from the second zone profile is not generated. However, when the size of the effective aperture is made larger beyond the boundary radius position, the focal point from the second zone profile appears. Because of that, for example as described previously, in a state for which the effective aperture is small, while satisfying the imaging performances at points with different distances with a large depth of focus, while ensuring the light amount by increasing the light focusing efficiency to a focal point of a specific position, it is possible to ensure clarity of an image at points with different distances by increasing the number of focal points on the optical axis when the depth of focus has become shallow due to the effective aperture becoming larger.

Also, with the diffractive multi-focal lens constituted according to this mode, it is possible to suitably adjust the position of the second zone profile in the lens radial direction, and for example by using this for an ophthalmic lens, by setting the position of each zone region taking into consideration the changes in pupil diameter with photopic vision, mesopic vision, and scotopic vision, it is possible to substantially generate the necessary focal points according to the environment such as illuminance and the like. Furthermore, with the diffractive multi-focal lens of this mode, it is possible to suitably adjust and set at which position in the lens radial direction and at what level of radial direction width to provide the second zone profile, and by doing that, for example when using this for an ophthalmic lens, it is possible to do tuning of the conditions for the addition power to be manifested, the light intensity at the focal point position or the like used with intermediate vision and the like.

With the diffractive multi-focal lens of the present invention, by making a variable setting for the first zone radius at least at one of the first zone profile and the second zone profile, while maintaining the Fresnel zone relational expression, it is possible to do change setting from the second zone pitch and thereafter. Because of that, for example as shown in examples 6 to 8 described later (FIG. 11 to 13), by doing a variable setting of the first zone radius with the first zone profile and the second zone profile, it is possible to adjust the lens diameter region for which three focal points are generated. In specific terms, for example in a region for which the lens aperture diameter is small as well, it is possible to set three focal points using a composite profile.

Also, with the diffractive multi-focal lens of the present invention, when setting a partial overlapping region by providing the second zone profile overlapping the first zone profile only in a specific region of the lens radial direction, it is possible to match the first and second zone profile zone radii at the radial direction boundary line of the partial overlapping region and the non-overlapping region.

Also, when partially overlapping the first and second zone profiles using the relationship of Equation 16 and Equation 17, it is possible to easily set matching zone radii on the boundary line of the overlapping regions. For example, by using the nth zone radius $r_n$ of the first zone profile expressed with Equation 6 and using a first zone diameter $r_1'$ expressed with Equation 7, it is possible to have a synchronous structure for which the $b \times \Omega$ number of zone pitches from the $(n+1)$th of the first zone profile and the $a \times \Omega$ number of zone pitches from the second of the second zone profiles be the same, and in relation to the diffractive structure of the first zone profile, the diffractive structure of the second zone profile can be synchronized and overlapped at either of the inner circumference edge part and the outer circumference edge part of the diffractive structure by the second zone profile.

By doing this, the inner circumference region up to the nth number of the diffractive structure by the first zone profile is made to be a non-overlapping region for which only the diffractive structure by the first zone profile is provided, and the zone region of the number $n+b \times \Omega$ from the number $n+1$ of the diffractive structure by the first zone profile is an overlapping region for which the diffractive structure by the first zone profile and the diffractive structure by the second zone profile are provided overlapping. Also, across the entirety of the non-overlapping region and the overlapping region, the diffractive structure by the first zone profile is provided having a designated Fresnel zone pitch continuously in the radial direction. In fact, the diffractive structure by the second zone profile is created by forming a diffractive structure that coexists connected synchronously with the zone of the diffractive structure by the first zone profile at the boundary part of the overlapping region and the non-overlapping region.

For the diffractive structure, at a specific region for which the lens aperture region is made to be the same (overlapping region), a plurality of different zone pitches determined by mutually different addition powers exist synchronously. Also, with this mode shown as an example, by providing the non-overlapping region and the overlapping region coexisting in the radial direction, for example as shown with the twenty-sixth mode, a plurality of focal points correlating to the respective addition powers according to the size of the pupil, for example, correlating to the lens aperture, are given to different regions of the diffractive lens, and it is possible to manifest this mode under specific conditions.

The twenty-seventh mode of the present invention relates to a method for manufacturing a diffractive multi-focal lens, and in particular, is a method for manufacturing a diffractive multi-focal lens having a diffractive structure comprising a plurality of zones in a concentric circle form, characterized by forming an overlapping region for which a first zone profile and a second zone profile are overlapped on the same region in at least a portion of the diffractive structure, the first zone profile having a zone pitch expressed by Equation 23 in at least a portion thereof and the second zone profile having a zone pitch expressed by Equation 24 in at least a portion thereof, and an addition power $P_1$ given by the first zone profile and an addition power $P_2$ given by the second zone profile being determined by a relational expression of Equation 25, where a and b are mutually different real numbers, and a value of a/b is a value that cannot be expressed by a natural number X or by 1/X.

$$r_n = \sqrt{r_1^2 + \frac{2\lambda(n-1)}{P_1}} \quad \text{[Equation 23]}$$

$\lambda$: Design wavelength
$r_n$: nth zone radius of the first zone profile
$r_1$: First zone radius of the first zone profile
$P_1$: Addition power of the first zone profile
m: Natural number $$r_m = \sqrt{r_1'^2 + \frac{2\lambda(m-1)}{P_2}} \quad \text{[Equation 24]}$$

$\lambda$: Design wavelength
$r_m$: mth zone radius of the second zone profile
$r_1'$: First zone radius of the second zone profile
$P_2$: Addition power of the second zone profile
n: Natural number $$P_2 = \frac{a}{b} \times P_1 \quad \text{[Equation 25]}$$

Also, the method of the present invention provides a method that is able to advantageously manufacture the diffractive multi-focal lens as noted in the first to twenty-sixth modes described above. In particular in accordance with the method of the present invention, based on the new knowledge that it is possible to more greatly expand the synchronous conditions in relation to one zone which was limited with the inventions noted in Patent Document 1 applied for previously, by setting the mutually overlapping first zone profile and second zone profile with essentially a Fresnel zone having a specific relative relationship considering the addition powers $P_1$ and $P_2$ to be set, it is possible to have a high degree of freedom of design while ensuring good positional accuracy for setting the position of the intermediate focal point, and it is possible to provide a diffractive multi-focal lens with three focal points as described previously constituted according to the present invention.

The twenty-eighth mode of the present invention is the method for manufacturing the diffractive multi-focal lens according to the twenty-seventh mode, wherein a and b in Equation 25 are mutually different integers of zero or greater, and are set so that quotients when a and b are divided by a mutual greatest common divisor thereof are both an integer other than 1.

By following this mode, it is possible to constitute a composite profile comprising the first zone profile and the second zone profile using a zone that has a periodically repeated structure, and possible to provide a diffractive multi-focal lens which is possible to manufacture even more efficiently while having a high degree of freedom of design and ensuring good positional accuracy for the position of the intermediate focal point.

Furthermore, the twenty-ninth mode of the present invention is the method of manufacturing the diffractive multi-focal lens according to the twenty-seventh or twenty-eighth mode, wherein a and b in Equation 25 are set to values that satisfy a relationship of a/b>1/2.

By following this mode, by setting a relationship for which the addition power $P_2$ by the second zone profile in relation to the addition power $P_1$ by the first zone profile is $P_2 > P_1 \times (1/2)$, it is possible to set the focal point set at the position between far and near even closer to the near focal point, and for example with the ophthalmic lens, it is possible to set focal points at a position suitable for viewing a personal computer screen when the near vision is used for reading.

The thirtieth mode of the present invention is the method for manufacturing the diffractive multi-focal lens according to any of the twenty-seventh to twenty-ninth modes, wherein by adjusting at least one of a phase constant and a phase shift for at least one of the first zone profile and the second zone profile that are overlapped with each other, an intensity distribution in an optical axis direction is adjusted and set.

By following this mode, it is possible to relatively adjust and set the light intensity of each focal point of the diffractive multi-focal lens. Specifically, it is possible to suitably and easily adjust and set the relative light intensity levels either estimating in advance or changing after the fact between the plurality of focal points generated by overlapping the plurality of zone profiles.

The thirty-first mode of the present invention is the method for manufacturing the diffractive multi-focal lens according to the thirtieth mode, wherein the at least one of the phase constant and the phase shift for the zone profile is adjusted to be mutually different between regions in a lens radial direction in the zone profile.

If this mode is followed, it is possible to adjust the ratio of the light intensity of each focal point for each designated region of the lens radial direction, and for example it is also possible to adjust and set the light intensity peak ratio of each focal point to be different according to the effective diameter of the lens or the like.

Effect of the Invention

As is clear from the description above, in accordance with the present invention, the degree of freedom of design for the focal point position is ensured to be greater than with the diffractive multi-focal lens of the background art structure, and because of that, for example with an ophthalmic lens or the like, when setting three focal points of near, intermediate, and far, it is also possible to set the position of the intermediate position focal point with a high degree of freedom.

Also, when deemed necessary, considering the lens aperture diameter changes of the pupil diameter of the wearer or the like with an ophthalmic lens, by setting the lens radial direction position or size or the like of the overlapping region of the first and second zone profiles, it is also possible to make the light intensity ratio or the intensity distribution variable as desired in the lens optical axis direction including the intermediate focal point according to the use environment or the like. It is possible to use effectively this kind of technical effect as necessary, and it does not absolutely have to be attained with the present invention.

BRIEF DESCRIPTION OF THE DRAWINGS

FIG. 2E is a graph using the phase shift τ to show the status when the blaze is shifted in the φ axis direction in relation to the reference line.

FIGS. 3A-3C are graphs for describing the relative relationship of each phase function for profiles (1) and (2) and the composite profile generated by overlapping those.

FIG. 4C shows as a composite profile the phase profile for the diffractive structure for which the two zones of the first zone profile shown in FIG. 4A are synchronized and overlapped with one zone of the second zone profile shown in FIG. 4B, and the intensity distribution in the optical axis direction is shown in FIG. 4D.

FIGS. 5A-5D show graphs relating to the diffractive multi-focal lens of the background art structure provided based on the invention noted in Patent Document 1, where FIG. 5C shows a composite profile for the diffractive structure for which the three zones of the first zone profile shown in FIG. 5A are synchronized and overlapped with one zone of the second zone profile shown in FIG. 5B, and the intensity distribution in the optical axis direction is shown in FIG. 5D.

FIGS. 6A-6E are drawings relating to the diffractive multi-focal lens as example 1 of the present invention, where FIGS. 6A and 6B show each phase profile of profiles (1) and (2) as the first and second zone profiles, FIG. 6C shows the composite profile as the overlapped phase profiles, FIG. 6D is a graph showing the intensity distribution in the optical axis direction of the diffractive structure constituted by overlapping, and FIG. 6E is a graph showing the intensity distribution in the optical axis direction for the aperture diameter of the first to twelfth zone regions of the diffractive structure.

FIGS. 7A and 7B show each phase profile of profiles (1) and (2) as the first and second zone profiles, FIG. 7C shows the composite profile as the overlapped phase profiles, and FIG. 7D is a graph showing the intensity distribution in the optical axis direction of the diffractive structure constituted by overlapping.

FIGS. 8A and 8B show each phase profile of profiles (1) and (2) as the first and second zone profiles, FIG. 8C shows the composite profile as the overlapped phase profiles, and FIG. 8D is a graph showing the intensity distribution in the optical axis direction of the diffractive structure constituted by overlapping.

FIGS. 9A and 9B show each phase profile of profiles (1) and (2) as the first and second zone profiles, FIG. 9C shows the composite profile as the overlapped phase profiles, and FIG. 9D is a graph showing the intensity distribution in the optical axis direction of the diffractive structure constituted by overlapping.

FIGS. 10A-10E are drawings relating to the diffractive multi-focal lens as example 5 of the present invention, where FIGS. 10A and 10B show each phase profile of profiles (1) and (2) as the first and second zone profiles, FIG. 10C shows the composite profile as the overlapped phase profiles, and FIG. 10D is a graph showing the intensity distribution in the optical axis direction of the diffractive structure constituted by overlapping. FIG. 10E is a graph showing the intensity distribution in the optical axis direction for the aperture diameter of the first to fourteenth zone regions of the diffractive structure constituted by overlapping.

FIGS. 11A and 11B show each phase profile of profiles (1) and (2) as the first and second zone profiles, FIG. 11C shows the composite profile as the overlapped phase profiles, and FIG. 11D is a graph showing the intensity distribution in the optical axis direction of the diffractive structure constituted by overlapping.

FIGS. 12A and 12B show each phase profile of profiles (1) and (2) as the first and second zone profiles, FIG. 12C shows the composite profile as the overlapped phase profiles, and FIG. 12D is a graph showing the intensity distribution in the optical axis direction of the diffractive structure constituted by overlapping.

FIG. 13A shows each phase profile of profiles (1) and (2) as the first zone profile and second zone profile, FIG. 13B shows the composite profile as the overlapped phase profiles, and FIG. 13C is a graph showing the intensity distribution in the optical axis direction of the diffractive structure constituted by overlapping.

FIGS. 14A-14C are drawings relating to the diffractive multi-focal lens as example 9 of the present invention, where FIG. 14A shows each phase profile of profiles (1) and (2) as the first zone profile and second zone profile, FIG. 14B shows the composite profile as the overlapped phase profiles, and FIG. 14C is a graph showing the intensity distribution in the optical axis direction of the diffractive structure constituted by overlapping.

FIGS. 15A-15E are drawings relating to the diffractive multi-focal lens as example 10 of the present invention, where FIGS. 15A and 15B show each phase profile of profiles (1) and (2) as the first and second zone profiles, FIG. 15C shows the composite profile as the overlapped phase profiles, and FIG. 15D is a graph showing the intensity distribution in the optical axis direction of the diffractive structure constituted by overlapping. FIG. 15E shows the intensity distribution in the optical axis direction of profile (2) as a reference drawing.

FIGS. 16A and 16B show each phase profile of profiles (1) and (2) as the first and second zone profiles, FIG. 16C shows the composite profile as the overlapped phase profiles, and FIG. 16D is a graph showing the intensity distribution in the optical axis direction of the diffractive structure constituted by overlapping.

FIGS. 17A and 17B show each phase profile of profiles (1) and (2) as the first and second zone profiles, FIG. 17C shows the composite profile as the overlapped phase profiles, and FIG. 17D is a graph showing the intensity distribution in the optical axis direction of the diffractive structure constituted by overlapping.

FIGS. 18A and 18B show each phase profile of profiles (1) and (2) as the first and second zone profiles, FIG. 18C shows the composite profile as the overlapped phase profiles, and FIG. 18D is a graph showing the intensity distribution in the optical axis direction of the first to sixth zone regions with the first zone profile which are non-overlapping regions. FIG. 18E is a graph showing the intensity distribution in the optical axis direction of the region also including overlapping regions.

FIGS. 19A-19E are drawings relating to the diffractive multi-focal lens as example 14 of the present invention, where FIGS. 19A and 19B show each phase profile of profiles (1) and (2) as the first and second zone profiles, FIG. 19C shows the composite profile as the overlapped phase profiles, and FIG. 19D is a graph showing the intensity distribution in the optical axis direction of the first to fifth zone regions with the first zone profile which are non-overlapping regions. FIG. 19E is a graph showing the intensity distribution in the optical axis direction of the region also including overlapping regions.

FIGS. 20A and 20B show each phase profile of profiles (1) and (2) as the first and second zone profiles, FIG. 20C shows the composite profile as the overlapped phase profiles, and FIG. 20D is a graph showing the intensity distribution in the optical axis direction of the diffractive structure constituted by overlapping.

FIGS. 21A-21E are drawings relating to the diffractive multi-focal lens as example 16 of the present invention, where FIGS. 21A, 21B and 21C show the respective phase profile of profiles (1), (2) and (3) as the first, second and third zone profiles, FIG. 21D shows the composite profile as the overlapped phase profiles, and FIG. 21E is a graph showing the intensity distribution in the optical axis direction of the diffractive structure constituted by overlapping.

FIGS. 22A-22E are drawings relating to the diffractive multi-focal lens as example 17 of the present invention, where FIGS. 22A, 22B and 22C show the respective phase profile of profiles (1), (2) and (3) as the first, second and third zone profiles, FIG. 22D shows the composite profile as the overlapped phase profiles, and FIG. 22E is a graph showing the intensity distribution in the optical axis direction of the diffractive structure constituted by overlapping.

FIGS. 23A-23E are drawings relating to the diffractive multi-focal lens as example 18 of the present invention, where FIGS. 23A, 23B and 23C show the respective phase profile of profiles (1), (2) and (3) as the first, second and third zone profiles, FIG. 23D shows the composite profile as the overlapped phase profiles, and FIG. 23E is a graph showing the intensity distribution in the optical axis direction of the diffractive structure constituted by overlapping.

FIGS. 24A-24E are drawings relating to the diffractive multi-focal lens as example 19 of the present invention, where FIGS. 24A, 24B and 24C show the respective phase profile of profiles (1), (2) and (3) as the first, second and third zone profiles, FIG. 24D shows the composite profile as the overlapped phase profiles, and FIG. 24E is a graph showing the intensity distribution in the optical axis direction of the diffractive structure constituted by overlapping.

FIGS. 25A-25E are drawings relating to the diffractive multi-focal lens as example 20 of the present invention, where FIGS. 25A, 25B and 25C show the respective phase profile of profiles (1), (2) and (3) as the first, second and third zone profiles, FIG. 25D shows the composite profile as the overlapped phase profiles, and FIG. 25E is a graph showing the intensity distribution in the optical axis direction of the diffractive structure constituted by overlapping.

FIGS. 26A-26F are drawings relating to the diffractive multi-focal lens as example 21 of the present invention, where FIGS. 26A, 26B, 26C and 26D show the respective phase profile of profiles (1), (2), (3) and (4) as the first, second, third and fourth zone profiles, FIG. 26E shows the overlapped and synthesized phase profiles, and FIG. 26F is a graph showing the intensity distribution in the optical axis direction of the diffractive structure constituted by overlapping.

FIGS. 27A-27F are drawings relating to the diffractive multi-focal lens as example 22 of the present invention, where FIGS. 27A, 27B, 27C and 27D show the respective phase profile of profiles (1), (2), (3) and (4) as the first, second, third and fourth zone profiles, FIG. 27E shows the overlapped and synthesized phase profiles, and FIG. 27F is a graph showing the intensity distribution in the optical axis direction of the diffractive structure constituted by overlapping.

FIGS. 28A-28G are drawings relating to the diffractive multi-focal lens as example 23 of the present invention, where FIGS. 28A, 28B, 28C, 28D and 28E show the respective phase profile of profiles (1), (2), (3), (4) and (5) as the first, second, third, fourth and fifth zone profiles, FIG. 28F shows the overlapped and synthesized phase profiles, and FIG. 28G is a graph showing the intensity distribution in the optical axis direction of the diffractive structure constituted by overlapping.

FIGS. 29A-29D are drawings relating to the diffractive multi-focal lens as example 24 of the present invention, where FIGS. 29A, 29B, 29C and 29D are graphs showing the intensity distribution in the optical axis direction of the diffractive structure constituted by combining and overlapping the first zone profile and second zone profile of example 6 with different phase constants.

FIG. 30A shows the composite profile as overlapped phase profiles when the regions are changed to vary the phase constants of the first zone profile and the second zone profile of example 6, and FIGS. 30B and 30C are graphs showing the intensity distribution in the optical axis direction of the diffractive structure in the opening range of aperture diameter A and aperture diameter B.

EMBODIMENTS FOR CARRYING OUT THE INVENTION

Figure 1:
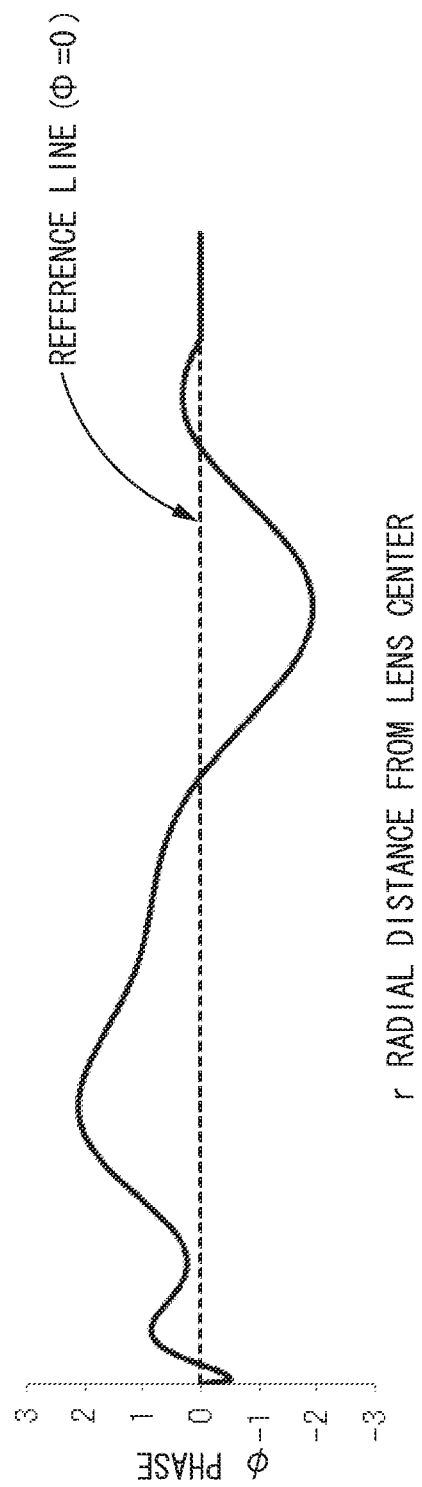
FIG. 1 is a graph of the phase function with the r-φ coordinate system expressing the relationship of the phase φ of the phase modulation structure provided in the diffractive lens with the lens radial direction position r.
Figure 2A:
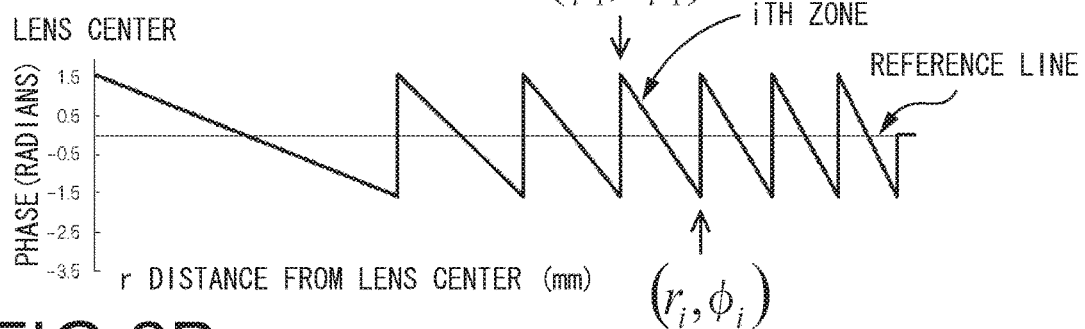
FIGS. 2A-2E show graphs with FIGS. 2A, 2B, 2C, and 2D respectively showing the blaze as one mode of the phase function for the diffractive lens.
Figure 2B:
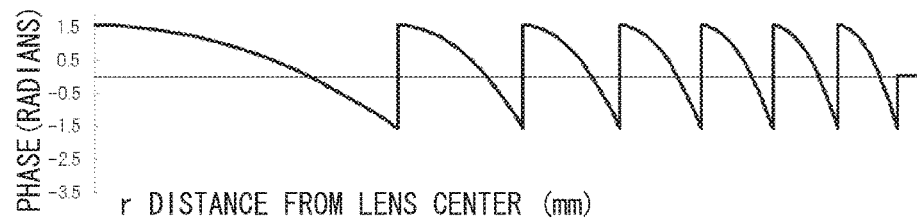
Figure 2C:
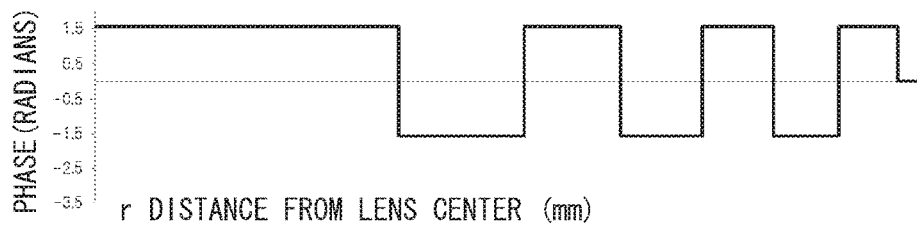
Figure 2D:
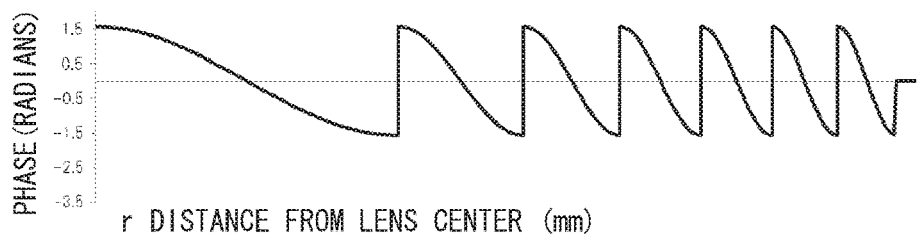
Figure 2E:
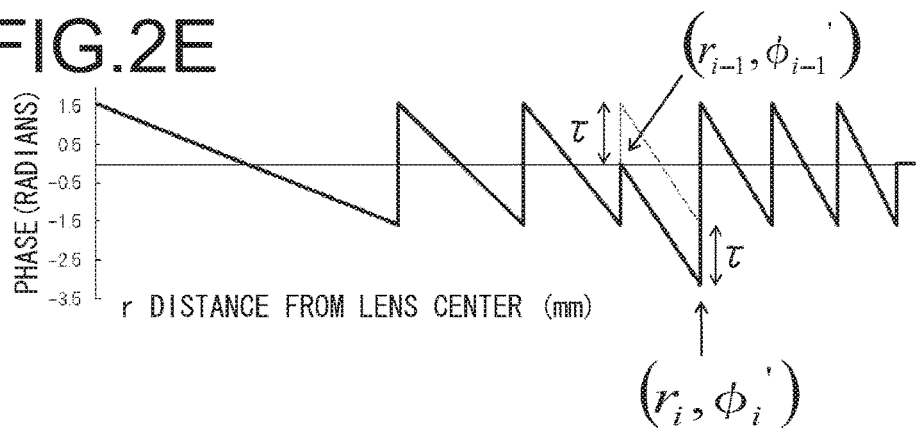
Figure 4A:
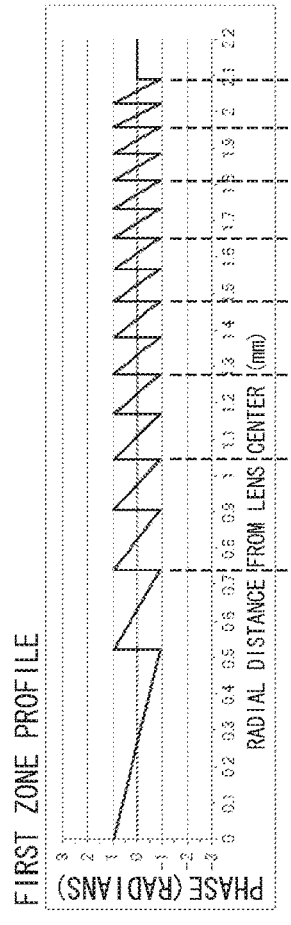
FIGS. 4A-4D show graphs relating to the diffractive multi-focal lens of the background art structure provided based on the inventions noted in Patent Documents 1 and 2, where
Figure 4B:
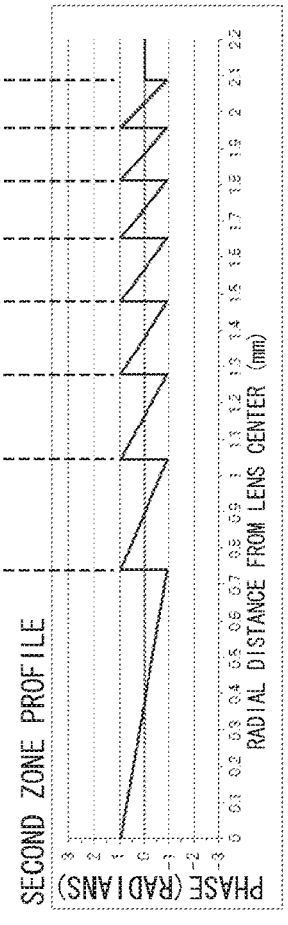
Figure 4C:
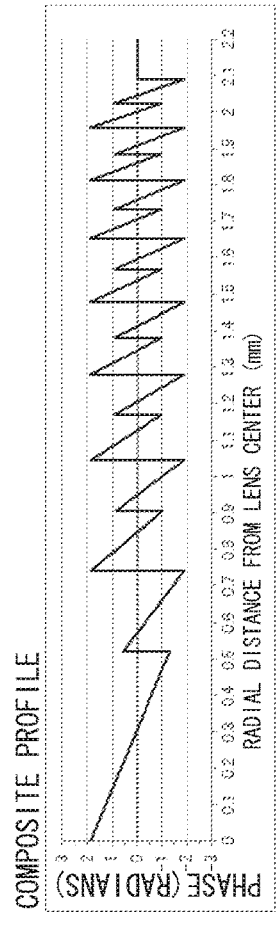
Figure 4D:
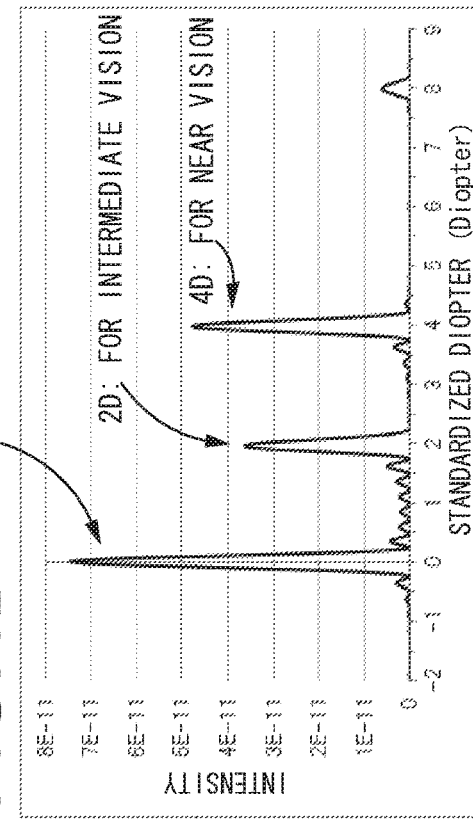

Following, by describing modes for carrying out the present invention, the present invention will be made clear in more specific terms.

Example Conditions and the Like

To start, we will describe the calculation simulation methods, conditions and the like used with the examples below. The calculation software was used that can calculate amplitude distribution and intensity distribution from each zone based on a diffraction integral equation derived from a theory known in the field called the scalar diffraction theory. Using this calculation software, we calculated the intensity distribution on the optical axis. A far point light source was set up as light source for calculation, and the calculation was performed on the assumption that parallel light beams in the same phase enter into the lens. Also, in the calculation, it was assumed that the media on the object and image sides are vacuum and the lens is an ideal lens having no aberration (light beams passing through the lens form an image at the same focal point regardless of the emitting position of the light). Further, the calculation was performed based on the assumption that the wavelength equals 546 nm and the refractive power of the lens for the 0th order diffracted light (basic refractive power) equals 7D (Diopter).

For the intensity distribution on the optical axis, the distance on the optical axis from the lens position as the base point to the image plane was converted to diopters, the focal point position of the 0th order diffracted light was standardized as 0 D, and intensity was plotted on that standardized scale. Unless otherwise noted, the lens aperture range for which the calculation simulation was performed was the region up to the zone number noted in each example.

In the examples using a blaze shaped phase, the mathematical formula for the blaze is based on Equation 3. In regards to the first, second, and so on zone profiles before synthesis (hereafter, these are called "starting profiles" or the like), unless otherwise noted, the phase shift in Equation 3 is zero, and the phase of the blaze is noted using the phase constant h of Equation 4. The phase of the composite profile is noted as $\phi i'$, $\phi i-1'$ as described previously.

Also, the phase profiles are set as being centrosymmetric to the lens, and the zone diameter in the tables and drawings noted in the examples are shown across the radial direction region from the center of the lens cross section. Furthermore, in the examples, the first, second, and so on zone profiles of the present invention are noted as profile (1), (2), and so on, and the phase profile for the overlapping region formed by overlapping of a plurality of zone profiles is noted as the composite profile.

Example 1

In the diffractive structure with a blaze shaped phase modulation, based on the previously described standard setting equations Equation 11 and Equation 12, the profile (1), for which the zone pitch is set so as to have the addition power $P_1$ be 4 diopters (hereafter, diopters are noted as D) and the profile (2), for which the zone pitch is set with a=3 and b=4 based on Equation 8 so that the addition power $P_2$ is 3 D which is ¾ the addition power of profile (1), are respectively prepared, and the composite profile was obtained by synthesizing the zone phase functions for both profiles. The details of the composite profile are shown in Table 1 and FIG. 6.

TABLE 1

[Example 1]

| Profile (1) Addition power $P_1$ = 4D | | | Profile (2) Addition power $P_2$ = 3D | | | Composite profile (Example 1) | | | | |
|---|---|---|---|---|---|---|---|---|---|---|
| Zone No. n | Zone radius (mm) $r_n$ | Phase Constant h | Zone No. m | Zone radius (mm) $r_m$ | Phase constant h | Zone No. i | Zone radius (mm) Outer radius $r_i$ | Zone radius (mm) Inner radius $r_{i-1}$ | Phase (radians) $\phi_i'$ | Phase (radians) $\phi_{i-1}'$ |
| 1 | 0.5225 | 0.4 | 1 | 0.6033 | 0.3 | 1 | 0.5225 | 0 | −1.9466 | 2.1991 |
| 2 | 0.7389 | 0.4 | 2 | 0.8532 | 0.3 | 2 | 0.6033 | 0.5225 | −0.6245 | 0.5667 |
| 3 | 0.9050 | 0.4 | 3 | 1.0450 | 0.3 | 3 | 0.7389 | 0.6033 | −1.3369 | 1.2605 |
| 4 | 1.0450 | 0.4 | 4 | 1.2066 | 0.3 | 4 | 0.8532 | 0.7389 | −1.4158 | 1.1764 |
| 5 | 1.1683 | 0.4 | 5 | 1.3491 | 0.3 | 5 | 0.9050 | 0.8532 | −0.8229 | 0.4691 |
| 6 | 1.2798 | 0.4 | 6 | 1.4778 | 0.3 | 6 | 1.0450 | 0.9050 | −2.1991 | 1.6904 |
| 7 | 1.3824 | 0.4 | 7 | 1.5962 | 0.3 | 7 | 1.1683 | 1.0460 | −1.7523 | 2.1991 |
| 8 | 1.4778 | 0.4 | 8 | 1.7065 | 0.3 | 8 | 1.2066 | 1.1683 | −0.5494 | 0.7609 |
| 9 | 1.5675 | 0.4 | 9 | 1.8100 | 0.3 | 9 | 1.2798 | 1.2066 | −1.2829 | 1.3355 |
| 10 | 1.6523 | 0.4 | | | | 10 | 1.3491 | 1.2798 | −1.3826 | 1.2304 |
| 11 | 1.7329 | 0.4 | | | | 11 | 1.3824 | 1.3491 | −0.8019 | 0.5024 |
| 12 | 1.8100 | 0.4 | | | | 12 | 1.4778 | 1.3824 | −2.1991 | 1.7114 |
| | | | | | | 13 | 1.5675 | 1.4778 | −1.7412 | 2.1991 |
| | | | | | | 14 | 1.5962 | 1.5675 | −0.5384 | 0.7720 |
| | | | | | | 15 | 1.6523 | 1.5962 | −1.2724 | 1.3465 |
| | | | | | | 16 | 1.7065 | 1.6523 | −1.3746 | 1.2409 |

TABLE 1-continued

[Example 1]

| | Profile (1) Addition power $P_1 = 4D$ | | | Profile (2) Addition power $P_2 = 3D$ | | | Composite profile (Example 1) | | | |
|---|---|---|---|---|---|---|---|---|---|---|
| | Zone radius | | | Zone radius | | | Zone radius (mm) | | Phase | |
| Zone No. n | (mm) $r_n$ | Constant h | Zone No. m | (mm) $r_m$ | constant h | Zone No. i | Outer radius $r_i$ | Inner radius $r_{i-1}$ | (radians) $\phi_i'$ | $\phi_{i-1}'$ |
| | | | | | | 17 | 1.7329 | 1.7065 | −0.7960 | 0.5104 |
| | | | | | | 18 | 1.8100 | 1.7329 | −2.1991 | 1.7173 |

This composite profile is obtained by overlapping and synthesizing the profile (1) up to the 12th zone and the profile (2) up to the 9th zone. The phase constant of profile (1) is set at a constant h=0.4 for all blazes, and a constant h=0.3 for all blazes for profile (2) as well. The profiles are shown in FIGS. 6A and 6B.

With this example, as can be understood from the relational expressions of Equation 16 and Equation 17, there is a synchronous structure for which the zone radii of profiles (1) and (2) that correspond to the zone numbers for which n=4Ω and m=3Ω respectively (L is a natural number) are matched, and for which four continuous zone pitches of profile (1) and three continuous zone pitches of profile (2) are the same. As a result, the composite profile for which these profiles are synthesized has six blazes newly formed in the synchronous region. Therefore, a structure is exhibited which has similar phase profiles repeated in zone units of the first to sixth, seventh to twelfth, thirteenth to eighteenth, and so on for the composite profile (hereafter called a repeated structure). When the zone numbers constituting the repeated structure are equally shifted (for example, shifted to the second to seventh, eighth to thirteenth, and fourteenth to nineteenth (the nineteenth is not shown in the table)), the profile shape distribution of the repeated structure is different from that before shifting but is similar among the structure units (FIG. 6C). The results of calculating the optical axis direction intensity distribution of the composite profile is shown in FIG. 6D.

From this intensity distribution diagram, we can see that peaks are generated at 0 D, 3 D, and 4 D. The peak generated at 0 D is based on the 0th order diffracted light of this composite profile, the 4 D peak is based on the +1 order diffracted light of profile (1), and the 3 D peak is based on the +1 order diffracted light of profile (2).

If the diffractive multi-focal lens comprising the composite profile of this example is used for an ophthalmic lens, for example, it is possible to use the 0 D peak as the focal point for far vision, the 4 D peak as the peak for the focal point for ensuring visual power in near regions, and the 3 D peak as the focal point for ensuring visual power in the intermediate regions between these. Also, when using this example as an intraocular lens that is inserted and fixed in the human eye, focal points are respectively generated at positions of approximately 35 cm in front for the 4 D power for near use, and approximately 45 to 50 cm in front for the 3 D power for intermediate use.

With the background art technology disclosed in Patent Documents 1 and 2, in comparison with this example, in contrast to the fact that the intermediate region focal point position is a maximum of ½ the addition power of profile (1), in other words, that it is only possible to set to a point of 4×(1/2)=2 D at a maximum, with this example, it is possible to set the intermediate focal point up to the 3 D point. It is possible to set the intermediate focal point to a nearer side than the setting position of the background art in this way, so for example with a patient who has an intraocular lens inserted, who does not have his own power of accommodation, it is possible to ensure a focal point at suitable positions from the reading position to the viewing position for a personal computer.

Also, with this example, profiles (1) and (2) are synthesized over the entire diffractive structure, so the same intensity distribution is realized in any aperture range (lens diameter region) of the diffractive structure. FIG. 6E shows the optical axis direction intensity distribution of the composite profile radius of approximately 1.48 mm (from zones 1 to 12), and shows the intensity ratio for far, intermediate, and near, which is similar to FIG. 6D. Therefore, it is especially effective as a multi-focal ophthalmic lens or the like for giving far, intermediate and near vision that is stable and is not dependent on changes in pupil size due to changes in the illumination environment, for example.

Example 2

Figure 7A:
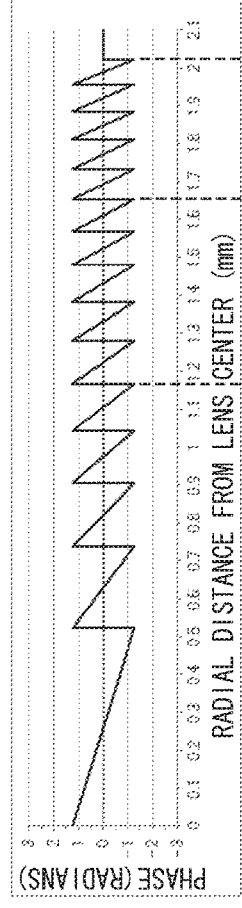
FIGS. 7A-7D are drawings relating to the diffractive multi-focal lens as example 2 of the present invention, where
Figure 7B:
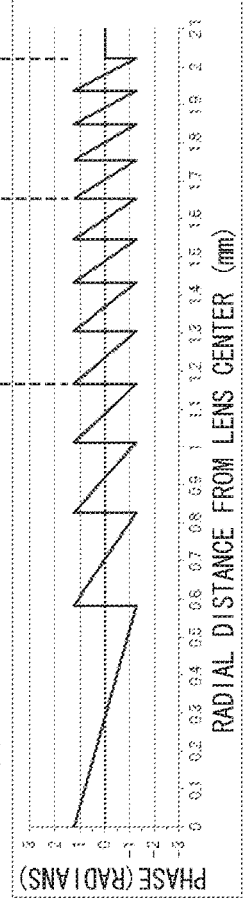

The same as with example 1, with a blaze shaped phase modulation type diffractive structure, using standard setting equations Equation 11 and Equation 12, two types of profiles were synthesized, for which the addition power $P_1$ of profile (1) is set to 4 D, and for which the addition power $P_2$ of profile (2) is set to $P_2$=4×(4/5)=3.2 D with a=4 and b=5 in Equation 8 so that it is 4/5 of the addition power of profile (1). The phase constants of profiles (1) and (2) are respectively set at h=0.4 and h=0.4 (FIGS. 7A and 7B). The details of the composite profile obtained by synthesizing the phase functions of profiles (1) and (2) are shown respectively in Table 2 and FIG. 7C.

TABLE 2

[Example 2]

| Profile (1) Addition power $P_1 = 4D$ | | | Profile (2) Addition power $P_2 = 3.2D$ | | | Composite profile (Example 2) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) | |
| | | | | | | | | | $\phi_i'$ | $\phi_{i-1}'$ |
| 1 | 0.5225 | 0.4 | 1 | 0.5842 | 0.4 | 1 | 0.5225 | 0 | −2.2479 | 2.5133 |
| 2 | 0.7389 | 0.4 | 2 | 0.8261 | 0.4 | 2 | 0.5842 | 0.5225 | −0.7162 | 0.2653 |
| 3 | 0.9050 | 0.4 | 3 | 1.0118 | 0.4 | 3 | 0.7389 | 0.5842 | −1.6074 | 1.7971 |
| 4 | 1.0450 | 0.4 | 4 | 1.1683 | 0.4 | 4 | 0.8261 | 0.7389 | −1.3199 | 0.9059 |
| 5 | 1.1683 | 0.4 | 5 | 1.3062 | 0.4 | 5 | 0.9050 | 0.8261 | −1.0673 | 1.1933 |
| 6 | 1.2798 | 0.4 | 6 | 1.4309 | 0.4 | 6 | 1.0118 | 0.9050 | −1.9176 | 1.4459 |
| 7 | 1.3824 | 0.4 | 7 | 1.5456 | 0.4 | 7 | 1.0450 | 1.0118 | −0.5328 | 0.5957 |
| 8 | 1.4778 | 0.4 | 8 | 1.6523 | 0.4 | 8 | 1.1683 | 1.0450 | −2.5133 | 1.9805 |
| 9 | 1.5675 | 0.4 | 9 | 1.7525 | 0.4 | 9 | 1.2798 | 1.1683 | −2.0323 | 2.5133 |
| 10 | 1.6523 | 0.4 | 10 | 1.8473 | 0.4 | 10 | 1.3062 | 1.2798 | −0.6468 | 0.4810 |
| 11 | 1.7329 | 0.4 | 11 | 1.9376 | 0.4 | 11 | 1.3824 | 1.3062 | −1.5362 | 1.8665 |
| 12 | 1.8100 | 0.4 | 12 | 2.0236 | 0.4 | 12 | 1.4309 | 1.3824 | −1.2776 | 0.9781 |
| 13 | 1.8839 | 0.4 | | | | 13 | 1.4778 | 1.4309 | −1.0287 | 1.2357 |
| 14 | 1.9550 | 0.4 | | | | 14 | 1.5456 | 1.4778 | −1.8986 | 1.4846 |
| 15 | 2.0236 | 0.4 | | | | 15 | 1.5675 | 1.5456 | −0.5163 | 0.6146 |
| | | | | | | 16 | 1.6623 | 1.5675 | −2.5133 | 1.9969 |
| | | | | | | 17 | 1.7329 | 1.6523 | −2.0222 | 2.5133 |
| | | | | | | 18 | 1.7525 | 1.7329 | −0.6387 | 0.4910 |
| | | | | | | 19 | 1.8100 | 1.7525 | −1.5238 | 1.8746 |
| | | | | | | 20 | 1.8473 | 1.8100 | −1.2692 | 0.9895 |
| | | | | | | 21 | 1.8839 | 1.8473 | −1.0197 | 1.2441 |
| | | | | | | 22 | 1.9375 | 1.8839 | −1.8936 | 1.4935 |
| | | | | | | 23 | 1.9550 | 1.9375 | −0.5115 | 0.6197 |
| | | | | | | 24 | 2.0236 | 1.9550 | −2.5133 | 2.0018 |

Figure 7D:
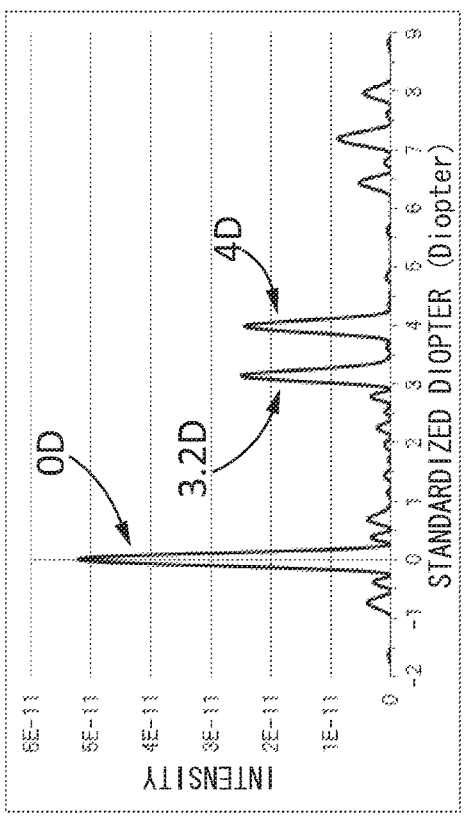
Figure 7C:
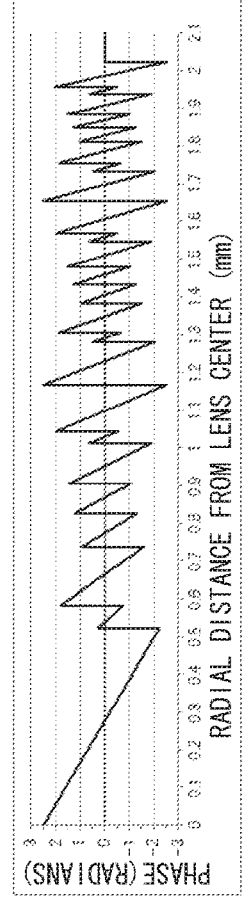

With this example, there is a synchronous structure for which the zone radii of profiles (1) and (2) are matched using the zone numbers for which n=5Ω and m=4Ω (Ω is a natural number), and for which five continuous zone pitches of profile (1) and four continuous zone pitches of profile (2) are the same. As a result, the composite profile for which these profiles are synthesized has eight blazes newly formed in the synchronous region. Therefore, a new repeated structure is formed at the first to eighth, ninth to sixteenth, and seventeenth to twenty-fourth zones with the composite profile. The results of calculating the optical axis direction intensity distribution of the composite profile are shown in FIG. 7D.

From this intensity distribution diagram, we can see that main peaks are generated at 0 D, 3.2 D, and 4 D. The peak generated at 0 D is based on the 0th order diffracted light of this composite profile, the 4 D peak is based on the +1 order diffracted light of profile (1), and the 3.2 D peak is based on the +1 order diffracted light of profile (2).

This example is an example in which the focal point position of the intermediate region is adjusted to be shifted further to the near side than with example 1. When used for an ophthalmic lens, for example, these are specifications particularly suited as a multi-focal ophthalmic lens that can be applied in cases of work while viewing a personal computer more closely.

Also, with this example as well, profiles (1) and (2) are synthesized over the entire diffractive structure, so the same as with example 1, the same intensity distribution is realized in any opening range of the diffractive structure.

Example 3

This example is an example for which the addition power $P_2$ of profile (2) is set to be (3/5) of the addition power $P_1$ of profile 1, and other than that, this was synthesized under the same conditions as example 2. With this example, the addition power of profile (2) is set as $P_2=4\times(3/5)=2.4$ D. The details of the composite provide are shown in Table 3 and FIG. 8C.

TABLE 3

[Example 3]

| | Profile (1) Addition power $P_1 = 4D$ | | | Profile (2) Addition power $P_2 = 2.4D$ | | | Composite profile (Example 3) | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.4 | 1 | 0.6745 | 0.4 | 1 | 0.5225 | 0 | −1.9468 | 2.5133 |
| 2 | 0.7389 | 0.4 | 2 | 0.9539 | 0.4 | 2 | 0.6745 | 0.5225 | −1.7656 | 0.5665 |
| 3 | 0.9050 | 0.4 | 3 | 1.1683 | 0.4 | 3 | 0.7389 | 0.6745 | −0.5791 | 0.7476 |
| 4 | 1.0450 | 0.4 | 4 | 1.3491 | 0.4 | 4 | 0.9050 | 0.7389 | −2.0729 | 1.9342 |
| 5 | 1.1683 | 0.4 | 5 | 1.5083 | 0.4 | 5 | 0.9539 | 0.9050 | −0.8788 | 0.4403 |
| 6 | 1.2798 | 0.4 | 6 | 1.6523 | 0.4 | 6 | 1.0450 | 0.9539 | −1.0673 | 1.6345 |
| 7 | 1.3824 | 0.4 | 7 | 1.7847 | 0.4 | 7 | 1.1683 | 1.0450 | −2.5133 | 1.4459 |
| 8 | 1.4778 | 0.4 | 8 | 1.9079 | 0.4 | 8 | 1.2798 | 1.1683 | −1.5506 | 2.5133 |
| 9 | 1.5675 | 0.4 | 9 | 2.0236 | 0.4 | 9 | 1.3491 | 1.2798 | −1.6967 | 0.9627 |
| 10 | 1.6523 | 0.4 | | | | 10 | 1.3824 | 1.3491 | −0.5258 | 0.8165 |
| 11 | 1.7329 | 0.4 | | | | 11 | 1.4778 | 1.3824 | −2.0323 | 1.9874 |
| 12 | 1.8100 | 0.4 | | | | 12 | 1.5083 | 1.4778 | −0.8544 | 0.4810 |
| 13 | 1.8839 | 0.4 | | | | 13 | 1.5675 | 1.5083 | −1.0330 | 1.6589 |
| 14 | 1.9550 | 0.4 | | | | 14 | 1.6523 | 1.5675 | −2.5133 | 1.4803 |
| 15 | 2.0236 | 0.4 | | | | 15 | 1.7329 | 1.6523 | −1.5310 | 2.5133 |
| | | | | | | 16 | 1.7847 | 1.7329 | −1.6876 | 0.9823 |
| | | | | | | 17 | 1.8100 | 1.7847 | −0.5163 | 0.8257 |
| | | | | | | 18 | 1.8839 | 1.8100 | −2.0238 | 1.9969 |
| | | | | | | 19 | 1.9079 | 1.8839 | −0.8482 | 0.4895 |
| | | | | | | 20 | 1.9550 | 1.9079 | −1.0232 | 1.6651 |
| | | | | | | 21 | 2.0236 | 1.9550 | −2.5133 | 1.4901 |

Figure 8A:
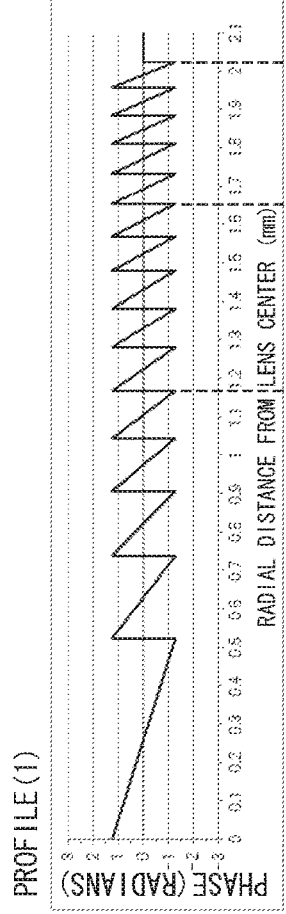
FIGS. 8A-8D are drawings relating to the diffractive multi-focal lens as example 3 of the present invention, where
Figure 8B:
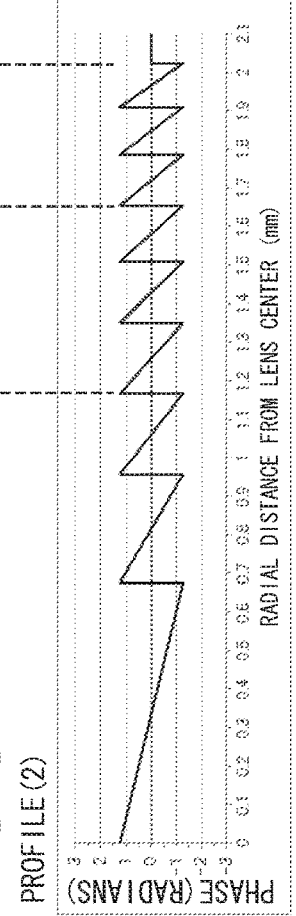
Figure 8C:
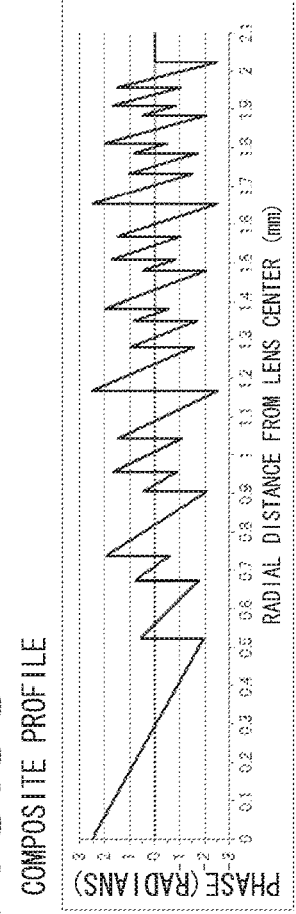
Figure 8D:
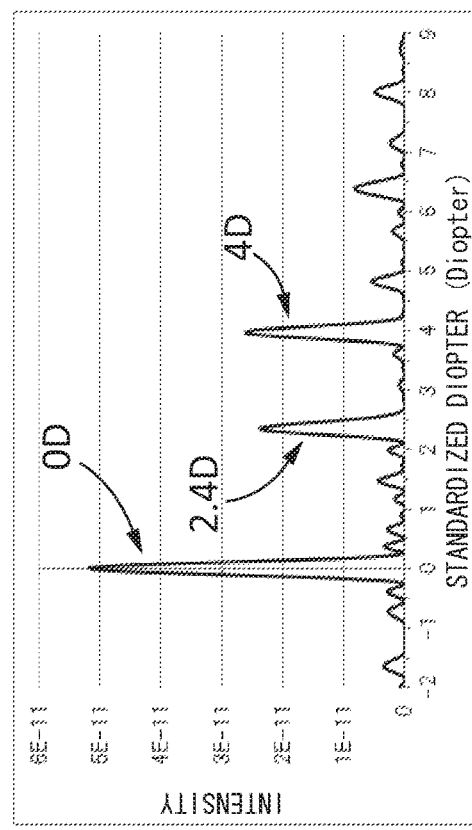

With this example, there is a synchronous structure for which the zone radii of profiles (1) and (2) are matched using the zone numbers for which n=5Ω and m=3Ω (Ω is a natural number), and for which five continuous zone pitches of profile (1) and three continuous zone pitches of profile (2) are the same (FIGS. 8A and 8B). As a result, the composite profile for which these profiles are synthesized has seven blazes newly formed in the synchronous region (FIG. 8C). Therefore, a new repeated structure is formed at the first to seventh, eighth to fourteenth, and fifteenth to twenty-first zone units with the composite profile. The results of calculating the optical axis direction intensity distribution of the composite profile are shown in FIG. 8D.

When the addition power of profile (2) was set as 2.4 D, the position of the intermediate focal point peak is generated a little farther from the near focal point position than with examples 1 and 2. By varying the addition power of profile (2) in this way, we can see that it is possible to freely set the intermediate focal point peak to any position.

Example 4

Other than the addition power $P_2$ of profile (2) of example 2 being made to be (2/5) of the addition power $P_1$ of profile (1), this is an example that obtains the composite profile with the same conditions as with example 2. With this example, the addition power of profile (2) is set as $P_2=4\times(2/5)=1.6$ D. Details of the composite profile are shown in Table 4 and FIG. 9C.

TABLE 4

[Example 4]

| | Profile (1) Addition power $P_1 = 4D$ | | | Profile (2) Addition power $P_2 = 1.6D$ | | | Composite profile (Example 4) | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.4 | 1 | 0.8261 | 0.4 | 1 | 0.5225 | 0 | −1.5895 | 2.5133 |
| 2 | 0.7389 | 0.4 | 2 | 1.1683 | 0.4 | 2 | 0.7389 | 0.5225 | −2.2479 | 0.9237 |
| 3 | 0.9050 | 0.4 | 3 | 1.4309 | 0.4 | 3 | 0.8261 | 0.7389 | −1.3199 | 0.2653 |
| 4 | 1.0450 | 0.4 | 4 | 1.6523 | 0.4 | 4 | 0.9050 | 0.8261 | −0.5791 | 1.1933 |
| 5 | 1.1683 | 0.4 | 5 | 1.8473 | 0.4 | 5 | 1.0450 | 0.9050 | −1.6074 | 1.9342 |
| 6 | 1.2798 | 0.4 | 6 | 2.0236 | 0.4 | 6 | 1.1683 | 1.0450 | −2.5133 | 0.9059 |
| 7 | 1.3824 | 0.4 | | | | 7 | 1.2798 | 1.1683 | −1.0673 | 2.5133 |
| 8 | 1.4778 | 0.4 | | | | 8 | 1.3824 | 1.2798 | −2.0489 | 1.4459 |

TABLE 4-continued

[Example 4]

| Profile (1) Addition power $P_1 = 4D$ | | | Profile (2) Addition power $P_2 = 1.6D$ | | | Composite profile (Example 4) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 9 | 1.5675 | 0.4 | | | | 9 | 1.4309 | 1.3824 | −1.2776 | 0.4644 |
| 10 | 1.6523 | 0.4 | | | | 10 | 1.4778 | 1.4309 | −0.5328 | 1.2357 |
| 11 | 1.7329 | 0.4 | | | | 11 | 1.5675 | 1.4778 | −1.5506 | 1.9805 |
| 12 | 1.8100 | 0.4 | | | | 12 | 1.6523 | 1.5675 | −2.5133 | 0.9627 |
| 13 | 1.8839 | 0.4 | | | | 13 | 1.7329 | 1.6523 | −1.0393 | 2.5133 |
| 14 | 1.9550 | 0.4 | | | | 14 | 1.8100 | 1.7329 | −2.0323 | 1.4740 |
| 15 | 2.0236 | 0.4 | | | | 15 | 1.8473 | 1.8100 | −1.2692 | 0.4810 |
| | | | | | | 16 | 1.8839 | 1.8473 | −0.5215 | 1.2441 |
| | | | | | | 17 | 1.9550 | 1.8839 | −1.5352 | 1.9918 |
| | | | | | | 18 | 2.0236 | 1.9550 | −2.5133 | 0.9781 |

Figure 9A:
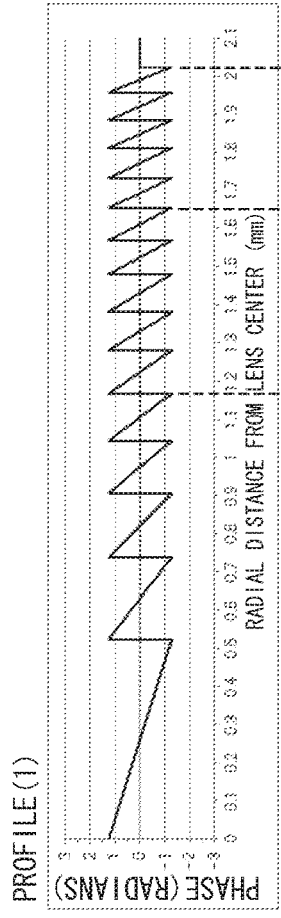
FIGS. 9A-9D are drawings relating to the diffractive multi-focal lens as example 4 of the present invention, where
Figure 9B:
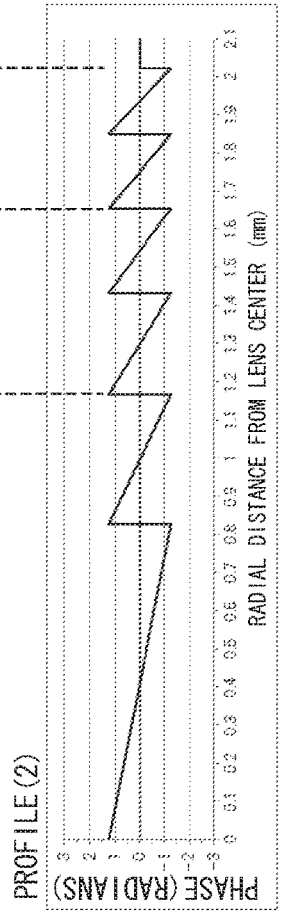
Figure 9C:
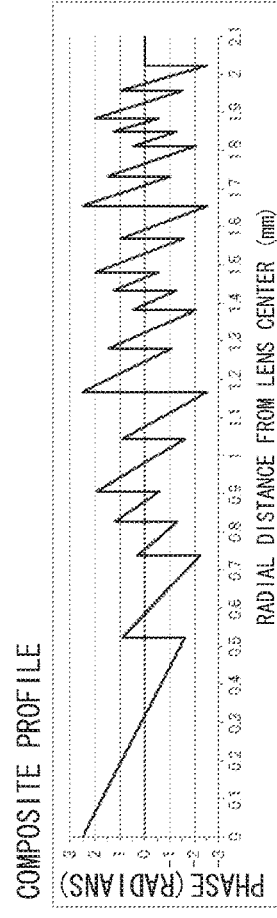
Figure 9D:
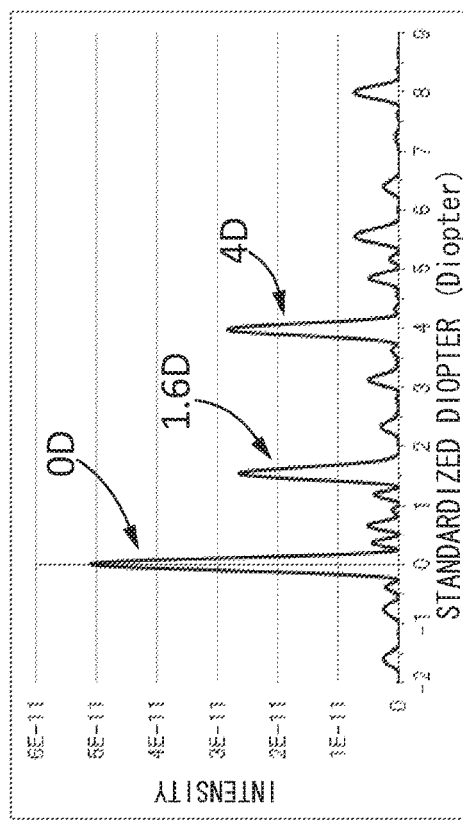

With this example, there is a synchronous structure for which the zone radii of profiles (1) and (2) are matched using the zone numbers for which n=5Ω and m=2Ω (Ω is a natural number), and for which five continuous zone pitches of profile (1) and two continuous zone pitches of profile (2) are the same (FIGS. 9A and 9B). As a result, the composite profile for which these profiles are synthesized has six blazes newly formed in the synchronous region (FIG. 9C). Therefore, a new repeated structure is formed at the first to sixth, seventh to twelfth, and thirteenth to eighteenth zone units with the composite profile. The results of calculating the optical axis direction intensity distribution of the composite profile are shown in FIG. 9D.

With this example, by using 1.6 D as the addition power of profile (2), we can see that a peak is generated at the intermediate point of approximately 1.6 D with the composite profile. The intermediate focal point position is set to be shifted to the farther side than with examples 1 to 3. This intermediate focal point position correlates to the focal point position for clearly visually recognizing trash or the like that has fallen on the floor or the like for users with a lot of work such as sweeping or the like. Therefore, this is a useful item as a multi-focal ophthalmic lens or the like for users with many opportunities to engage in this kind of housework or the like.

For the intermediate region focal point position shown with this example, with the background art noted in Patent Documents 1 and 2, the focal point position close to this could only be set to either $P_2=4\times(1/2)=2$ D or $P_2=4\times(1/3)=1.333$ D, but with this example, the addition power can be set as $P_2=4\times(2/5)=1.6$ D, so it is possible to set a finer level intermediate focal point.

Example 5

Other than the addition power $P_2$ of profile (2) of example 2 being made to be (7/11) of the addition power $P_1$ of profile (1), this is an example that obtains the composite profile with the same conditions as with example 2. Details of the composite profile are shown in Table 5 and FIG. 10C.

TABLE 5

[Example 5]

| Profile (1) Addition power $P_1 = 4D$ | | | Profile (2) Addition power $P_2 = 2.545D$ | | | Composite profile (Example 5) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.4 | 1 | 0.6550 | 0.4 | 1 | 0.5225 | 0 | −2.0049 | 2.5133 |
| 2 | 0.7389 | 0.4 | 2 | 0.9263 | 0.4 | 2 | 0.6550 | 0.5225 | −1.5385 | 0.5084 |
| 3 | 0.9050 | 0.4 | 3 | 1.1345 | 0.4 | 3 | 0.7389 | 0.6550 | −0.7776 | 0.9747 |
| 4 | 1.0450 | 0.4 | 4 | 1.3100 | 0.4 | 4 | 0.9050 | 0.7389 | −2.3160 | 1.7357 |
| 5 | 1.1683 | 0.4 | 5 | 1.4646 | 0.4 | 5 | 0.9263 | 0.9050 | −0.3823 | 0.1973 |
| 6 | 1.2798 | 0.4 | 6 | 1.6044 | 0.4 | 6 | 1.0450 | 0.9263 | −1.4331 | 2.1310 |
| 7 | 1.3824 | 0.4 | 7 | 1.7329 | 0.4 | 7 | 1.1345 | 1.0450 | −1.8231 | 1.0802 |
| 8 | 1.4778 | 0.4 | | | | 8 | 1.1683 | 1.1345 | −0.4851 | 0.6902 |
| 9 | 1.5675 | 0.4 | | | | 9 | 1.2798 | 1.1683 | −2.0820 | 2.0282 |
| 10 | 1.6523 | 0.4 | | | | 10 | 1.3100 | 1.2798 | −0.7382 | 0.4313 |
| 11 | 1.7329 | 0.4 | | | | 11 | 1.3824 | 1.3100 | −1.1773 | 1.7751 |
| | | | | | | 12 | 1.4646 | 1.3824 | −2.1643 | 1.3360 |
| | | | | | | 13 | 1.4778 | 1.4646 | −0.2383 | 0.3490 |

TABLE 5-continued

[Example 5]

| Profile (1) Addition power $P_1 = 4D$ | | | Profile (2) Addition power $P_2 = 2.545D$ | | | Composite profile (Example 5) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| | | | | | | 14 | 1.5675 | 1.4778 | −1.8501 | 2.2750 |
| | | | | | | 15 | 1.6044 | 1.5675 | −1.0934 | 0.6632 |
| | | | | | | 16 | 1.6523 | 1.6044 | −0.9365 | 1.4199 |
| | | | | | | 17 | 1.7329 | 1.6523 | −2.5133 | 1.5767 |

With this example, there is a synchronous structure for which the zone radii of profiles (1) and (2) are matched using the zone numbers for which n=11Ω and m=7Ω (Ω is a natural number), and for which eleven continuous zone pitches of profile (1) and seven continuous zone pitches of profile (2) are the same (FIGS. 10A and 10B). As a result, the composite profile for which these profiles are synthesized has seventeen blazes newly formed in the synchronous region (FIG. 10C). Therefore, a new repeated structure is formed at the first to seventeenth and eighteenth to thirty-fourth zone units with the composite profile (eighteenth to thirty-fourth items are not displayed). The results of calculating the optical axis direction intensity distribution of the composite profile are shown in FIG. 10D. With this example, the addition power of profile (2) is set as $P_2=4\times(7/11)=2.545$ D. In the intensity distribution diagram as well, we can clearly see that a peak is generated at that point (point of approximately 2.5 D).

Also, with this example, the composite profile repetition unit is 17 zones. FIG. 10D examines the intensity distribution of the repetition unit within one region (from the first to seventeenth zone numbers), but it is possible for the focal point peak to be generated at a position correlating to the addition power for which even one repetition unit is set (composite profile first to seventeenth regions), and we can see that a plurality of repetition units is not a required condition. Also, even if the repetition unit is one, all of the zones constituting that unit are not required, and for example FIG. 10E shows the intensity distribution of the regions from the first to the fourteenth within the repetition unit, but since a peak having the same intensity ratio is formed in the same position as FIG. 10D, it is acceptable for the zone constitution of at least a portion of the repetition unit to have a diffractive structure.

The examples in example 1 to example 5 noted above all have the zone radii of profiles (1) and (2) set based on the standard setting equations of Equation 11 and Equation 12, and show the specification and image characteristics of a composite profile having a structure for which a designated number of zones including the first zone are continuous and synchronized.

For examples of composite profiles when the synchronous structure position shifts to a different zone number, we will list and describe several examples.

[Example 6] (Example when the First Zone Radius is Changed to Change the Synchronous Position)

Figure 11A:
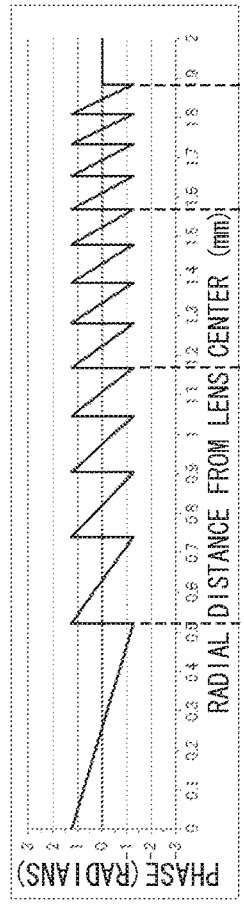
FIGS. 11A-11D are drawings relating to the diffractive multi-focal lens as example 6 of the present invention, where
Figure 11B:
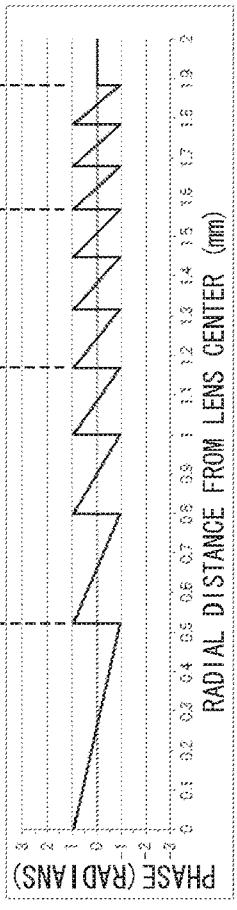
Figure 11C:
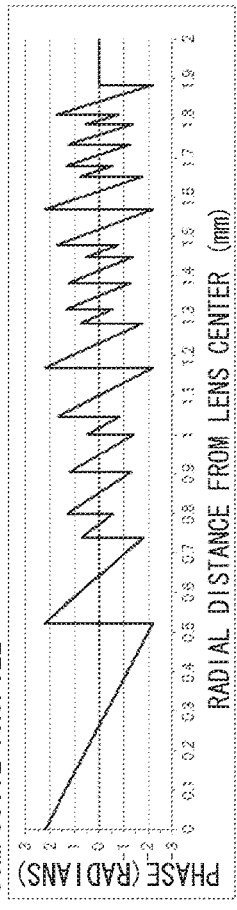

This example is an example that is the same as example 1 other than using the general setting equation noted above to change the zone pitch of profile (2). In specific terms, this shows a profile example for which the first zone radius $r_1'$ of profile (2) with the general setting equation of Equation 7 is the same as the first zone radius $r_1$ of profile (1), the zone pitch of profile (2) is reset, and this is overlapped with profile (1) and synthesized. Details of profiles (1) and (2) and the composite profile are respectively shown in Table 6 and FIGS. 11A, 11B, and 11C.

TABLE 6

[Example 6]

| Profile (1) Addition power $P_1 = 4D$ | | | Profile (2) Addition power $P_2 = 3D$ | | | Composite profile (Example 6) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.4 | 1 | 0.5225 | 0.3 | 1 | 0.5225 | 0 | −2.1991 | 2.1991 |
| 2 | 0.7389 | 0.4 | 2 | 0.7981 | 0.3 | 2 | 0.7389 | 0.5225 | −1.7942 | 2.1991 |

TABLE 6-continued

[Example 6]

| Profile (1) Addition power $P_1 = 4D$ | | | Profile (2) Addition power $P_2 = 3D$ | | | Composite profile (Example 6) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) | |
| | | | | | | | | | $\phi_i'$ | $\phi_{i-1}'$ |
| 3 | 0.9050 | 0.4 | 3 | 1.0005 | 0.3 | 3 | 0.7981 | 0.7389 | −0.5818 | 0.7190 |
| 4 | 1.0450 | 0.4 | 4 | 1.1683 | 0.3 | 4 | 0.9050 | 0.7981 | −1.3095 | 1.3031 |
| 5 | 1.1683 | 0.4 | 5 | 1.3149 | 0.3 | 5 | 1.0005 | 0.9050 | −1.4005 | 1.2038 |
| 6 | 1.2798 | 0.4 | 6 | 1.4467 | 0.3 | 6 | 1.0450 | 1.0005 | −0.8138 | 0.4845 |
| 7 | 1.3824 | 0.4 | 7 | 1.5675 | 0.3 | 7 | 1.1683 | 1.0450 | −2.1991 | 1.6995 |
| 8 | 1.4778 | 0.4 | 8 | 1.6796 | 0.3 | 8 | 1.2798 | 1.1683 | −1.7481 | 2.1991 |
| 9 | 1.5675 | 0.4 | 9 | 1.7847 | 0.3 | 9 | 1.3149 | 1.2798 | −0.5454 | 0.7651 |
| 10 | 1.6523 | 0.4 | 10 | 1.8839 | 0.3 | 10 | 1.3824 | 1.3149 | −1.2791 | 1.3396 |
| 11 | 1.7329 | 0.4 | | | | 11 | 1.4467 | 1.3824 | −1.3798 | 1.2342 |
| 12 | 1.8100 | 0.4 | | | | 12 | 1.4778 | 1.4467 | −0.7998 | 0.5052 |
| 13 | 1.8839 | 0.4 | | | | 13 | 1.5675 | 1.4778 | −2.1991 | 1.7134 |
| | | | | | | 14 | 1.6523 | 1.5675 | −1.7399 | 2.1991 |
| | | | | | | 15 | 1.6796 | 1.6523 | −0.5370 | 0.7734 |
| | | | | | | 16 | 1.7329 | 1.6796 | −1.2709 | 1.3479 |
| | | | | | | 17 | 1.7847 | 1.7329 | −1.3734 | 1.2423 |
| | | | | | | 18 | 1.8100 | 1.7847 | −0.7951 | 0.5115 |
| | | | | | | 19 | 1.8839 | 1.8100 | −2.1991 | 1.7182 |

The zone numbers for which the zone radii match between profile (2) and profile (1) that have been set and changed is n=1+4Ω with profile 1 and m=1+3Ω with profile (2) (Ω is a natural number).

Comparing this example and the composite profile of example 1 (FIG. 6C), the continuous zone count for each profile that made a synchronous structure and the number of zones contained in the synchronous structure are the same as example 1 and do not change, but the position of the repeated structure with the composite profile is different from example 1, and with this example, is changed to the second to seventh and the eighth to thirteenth. Even with that difference, the repeating unit structure with the composite profile is very similar, the intensity distribution does not differ from example 1, and we can see that it is possible to form the focal point peak at a position correlating to the addition power of profiles (1) and (2). An ophthalmic lens comprising the composite profile of this example, the same as the example details noted previously, is also particularly useful as a multi-focal ophthalmic lens such as for an intraocular lens or the like, for example.

In accordance with the first zone radius variable of profile (2), it is also acceptable to adjust the phase of the first zone blaze based on Equation 26 noted below. This adjustment can be used particularly effectively to improve the diffraction efficiency when the first zone radius is made smaller or the like.

$$\phi_0 = h \times \pi \times \left( \frac{P \times r_1^2}{\lambda} - 1 \right) \quad \text{[Equation 26]}$$

$\phi_0$: Phase of $r_0$ position h: Phase constant

P: Addition power $r_1$: 1st zone radius

λ: Wavelength

With the examples noted hereafter, even when the first zone radius is a variable, unless otherwise noted, as described with the definition of terms in [i] described previously, the phase of the first zone is set so as to be $|\phi_i|=|\phi_{i-1}|$.

[Example 7] (when the First Zone Radii of Both Profiles (1) and (2) are Varied)

Figure 12A:
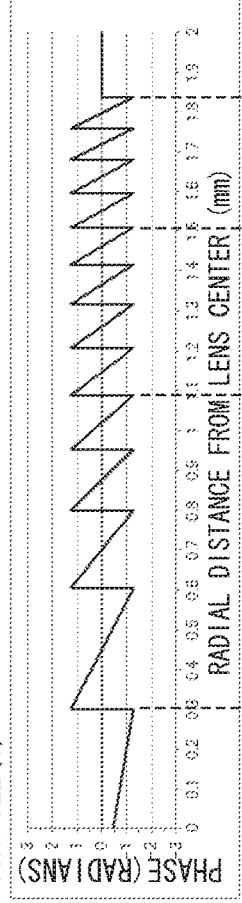
FIGS. 12A-12D are drawings relating to the diffractive multi-focal lens as example 7 of the present invention, where
Figure 12B:
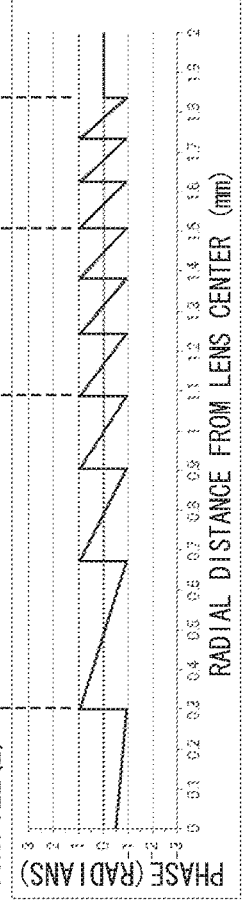
Figure 12C:
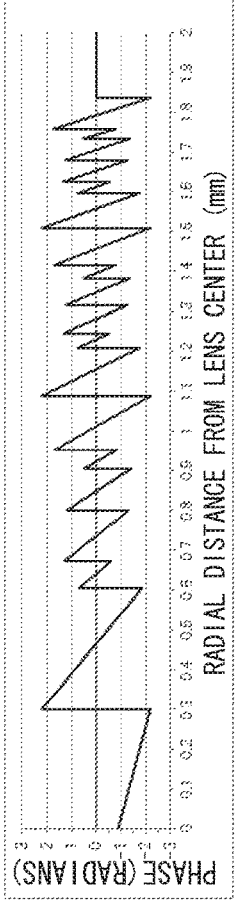

Next, we will show an example of a composite profile when the first zone radius of profiles (1) and (2) are varied, the first zone radii are set so that both of them are 0.3 mm, and the zone pitch of each profile is set. The addition power for both profiles (1) and (2) are set the same as for example 1, and the phase constant is also the same. However, only the first zone of each profile has the phase adjusted based on Equation 26. The zone pitches of profiles (1) and (2) have the first zone radius set to 0.3 mm and are respectively set based on general setting equations of Equation 6 and Equation 7. The details of profiles (1) and (2) and the composite profile are shown in Table 7 and FIGS. 12A, 12B, and 12C.

TABLE 7

[Example 7]

| Profile (1) Addition power $P_1 = 4D$ | | | Profile (2) Addition power $P_2 = 3D$ | | | Composite profile (Example 7) | | | | |
|---|---|---|---|---|---|---|---|---|---|---|
| | Zone radius | | | Zone radius | | | Zone radius (mm) | | Phase | |
| | | | | | | | | | (radians) | |
| Zone No. n | (mm) $r_n$ | Phase constant h | Zone No. m | (mm) $r_m$ | Phase constant h | Zone No. i | Outer radius $r_i$ | Inner radius $r_{i-1}$ | $\phi_i'$ | $\phi_{i-1}'$ |
| 1 | 0.3 | 0.4 | 1 | 0.3 | 0.3 | 1 | 0.3 | 0 | −2.1991 | −0.9045 |
| 2 | 0.6025 | 0.4 | 2 | 0.6738 | 0.3 | 2 | 0.6025 | 0.3 | −1.8396 | 2.1991 |
| 3 | 0.7975 | 0.4 | 3 | 0.9044 | 0.3 | 3 | 0.6738 | 0.6025 | −0.6048 | 0.6737 |
| 4 | 0.9534 | 0.4 | 4 | 1.0872 | 0.3 | 4 | 0.7975 | 0.6738 | −1.3251 | 1.2802 |
| 5 | 1.0872 | 0.4 | 5 | 1.2434 | 0.3 | 5 | 0.9044 | 0.7975 | −1.4096 | 1.1881 |
| 6 | 1.2062 | 0.4 | 6 | 1.3820 | 0.3 | 6 | 0.9534 | 0.9044 | −0.8193 | 0.4754 |
| 7 | 1.3145 | 0.4 | 7 | 1.5080 | 0.3 | 7 | 1.0872 | 0.9534 | −2.1991 | 1.6939 |
| 8 | 1.4146 | 0.4 | 8 | 1.6242 | 0.3 | 8 | 1.2062 | 1.0872 | −1.7508 | 2.1991 |
| 9 | 1.5080 | 0.4 | 9 | 1.7326 | 0.3 | 9 | 1.2434 | 1.2062 | −0.5479 | 0.7625 |
| 10 | 1.5959 | 0.4 | 10 | 1.8347 | 0.3 | 10 | 1.3145 | 1.2434 | −1.2815 | 1.3370 |
| 11 | 1.6793 | 0.4 | | | | 11 | 1.3820 | 1.3145 | −1.3816 | 1.2318 |
| 12 | 1.7587 | 0.4 | | | | 12 | 1.4146 | 1.3820 | −0.8011 | 0.5034 |
| 13 | 1.8347 | 0.4 | | | | 13 | 1.5080 | 1.4146 | −2.1991 | 1.7121 |
| | | | | | | 14 | 1.5959 | 1.5080 | −1.7407 | 2.1991 |
| | | | | | | 15 | 1.6242 | 1.5959 | −0.5379 | 0.7725 |
| | | | | | | 16 | 1.6793 | 1.6242 | −1.2719 | 1.3470 |
| | | | | | | 17 | 1.7326 | 1.6793 | −1.3742 | 1.2414 |
| | | | | | | 18 | 1.7587 | 1.7326 | −0.7957 | 0.5108 |
| | | | | | | 19 | 1.8347 | 1.7587 | −2.1991 | 1.7176 |

Figure 12D:
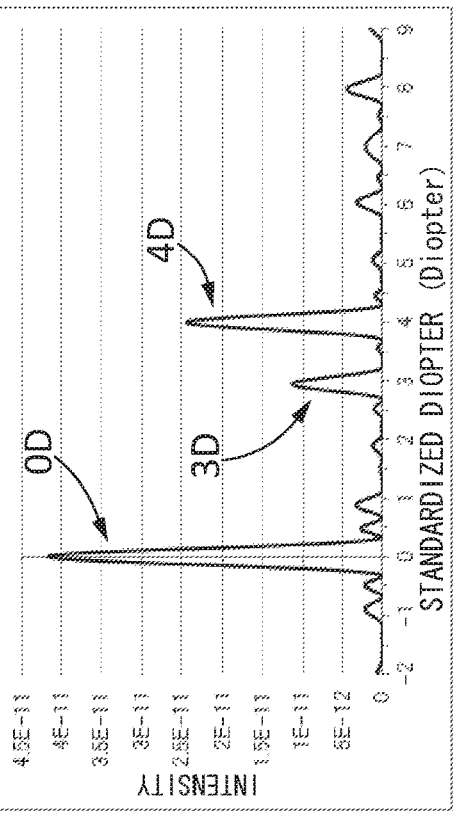

※Profile (1) Phase of 1st zone $\phi_1 = -1.2566$, $\phi_0 = -0.4281$
※Profile (2) Phase of 1st zone $\phi_1 = -0.9425$, $\phi_0 = -0.4764$ The profile of this example is set so that the first zone radius is 0.3 mm, and compared to example 1 and example 6, the first zone is set further to the inside. With this example, in accordance with the variation of the first zone radius for both profiles (1) and (2), the zone pitch of the entire region is different for examples 1 and 6, but there is no change in the synchronous zone count, and there is the same repeating unit as the previous examples. For the intensity distribution of the composite profile, we can see that the peak is formed at the point corresponding to the addition power determined by profiles (1) and (2) the same as for examples 1 and 6 as shown in FIG. 12D.

The diffractive type multi-focal lens for which this first zone radius is varied and the first zone is set to be further to the center can be suitably applied to an ophthalmic lens such as a contact lens, intraocular lens or the like, and for example is effective as a multi-focal ophthalmic lens such as an intraocular lens for patients for which the pupil diameter became smaller with aging, such as an older person or the like.

With examples 6 and 7, the examples have the first zone radius of profile (1) or (2) set freely using general setting equations Equation 6 and Equation 7. The zone pitch with the first zone radius changed based on the general setting equation is different from the zone pitch set with the standard setting equation, but if the addition power is the same, the synchronous zone count is the same as with example 1 and examples 6 and 7, and it is possible to obtain a multi-focal lens that can form focal points at positions corresponding to the addition power of each profile.

[Example 8] (Asynchronous Example)

In examples 6 and 7, we described examples of profiles for which the synchronous structure was maintained though the first zone radius of the structural profile was varied. This example shows an example that does not have a synchronous structure.

Figure 13A:
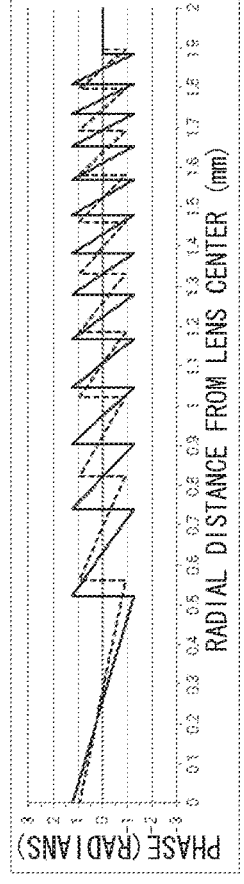
FIGS. 13A-13C are drawings relating to the diffractive multi-focal lens as example 8 of the present invention, where
Figure 13B:
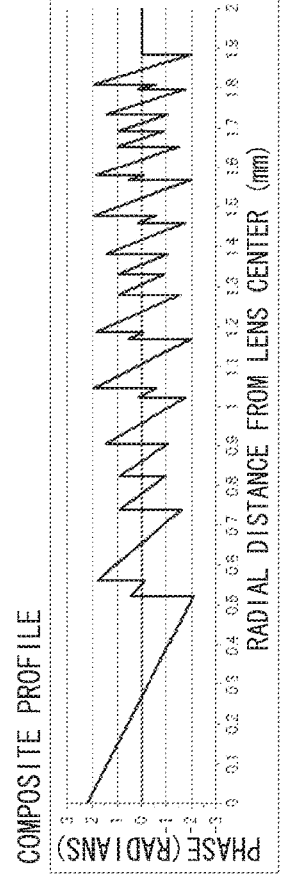

The addition power of profiles (1) and (2) and the zone pitch of profile (1) are the same as with example 1, and the zone pitch of profile (2) has the first zone radius set at 0.56 mm based on the general setting equation of Equation 7. The details of profiles (1) and (2) and the composite profile in this case are shown in Table 8 and FIGS. 13A and 13B.

TABLE 8

[Example 8]

| Profile (1) Addition power $P_1 = 4D$ | | | Profile (2) Addition power $P_2 = 3D$ | | | Composite profile (Example 8) | | | | |
|---|---|---|---|---|---|---|---|---|---|---|
| Zone | Zone radius (mm) | Phase | Zone | Zone radius (mm) | Phase | Zone | Zone radius (mm) | | Phase (radians) | |
| No. n | $r_n$ | constant h | No. m | $r_m$ | constant h | No. i | Outer radius $r_i$ | Inner radius $r_{i-1}$ | $\phi_i'$ | $\phi_{i-1}'$ |
| 1 | 0.5225 | 0.4 | 1 | 0.56 | 0.3 | 1 | 0.5225 | 0 | −2.0729 | 2.1991 |
| 2 | 0.7389 | 0.4 | 2 | 0.8232 | 0.3 | 2 | 0.56 | 0.5225 | −0.1214 | 0.4404 |
| 3 | 0.9050 | 0.4 | 3 | 1.0206 | 0.3 | 3 | 0.7389 | 0.56 | −1.5957 | 1.7636 |
| 4 | 1.0450 | 0.4 | 4 | 1.1856 | 0.3 | 4 | 0.8232 | 0.7389 | −0.9608 | 0.9176 |
| 5 | 1.1683 | 0.4 | 5 | 1.3303 | 0.3 | 5 | 0.9050 | 0.8232 | −1.0954 | 0.9241 |
| 6 | 1.2798 | 0.4 | 6 | 1.4607 | 0.3 | 6 | 1.0206 | 0.9050 | −1.7611 | 1.4179 |
| 7 | 1.3824 | 0.4 | 7 | 1.5304 | 0.3 | 7 | 1.0450 | 1.0206 | −0.5929 | 0.1239 |
| 8 | 1.4778 | 0.4 | 8 | 1.6916 | 0.3 | 8 | 1.1683 | 1.0450 | −2.0021 | 1.9204 |
| 9 | 1.5675 | 0.4 | 9 | 1.7960 | 0.3 | 9 | 1.1856 | 1.1683 | −0.0746 | 0.5112 |
| 10 | 1.6523 | 0.4 | 10 | 1.8946 | 0.3 | 10 | 1.2798 | 1.1856 | −1.5422 | 1.8104 |
| 11 | 1.7329 | 0.4 | | | | 11 | 1.3303 | 1.2798 | −0.9216 | 0.9710 |
| 12 | 1.8100 | 0.4 | | | | 12 | 1.3824 | 1.3303 | −1.0675 | 0.9634 |
| 13 | 1.8839 | 0.4 | | | | 13 | 1.4607 | 1.3824 | −1.7475 | 1.4457 |
| | | | | | | 14 | 1.4778 | 1.4607 | −0.5843 | 0.1375 |
| | | | | | | 15 | 1.5675 | 1.4778 | −1.9960 | 1.9290 |
| | | | | | | 16 | 1.5804 | 1.5675 | −0.0681 | 0.5173 |
| | | | | | | 17 | 1.6523 | 1.5804 | −1.5323 | 1.8168 |
| | | | | | | 18 | 1.6916 | 1.6523 | −0.9123 | 0.9810 |
| | | | | | | 19 | 1.7329 | 1.6916 | −1.0599 | 0.9726 |
| | | | | | | 20 | 1.7960 | 1.7329 | −1.7432 | 1.4534 |
| | | | | | | 21 | 1.8100 | 1.7960 | −0.5813 | 0.1417 |
| | | | | | | 22 | 1.8839 | 1.8100 | −1.9938 | 1.9320 |

Figure 13C:
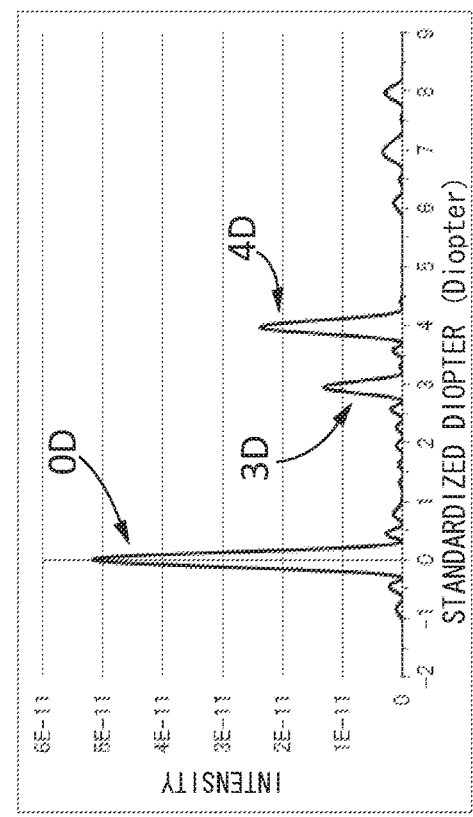

With FIG. 13, for profiles (1) and (2) different from the examples displayed in the diagrams up to now, both profiles are displayed simultaneously in the same drawing to clarify the zone diameter positional relationship. With this example, there is no location for which the zone diameter of either profile (1) or (2) is the same, and a synchronous structure is not formed. However, with the synthesized profile, a repeated structure is formed in the first to seventh, eighth to fourteenth, and fifteenth to twenty-first zone units, and the number of zones constituting the repeated structure is seven. With the composite profile of this example, though the repeated structure and the number of zones constituting it differ from those of examples 1, 6, and 7, the intensity distribution (FIG. 13C) can be seen to have a peak generated at a position correlating to the addition power set by profiles (1) and (2) the same as with the group of examples noted above.

As can be seen from this example, a synchronous structure with common regions is not a required condition, and it is possible to obtain a diffractive multi-focal lens that forms focal points at desired positions even without each profile that is overlapped having a synchronous structure with common regions. It is possible to further expand the degree of freedom of design with examples that do not have a synchronous structure, and when using it as an ophthalmic lens, there is a great advantage when designing a multi-focal ophthalmic lens according to the demands of a wider variety of users.

[Example 9] (Example of Synthesis when the Addition Power is Expressed Using an Irrational Number)

With example 8, we described the fact that there are composite profiles for which it is possible to set the desired focal points even when the zone diameters do not match. From this example as well, it is also conceivable that it is possible to generate focal points at desired positions even with a combination for which the ratio of the addition power of profiles (1) and (2) are not in an integral ratio relationship. This example 9 shows an example of a composite profile for which the addition power of profile (1) is left as is at 4 D, and the zone pitch of profile (2) is set based on the standard setting equation of Equation 12 so that the addition power of profile (2) is a multiple of $1/\sqrt{(2)}$ in relation to that of profile (1) (approximately 2.828 D). The phase constant of profile (2) was set as h=0.4. The details of each profile and the composite profile are shown in Table 9 and FIGS. 14A and 14B.

TABLE 9

[Example 9]

| Profile (1) Addition power $P_1 = 4D$ | | | Profile (2) Addition power $P_2 = 2.828D$ | | | Composite profile (Example 9) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.4 | 1 | 0.6214 | 0.4 | 1 | 0.5225 | 0 | −2.1134 | 2.5133 |
| 2 | 0.7389 | 0.4 | 2 | 0.8787 | 0.4 | 2 | 0.6214 | 0.5225 | −1.1480 | 0.3999 |
| 3 | 0.9050 | 0.4 | 3 | 1.0762 | 0.4 | 3 | 0.7389 | 0.6214 | −1.1480 | 1.3652 |
| 4 | 1.0450 | 0.4 | 4 | 1.2427 | 0.4 | 4 | 0.8787 | 0.7389 | −2.1159 | 1.3652 |
| 5 | 1.1683 | 0.4 | 5 | 1.3894 | 0.4 | 5 | 0.9050 | 0.8787 | −0.3342 | 0.3974 |
| 6 | 1.2798 | 0.4 | 6 | 1.5220 | 0.4 | 6 | 1.0450 | 0.9050 | −2.1159 | 2.1791 |
| 7 | 1.3824 | 0.4 | 7 | 1.6439 | 0.4 | 7 | 1.0762 | 1.0450 | −0.6363 | 0.3974 |
| 8 | 1.4778 | 0.4 | 8 | 1.7575 | 0.4 | 8 | 1.1683 | 1.0762 | −1.3905 | 1.8770 |
| 9 | 1.5675 | 0.4 | 9 | 1.8641 | 0.4 | 9 | 1.2427 | 1.1683 | −1.6763 | 1.1227 |
| 10 | 1.6523 | 0.4 | 10 | 1.9649 | 0.4 | 10 | 1.2798 | 1.2427 | −0.6363 | 0.8370 |
| 11 | 1.7329 | 0.4 | 11 | 2.0608 | 0.4 | 11 | 1.3824 | 1.2798 | −2.3933 | 1.8770 |
| 12 | 1.8100 | 0.4 | | | | 12 | 1.3894 | 1.3824 | −0.1843 | 0.1199 |
| 13 | 1.8839 | 0.4 | | | | 13 | 1.4778 | 1.3894 | −1.6763 | 2.3290 |
| 14 | 1.9550 | 0.4 | | | | 14 | 1.5220 | 1.4778 | −1.2381 | 0.8370 |
| 15 | 2.0236 | 0.4 | | | | 15 | 1.5675 | 1.5220 | −0.9374 | 1.2751 |
| | | | | | | 16 | 1.6439 | 1.5675 | −2.2665 | 1.5759 |
| | | | | | | 17 | 1.6523 | 1.6439 | −0.1843 | 0.2467 |
| | | | | | | 18 | 1.7329 | 1.6523 | −1.9700 | 2.3290 |
| | | | | | | 19 | 1.7575 | 1.7329 | −0.8003 | 0.5433 |
| | | | | | | 20 | 1.8100 | 1.7575 | −1.2381 | 1.7130 |
| | | | | | | 21 | 1.8641 | 1.8100 | −1.8393 | 1.2751 |
| | | | | | | 22 | 1.8839 | 1.8641 | −0.4940 | 0.6739 |
| | | | | | | 23 | 1.9550 | 1.8839 | −2.2665 | 2.0193 |
| | | | | | | 24 | 1.9649 | 1.9550 | −0.3626 | 0.2467 |
| | | | | | | 25 | 2.0236 | 1.9649 | −1.5388 | 2.1507 |

Because the addition power of profile (2) was set to be an irrational number multiple, there are no locations for which the zone diameters of either of profiles (1) or (2) match, but the intensity distribution on the optical axis of the composite profile (FIG. 14C) shows an intensity distribution for which the focal point peak is generated at a point correlating to the addition power set with profiles (1) and (2).

In contrast to the examples for which the addition power was set with a rational number in the previous examples, with this example, there is no structure that is exactly synchronous because the addition power is set with an irrational number. However, as can be seen from FIG. 14A, the seventh zone radius of profile (1) and the fifth zone radius of profile (2), and the fourteenth zone radius of profile (1) and the tenth zone radius of profile (2) are close, and it is possible to regard the zone radii as almost matching. Also, from the knowledge that the desired image characteristics can be manifested even without having a synchronous structure with example 8, this example shows image characteristics that have almost no difference at all with the profile synthesized with a=5 and b=7 with Equation 8. As yet another example, for example when the addition power of profile (2) is set as a multiple of $1/\sqrt{(2.5)}$ of that of profile (1), $1/\sqrt{(2.5)}=1/1.581\ldots$, and it is possible to express this approximately in the form of a rational number as 5/8. In this case, characteristics are shown that have almost no difference from the image characteristics of a profile synthesized with a=5 and b=8.

With this example 9, an irrational number is used as b in Equation 8, and from the results of this example as well, a and b in Equation 8 can be understood as being able to be defined broadly as real numbers including irrational numbers. Of course, even in a case when set with an irrational number, it is possible to express this in the form of a rational number that approximates that as noted previously, so it is of course possible to also use an integer as a hierarchical requirement for a and b. Therefore, even in a case when the values of a and b are mathematically set as irrational numbers, it is possible to regard this as a rational number as an optical technical concept to understand the optical characteristics, and as long as the optical effects of the present invention are achieved, whether or not the value of a and b is a rational number or irrational number is not typically a big problem technically in terms of practical use, and such cases are included within the present invention.

Also, as can also be understood from this example 9, by setting the addition power of profile (2) with an irrational number multiple of that of profile (1), it is possible to further improve the degree of freedom for setting the intermediate focal point position.

[Example 10] (Synthesis of a Profile Having a Fresnel Pitch and a Profile Having Equal-Pitch Regions in a Zone Region)

Profile (1) is the same as that of example 1 except that the phase constant is set at h=0.3, and for the zone pitch of profile (2) the first zone radius is the same as that of profile (1), and the second zone and thereafter has a zone pitch for which the zone pitches have equal pitches of 0.174 mm. The phase constant of profile (2) is set at h=0.4. Details of the composite profile of the profiles are respectively shown in Table 10 and FIGS. 15A, 15B, and 15C. Also, the intensity distribution of the first to twelfth zone regions of the composite profile are shown in FIG. 15D. We can see from the intensity distribution diagram that clear peaks are formed in the respective far, near, and intermediate regions.

TABLE 10

[Example 10]

| Profile (1) Addition power $P_1 = 4D$ | | | Profile (2) Equal-pitch zone included | | | Composite profile (Example 10) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.3 | 1 | 0.5225 | 0.4 | 1 | 0.5225 | 0 | −2.1991 | 2.1991 |
| 2 | 0.7389 | 0.3 | 2 | 0.6967 | 0.4 | 2 | 0.6967 | 0.5225 | −1.8311 | 2.1991 |
| 3 | 0.9050 | 0.3 | 3 | 0.8708 | 0.4 | 3 | 0.7389 | 0.6967 | −0.2957 | 0.6822 |
| 4 | 1.0450 | 0.3 | 4 | 1.0450 | 0.4 | 4 | 0.8708 | 0.7389 | −1.8113 | 1.5893 |
| 5 | 1.1633 | 0.3 | 5 | 1.2192 | 0.4 | 5 | 0.9050 | 0.8708 | −0.1788 | 0.7019 |
| 6 | 1.2798 | 0.3 | 6 | 1.3933 | 0.4 | 6 | 1.0450 | 0.9050 | −2.1991 | 1.7061 |
| 7 | 1.3824 | 0.3 | 7 | 1.5675 | 0.4 | 7 | 1.1683 | 1.0450 | −1.4658 | 2.1991 |
| 8 | 1.4778 | 0.3 | | | | 8 | 1.2192 | 1.1683 | −1.1732 | 0.4192 |
| 9 | 1.5675 | 0.3 | | | | 9 | 1.2798 | 1.2192 | −0.5616 | 1.3401 |
| | | | | | | 10 | 1.3824 | 1.2798 | −2.0414 | 1.3233 |
| | | | | | | 11 | 1.3933 | 1.3824 | −0.5300 | −0.1565 |
| | | | | | | 12 | 1.4778 | 1.3933 | −0.9055 | 1.9833 |
| | | | | | | 13 | 1.5675 | 1.4778 | −2.1991 | 0.9795 |

This example differs from the group of examples noted previously (examples 1 to 9), and is a composite example of when equal pitches are included in the zone pitch of one profile. The zone pitch of the second zone and thereafter of profile (2) is set as 0.174 mm, and with this example, the zone diameter is matched for the fourth and ninth zones of profile (1) and the fourth and seventh zones of profile (2). Differing from the previous examples in which the profiles having a Fresnel pitch are synthesized, zone diameters are matched synchronously by different integer values, namely, three zones from the second to fourth and five zones from the fifth to ninth of the profile (1) with three zones from the second to fourth and three zones from the fifth to seventh of the profile (2). When the number of constituent equal-pitch zones is high as with this example, it is not possible to specify the addition power defined with the Fresnel zone setting equation of Equation 1. However, as was noted in the sixth mode section of the present invention in the Means to Solve the Problems section, by interpreting that it is not possible to specify the addition power $P_2$ with a=0 for Equation 8, this example is also a preferable example of the present invention. The essential addition power $P_2$ of the profile for which equal-pitch zones are the main constituents has an intensity distribution like that shown in FIG. 15E with this example, for example (first to seventh zone regions of profile (2)), and though this does not give a clear +1 order diffraction peak, by the cooperative effect of mutual interference and the like of light with synthesis with other profiles, it is possible to generate a clear intermediate region peak like that shown in FIG. 15D. Therefore, even a profile that does not follow the Fresnel zone setting equation like that of this example can be an important starting profile.

With this composite profile, though there is not a regular repeated structure, there is shown an intensity distribution for which peaks are formed in the respective far, near, and intermediate regions. Thus, the composite profile comprising this combination also is useful as a multi-focal ophthalmic lens.

This kind of combination of profiles (1) and (2) is not limited only to Fresnel pitches, but can also be used with items having other pitch formats, such as an item constituted from equal pitches such as with this example, for example.

[Example 11] (Synthesis of a Profile Having a Fresnel Pitch and a Profile with Two Different Equal-Pitch Zones)

The addition power of profile (1) is 4 D the same as with example 1, and with respect to the profile (2), the addition power $P_2$ of zones from the first to third is set based on the standard setting equation expressed by Equation 12 so that $P_2=4\times(3/4)=3$ D, the zones from the fourth to sixth are equal-pitch zones whose pitch is 0.1443 mm, and the zones from the seventh to ninth are equal-pitch zones whose pitch is 0.1107 mm. The composite profile of this example is constituted by overlapping the profiles (1) and (2). For both profiles (1) and (2), the phase constant is set at h=0.4.

Figure 16A:
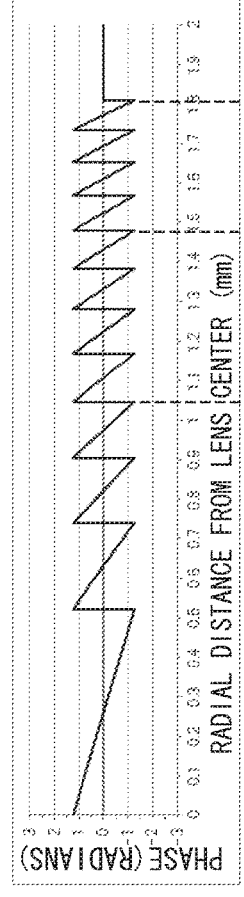
FIGS. 16A-16D are drawings relating to the diffractive multi-focal lens as example 11 of the present invention, where

Profile (2) of this example has two equal-pitch zones of different pitches coexisting in the profile, and compared to the example for which there was the same equal-pitch zone with example 10, this example shows a case of being constituted with different equal-pitch zones. The details of profiles (1) and (2) and the composite profile are shown respectively in Table 11 and FIGS. 16A, 16B, and 16C.

TABLE 11

[Example 11]

| | Profile (1) Addition power $P_1 = 4D$ | | | Profile (2) Addition power $P_2 = 3D$ | | | Composite profile (Example 11) | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.4 | 1 | 0.6033 | 0.4 | 1 | 0.5225 | 0 | −2.1766 | 2.5133 |
| 2 | 0.7389 | 0.4 | 2 | 0.8532 | 0.4 | 2 | 0.6033 | 0.5225 | −0.9387 | 0.3367 |
| 3 | 0.9050 | 0.4 | 3 | 1.0450 | 0.4 | 3 | 0.7389 | 0.6033 | −1.3637 | 1.5746 |
| 4 | 1.0450 | 0.4 | 4 | 1.1893 | 0.4 | 4 | 0.8532 | 0.7389 | −1.7300 | 1.1496 |
| 5 | 1.1683 | 0.4 | 5 | 1.3336 | 0.4 | 5 | 0.9050 | 0.8532 | −0.6783 | 0.7833 |
| 6 | 1.2798 | 0.4 | 6 | 1.4778 | 0.4 | 6 | 1.0450 | 0.9050 | −2.5133 | 1.8349 |
| 7 | 1.3824 | 0.4 | 7 | 1.5885 | 0.4 | 7 | 1.1683 | 1.0450 | −2.1485 | 2.5133 |
| 8 | 1.4778 | 0.4 | 8 | 1.6993 | 0.4 | 8 | 1.1893 | 1.1683 | −0.4719 | 0.3647 |
| 9 | 1.5675 | 0.4 | 9 | 1.8100 | 0.4 | 9 | 1.2798 | 1.1893 | −1.5777 | 2.0414 |
| 10 | 1.6523 | 0.4 | | | | 10 | 1.3336 | 1.2798 | −1.3164 | 0.9356 |
| 11 | 1.7329 | 0.4 | | | | 11 | 1.3824 | 1.3336 | −0.8507 | 1.1969 |
| 12 | 1.8100 | 0.4 | | | | 12 | 1.4778 | 1.3824 | −2.5133 | 1.6626 |
| | | | | | | 13 | 1.5675 | 1.4778 | −2.0350 | 2.5133 |
| | | | | | | 14 | 1.5885 | 1.5675 | −0.6244 | 0.4782 |
| | | | | | | 15 | 1.6523 | 1.5885 | −1.4466 | 1.8888 |
| | | | | | | 16 | 1.6993 | 1.6523 | −1.4644 | 1.0667 |
| | | | | | | 17 | 1.7329 | 1.6993 | −0.7640 | 1.0489 |
| | | | | | | 18 | 1.8100 | 1.7329 | −2.5133 | 1.7492 |

Figure 16B:
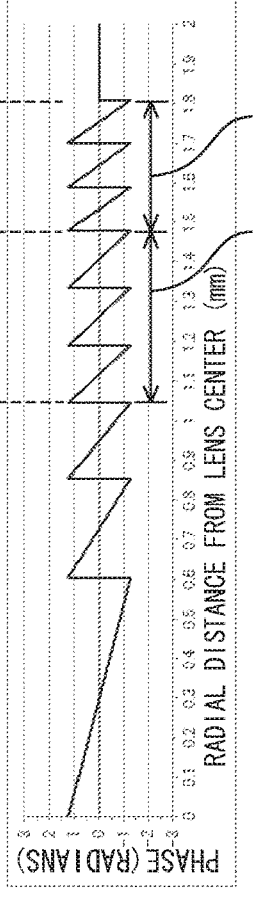
Figure 16C:
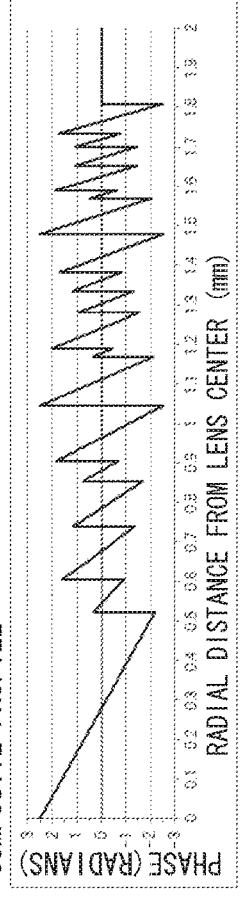
Figure 16D:
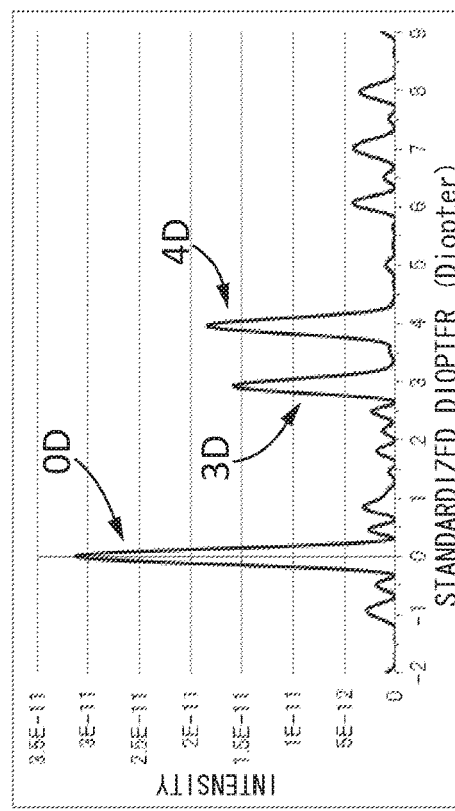

Profile (2) of this example has two different equal-pitch zones as shown in FIG. 16B, and three continuous zone pitches of profile (2) are equal to the four continuous zone pitches of profile (1). The number of zones for the synchronous structure is not different from example 1, but the blaze shape distribution of each synchronous unit is slightly different with the composite profile. However, the optical axis direction intensity distribution of the composite profile (FIG. 16D) has a peak generated at the focal point position based on the addition power of each profile, the same as with example 1. Even when including equal pitches and overlapping profiles existing in a plurality of regions for which there are two or more different equal-pitch zones in this way, the target image characteristics can be obtained.

[Example 12] (Partial Synthesis (Part 1))

With the present invention, it is also possible to use an item for which the profiles are partially overlapped and synthesized. With this example, shown is an example of an item for which profile (1) and profile (2) used with example 6 are partially overlapped and synthesized.

Figure 17A:
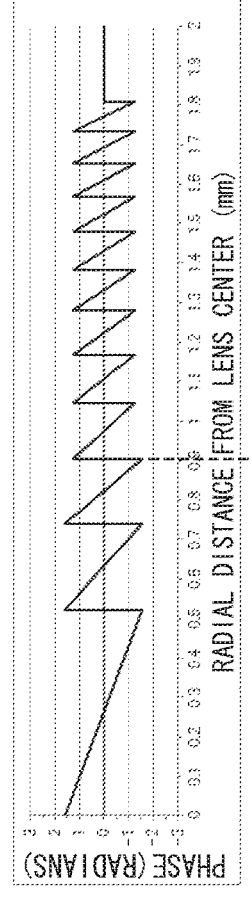
FIGS. 17A-17D are drawings relating to the diffractive multi-focal lens as example 12 of the present invention, where
Figure 17B:
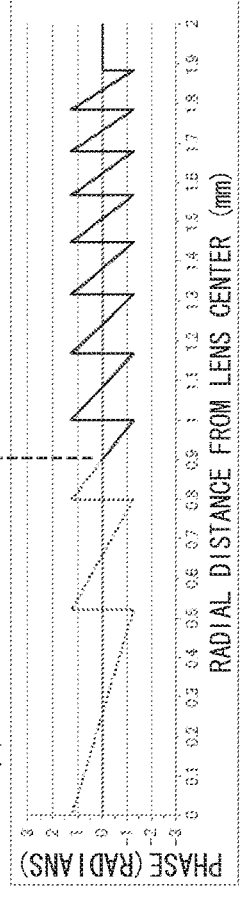
Figure 17C:
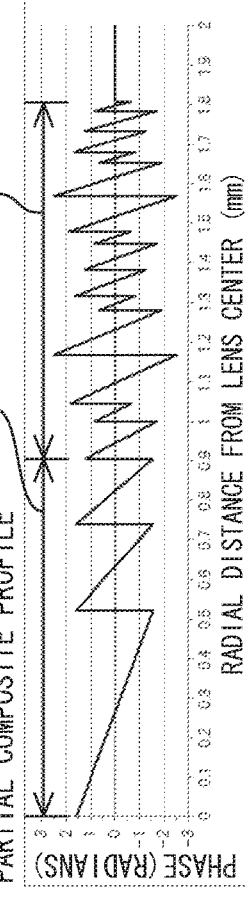

Specifically, with example 6, profile (1) and profile (2) had the entire regions overlapped, but with this example, from the first to third zones of the composite profile are a diffractive structure with the profile (1) left as is, and profile (1) and profile (2) are overlapped at the region outside from the third zone radius point (0.9050 mm). The details of this partial synthesis are shown in Table 12 and FIGS. 17A, 17B, and 17C.

TABLE 12

[Example 12]

| | Profile (1) Addition power $P_1 = 4D$ | | | Profile (2) Addition power $P_2 = 3D$ | | | Composite profile (Example 12) | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.5225 | 0.5 | 1 | 0.5225 | 0 | 1 | 0.5225 | 0 | −1.5708 | 1.5708 |
| 2 | 0.7389 | 0.5 | 2 | 0.7981 | 0 | 2 | 0.7389 | 0.5225 | −1.5708 | 1.5708 |
| 3 | 0.9050 | 0.5 | 3 | 1.0005 | 0.4 | 3 | 0.9050 | 0.7389 | −1.5708 | 1.5708 |
| 4 | 1.0450 | 0.4 | 4 | 1.1683 | 0.4 | 4 | 1.0005 | 0.9050 | −1.7146 | 1.1862 |
| 5 | 1.1683 | 0.4 | 5 | 1.3149 | 0.4 | 5 | 1.0450 | 1.0005 | −0.6662 | 0.7986 |
| 6 | 1.2798 | 0.4 | 6 | 1.4467 | 0.4 | 6 | 1.1683 | 1.0450 | −2.5133 | 1.8471 |
| 7 | 1.3824 | 0.4 | 7 | 1.5675 | 0.4 | 7 | 1.2798 | 1.1683 | −1.9120 | 2.5133 |
| 8 | 1.4778 | 0.4 | 8 | 1.6796 | 0.4 | 8 | 1.3149 | 1.2798 | −0.8595 | 0.6013 |
| 9 | 1.5675 | 0.4 | 9 | 1.7847 | 0.4 | 9 | 1.3824 | 1.3149 | −1.2866 | 1.6537 |
| 10 | 1.6523 | 0.4 | 10 | 1.8839 | 0.4 | 10 | 1.4467 | 1.3824 | −1.6939 | 1.2267 |
| 11 | 1.7329 | 0.4 | | | | 11 | 1.4778 | 1.4467 | −0.6476 | 0.8193 |
| 12 | 1.8100 | 0.4 | | | | 12 | 1.5675 | 1.4778 | −2.5133 | 1.8657 |

TABLE 12-continued

[Example 12]

| Profile (1) Addition power $P_1 = 4D$ | | | Profile (2) Addition power $P_2 = 3D$ | | | Composite profile (Example 12) | | | | |
|---|---|---|---|---|---|---|---|---|---|---|
| | Zone radius | | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| | | | | | | 13 | 1.6523 | 1.5675 | −1.9009 | 2.5133 |
| | | | | | | 14 | 1.6796 | 1.6523 | −0.8512 | 0.6123 |
| | | | | | | 15 | 1.7329 | 1.6796 | −1.2757 | 1.6621 |
| | | | | | | 16 | 1.7847 | 1.7329 | −1.6876 | 1.2376 |
| | | | | | | 17 | 1.8100 | 1.7847 | −0.6412 | 0.8257 |

With this example, the phase constant of the blaze of the first to third zones of profile (1) is set to h=0.5, and with profile (2), the phase constant of the first and second zones is an item showing that the phase of this region is zero, and is displayed as h=0. Also, with the third zone of profile (2), the phase constant is zero until the region at which the third zone of profile (1) overlaps, and from thereafter, the phase constant is set as h=0.4. From the drawing, the composite profile has only profile (1) from the first to third zones, and has profiles (1) and (2) overlapping from the fourth and thereafter so as to be a partially synthesized profile.

Figure 17D:
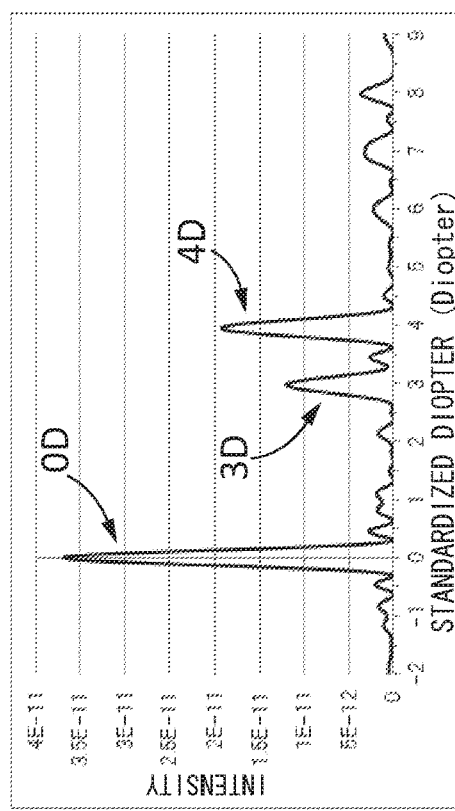

FIG. 17D shows the intensity distribution of the composite profile. Even with a partially synthesized profile, a focal point peak is generated at a point correlating to the set addition power of profiles (1) and (2).

When the multi-focal lens having this kind of diffractive structure of this example 12 is used as an ophthalmic lens such as a contact lens, intraocular lens or the like, for example, in an environment for which the illuminance is high and the pupil diameter is small such as outdoors during fine weather or the like, it functions mainly as an ophthalmic lens for intensity distribution only of profile (1), in other words, a two focal point type for far and near points. On the other hand, for example in an environment for which the illuminance is somewhat low such as inside an office, at the sink, or the like, for example, the composite profile region is exposed by the pupil diameter being enlarged, so it has intensity distribution including that region, and functions as a three point type lens that also has an intermediate region point.

Therefore, with this example of partial synthesis, as described in section iii, Other Problems That The Present Invention Can Solve Optionally As Needed, in environments with high illuminance, since the depth of focus becomes deeper as the pupil becomes smaller, it is possible to see the intermediate region even with a far and near two point lens, and on the other hand, the depth of focus becomes shallow in an environment in which the illuminance is somewhat dark such as in an office or the like, and in light of the relationship of requirements for ophthalmic lenses for human eye physiology, such as that it is more necessary to reliably form a focal point in the intermediate region since the frequency of occurrence of personal computer work and the like is increasing, this can be an example of specifications for a multi-focal ophthalmic lens for which it is possible to selectively form focal points to match the user's work objective and work environment.

[Example 13] (Partial Synthesis (Part 2))

With example 12, an example was shown of partial synthesis from midway in the third zone of profile (2). For this example, as a different example of partial synthesis, we will show an example of a case of synthesis after freely setting the matching point in a case when doing partial synthesis from a point for which the zone diameters of profile (1) and profile (2) match.

Specifically, with this example, the addition power and zone pitch of profile (1), and the addition power of profile (2) are the same as with example 1, and the zone pitch of profile (2) is determined based on Equation 7 which is a general setting equation such that the zone radius of profile (2) matches the sixth zone radius of profile (1). The phase constant being set as h=0.5 from the first to sixth zones of profile (1) and being set as h=0.4 from the seventh zone and thereafter, and from the second zone and thereafter of profile (2) being set to h=0.5 are all different from example 1. The phase constant of the first zone of profile (2) is displayed as h=0 as an item indicating that the phase of this region is zero.

Figure 18A:
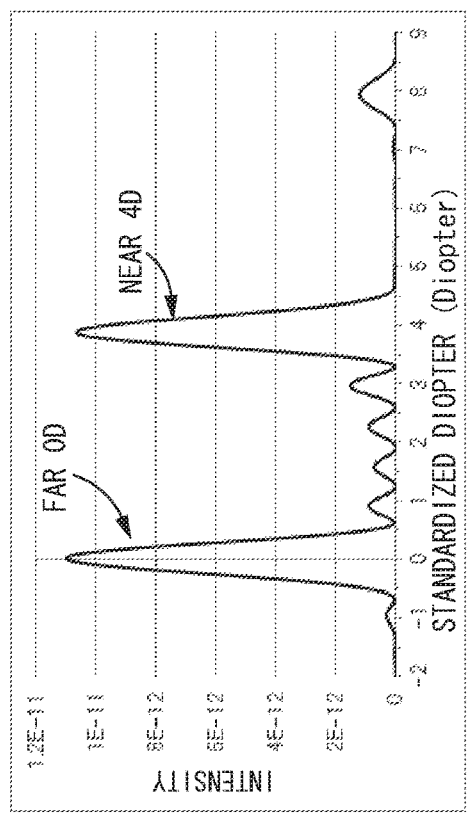
FIGS. 18A-18E are drawings relating to the diffractive multi-focal lens as example 13 of the present invention, where
Figure 18B:
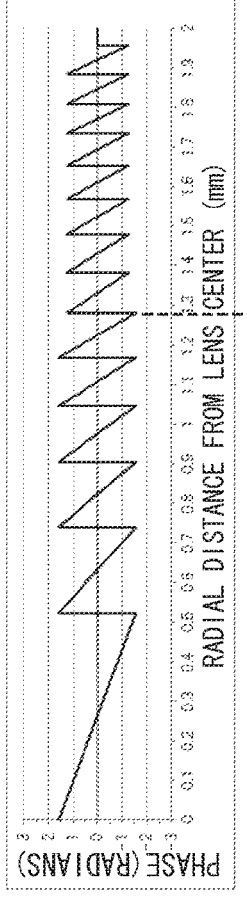
Figure 18C:
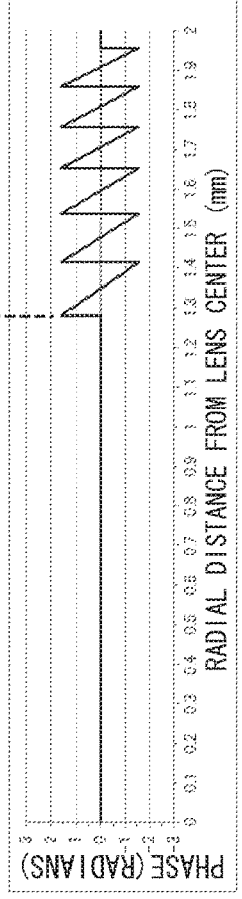

In specific terms, the first zone radius of profile (2) is the same as the sixth zone radius of profile (1), and this zone radius is substituted for $r_1'$ of Equation 7 for determining from the second the zone pitch of profile (2) and thereafter. The details of profile (1), profile (2) set in this way, and the composite profile of these are shown in Table 13 and FIGS. 18A, 18B, and 18C.

TABLE 13

[Example 13]

| Profile (1) Addition power $P_1 = 4D$ | | Profile (2) Addition power $P_2 = 3D$ | | Composite profile (Example 13) | | | | |
|---|---|---|---|---|---|---|---|---|
| | | | | | Zone radius (mm) | | Phase (radians) | |
| Zone | Zone radius (mm) | Phase | Zone | Zone radius (mm) | Phase | Zone | | |
| No. n | $r_n$ | constant h | No. m | $r_m$ | constant h | No. i | Outer radius $r_i$ | Inner radius $r_{i-1}$ | $\phi_i'$ | $\phi_{i-1}'$ |
| 1 | 0.5225 | 0.5 | 1 | 1.2798 | 0 | 1 | 0.5225 | 0 | −1.5708 | 1.5708 |
| 2 | 0.7389 | 0.5 | 2 | 1.4149 | 0.5 | 2 | 0.7389 | 0.5225 | −1.5708 | 1.5708 |
| 3 | 0.9050 | 0.5 | 3 | 1.5382 | 0.5 | 3 | 0.9050 | 0.7389 | −1.5708 | 1.5708 |
| 4 | 1.0450 | 0.5 | 4 | 1.6523 | 0.5 | 4 | 1.0450 | 0.9050 | −1.5708 | 1.5708 |
| 5 | 1.1683 | 0.5 | 5 | 1.7590 | 0.5 | 5 | 1.1683 | 1.0450 | −1.5708 | 1.5708 |
| 6 | 1.2798 | 0.5 | 6 | 1.8596 | 0.5 | 6 | 1.2798 | 1.1683 | −1.5708 | 1.5708 |
| 7 | 1.3824 | 0.4 | 7 | 1.9550 | 0.5 | 7 | 1.3824 | 1.2798 | −2.0708 | 2.8274 |
| 8 | 1.4778 | 0.4 | | | | 8 | 1.4149 | 1.3824 | −1.1708 | 0.4424 |
| 9 | 1.5675 | 0.4 | | | | 9 | 1.4778 | 1.4149 | −1.2894 | 1.9708 |
| 10 | 1.6523 | 0.4 | | | | 10 | 1.5382 | 1.4778 | −2.0060 | 1.2239 |
| 11 | 1.7329 | 0.4 | | | | 11 | 1.5675 | 1.5382 | −0.4927 | 1.1356 |
| 12 | 1.8100 | 0.4 | | | | 12 | 1.6523 | 1.5675 | −2.8274 | 2.0206 |
| 13 | 1.8839 | 0.4 | | | | 13 | 1.7329 | 1.6523 | −2.0602 | 2.8274 |
| 14 | 1.9550 | 0.4 | | | | 14 | 1.7590 | 1.7329 | −1.1642 | 0.4531 |
| | | | | | | 15 | 1.8100 | 1.7590 | −1.2785 | 1.9774 |
| | | | | | | 16 | 1.8596 | 1.8100 | −2.0008 | 1.2348 |
| | | | | | | 17 | 1.8839 | 1.8596 | −0.4862 | 1.1408 |
| | | | | | | 18 | 1.9550 | 1.8839 | −2.8274 | 2.0271 |

With this example, the first to sixth zones of the composite profile are profile (1), and from the seventh and thereafter are a partially synthesized profile of profiles (1) and (2).

Figure 18D:
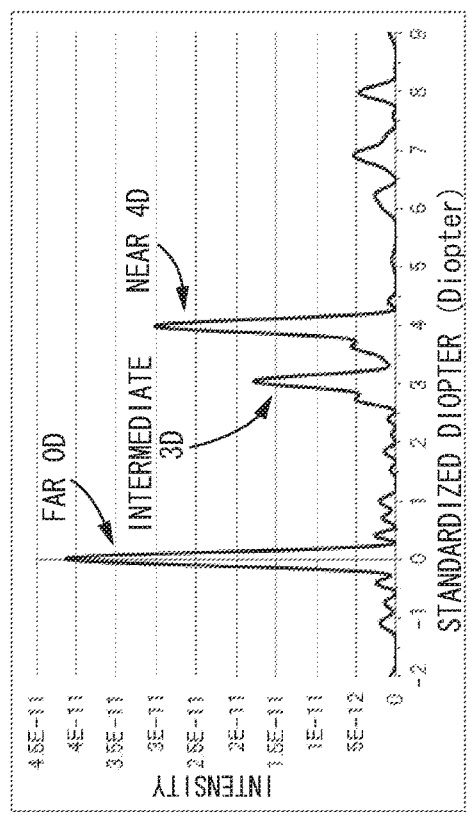
Figure 18E:
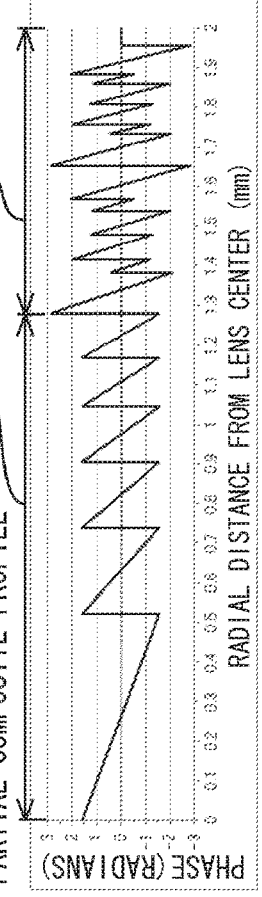

When the aperture diameter is up to the range of the sixth zone (radius approximately 1.3 mm), as shown in FIG. 18D, the profile of this example functions as a two focal point lens having peaks at two locations of far (0 D) and near (4 D) based on profile (1), and when the aperture diameter becomes larger than that range, including the contribution from the partial composite profile, a peak is also generated at the point of approximately 3 D, and it functions as a three focal point lens (FIG. 18E). Therefore, with the partial composite profile of this example, when used for an ophthalmic lens, for example, this can also have specifications as an ophthalmic lens for which it is possible to selectively form focal points to match the user's work objective and work environment.

[Example 14] (Partial Synthesis (Part 3)—Item Comprising the Non-Synthesized Part (Fresnel+Equal Pitches)

As profile (1), an item was used for which the third to fifth zones of profile (1) of example 1 are substituted for the three zones for which the pitch of this space is divided equally into three equal pitches (pitch of 0.143 mm).

As shown in Table 14, the phase constant of each zone of profile (1) is set to h=0.5 up to the first to fifth zones, and other than that is set to h=0.4. Meanwhile, with profile (2), the first zone radius is made to be the same as the fifth zone diameter of profile (1) (radius 1.168 mm), this zone radius is substituted for $r_1'$ of Equation 7, the general setting equation, and the zone pitch is determined such that the addition power is 3 D. Also, the phase constant of the first zone of profile (2) is set to h=0, from the second zone and thereafter is set to h=0.4, and the phase of the first zone is zero. The details of each profile and the composite profile (partial composite profile) are shown in Table 14 and FIGS. 19A, 19B, and 19C.

TABLE 14

[Example 14]

| Profile (1) Addition power $P_1 = 4D$ Equal-pitch zone partially included | | | Profile (2) Addition power $P_2 = 3D$ | | | Composite profile (Example 14) | | | | |
|---|---|---|---|---|---|---|---|---|---|---|
| | Zone radius | | | Zone radius | | | Zone radius (mm) | | Phase (radians) | |
| Zone No. n | (mm) $r_n$ | Phase constant h | Zone No. m | (mm) $r_m$ | Phase constant h | Zone No. i | Outer radius $r_i$ | Inner radius $r_{i-1}$ | $\phi_i'$ | $\phi_{i-1}'$ |
| 1 | 0.5225 | 0.5 | 1 | 1.1683 | 0 | 1 | 0.5225 | 0 | −1.5708 | 1.5708 |
| 2 | 0.7389 | 0.5 | 2 | 1.3149 | 0.4 | 2 | 0.7389 | 0.5225 | −1.5708 | 1.5708 |
| 3 | 0.8821 | 0.5 | 3 | 1.4467 | 0.4 | 3 | 0.8821 | 0.7389 | −1.5708 | 1.5708 |
| 4 | 1.0252 | 0.5 | 4 | 1.5675 | 0.4 | 4 | 1.0252 | 0.8821 | −1.5708 | 1.5708 |
| 5 | 1.1683 | 0.5 | 5 | 1.6796 | 0.4 | 5 | 1.1683 | 1.0252 | −1.5708 | 1.5708 |
| 6 | 1.2798 | 0.4 | 6 | 1.7847 | 0.4 | 6 | 1.2798 | 1.1683 | −1.9120 | 2.5133 |
| 7 | 1.3824 | 0.4 | 7 | 1.8839 | 0.4 | 7 | 1.3149 | 1.2798 | −0.8595 | 0.6013 |
| 8 | 1.4778 | 0.4 | | | | 8 | 1.3824 | 1.3149 | −1.2866 | 1.6537 |
| 9 | 1.5675 | 0.4 | | | | 9 | 1.4467 | 1.3824 | −1.6939 | 1.2267 |
| 10 | 1.6523 | 0.4 | | | | 10 | 1.4778 | 1.4467 | −0.6476 | 0.8193 |
| 11 | 1.7329 | 0.4 | | | | 11 | 1.5675 | 1.4778 | −2.5133 | 1.8657 |
| 12 | 1.8100 | 0.4 | | | | 12 | 1.6523 | 1.5675 | −1.9009 | 2.5133 |
| 13 | 1.8839 | 0.4 | | | | 13 | 1.6796 | 1.6523 | −0.8512 | 0.6123 |
| | | | | | | 14 | 1.7329 | 1.6796 | −1.2757 | 1.6621 |
| | | | | | | 15 | 1.7847 | 1.7329 | −1.6876 | 1.2376 |
| | | | | | | 16 | 1.8100 | 1.7847 | −0.6412 | 0.8257 |
| | | | | | | 17 | 1.8839 | 1.8100 | −2.5133 | 1.8720 |

The substantial composite region of this example is the sixth and thereafter of profile (1) and the second and thereafter of profile (2), and this is an example for which these are partially synthesized. In the region for which the aperture diameter correlates to the first to fifth of the composite profile, the image characteristics of profile (1) are shown (FIG. 19D). Because it includes equal-pitch regions, the region of only profile (1) shows intensity distribution for which a small peak is also generated in the intermediate region. If the aperture diameter expands to a size greater than this, an item is shown for which the image characteristics also have the contribution from the composite profile synthesized, and the peak strength of the intermediate region is further strengthened (FIG. 19E).

In this way, with this example, a peak is already generated in the intermediate region in the profile (1) only region (first to fifth zones), so for example when used for an ophthalmic lens, even in an environment when the illuminance is high and the pupil diameter is small such as outdoors during fine weather or the like, it is possible to have an ophthalmic lens for which ensuring of intermediate region visual acuity is more reliable, and the intermediate visual acuity is even more greatly ensured for work such as viewing a personal computer monitor screen, for example, in environments for which the pupil is slightly dilated such as in an office, and vision is sufficiently possible in near regions as well.

Incidentally, with examples 12, 13, and 14 for which a composite profile was provided in partial regions in the lens radial direction noted above, these are examples for which the lens peripheral region is partially synthesized, but the different zone profile partial synthesis is not limited to that region, and it is also possible to have partial synthesis limited to regions near the lens center. Furthermore, it is acceptable for there to be one or a plurality of locations of composite regions at any location in the lens radial direction.

With examples 12, 13, and 14, when doing partial synthesis, Equation 7 noted above is used to set the zone position of profile (2) from any position. Equation 7 which is a general setting equation is used to freely vary the first zone radius of the starting profiles with examples 6, 7, and 8, but it is also possible to set a zone pitch that can also be used with this partial synthesis and have the part being partially synthesized regarded as the first zone radius. At this time, when the partially synthesized position is matched with the zone radius of the other profile, a synchronous structure is formed between zones of both profiles within the partially synthesized profile. Meanwhile, when partial synthesis is done from a position midway in a certain zone of the other profile, an asynchronous structure results. For the difference in synchronous and asynchronous structures with partially synthesized parts, as has already been shown with examples 6, 7, 8 and the like, there are no differences specific to those image characteristics, and multi-focal characteristics as shown with the present invention can be manifested.

Also, to match the zone radii for both profiles at the start point or end point of the partially synthesized region for profiles (1) and (2), it is possible to use Equation 16 and Equation 17 described previously to specify the zone diameter to be matched between zone profiles (1) and (2).

[Example 15] (Variable Example of Addition Power of Profile (1))

With the examples up to now, we showed examples when the addition power of profile (1) was 4 D. That addition power is close to the actual addition power particularly when using as an intraocular lens among ophthalmic lenses. This example describes an example of the composite profile when the addition power of profile (1) is varied and set at 2 D. That addition power is the realistic addition power when the ophthalmic lens is a contact lens. Even if the addition power of profile (1) is varied, we will describe with the examples below that this does not change the usefulness and effect of the present invention.

Figure 20A:
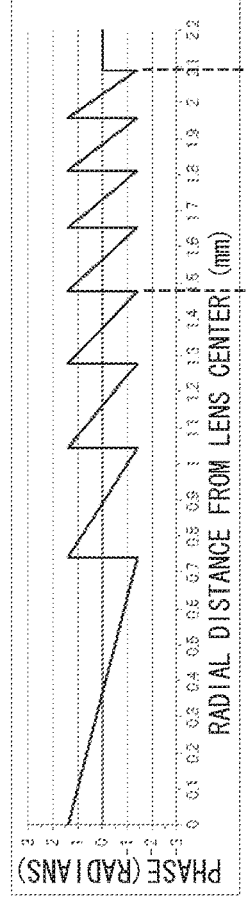
FIGS. 20A-20D are drawings relating to the diffractive multi-focal lens as example 15 of the present invention, where
Figure 20B:
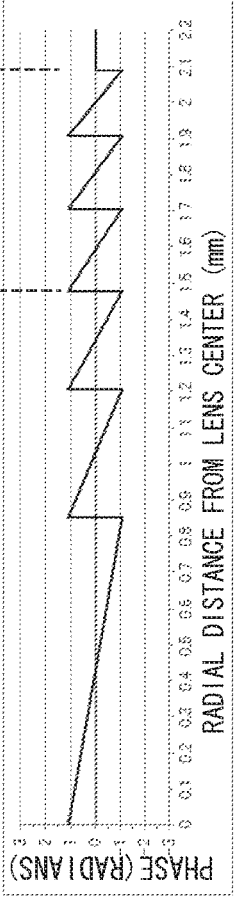
Figure 20C:
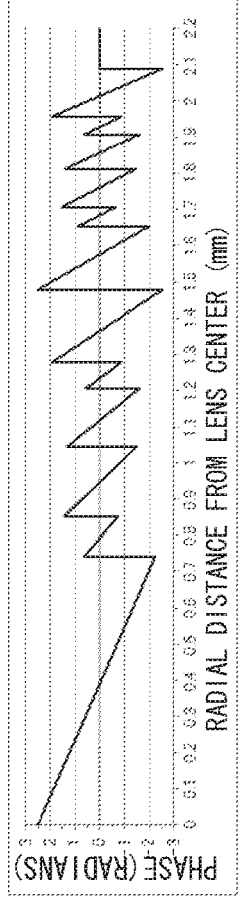

The same as with example 1, with a blaze shaped phase modulation type diffractive structure, two types of profiles were synthesized, for which the addition power $P_1$ of profile (1) is set to 2 D, and for which the addition power $P_2$ of profile (2) is set to $P_2=2\times(3/4)=1.5$ D so that it is 3/4 of the addition power of profile (1). The phase constants of profiles (1) and (2) are respectively set at h=0.45 and h=0.35 (FIGS. 20A and 20B). The details of the composite profile obtained by synthesizing the phase functions of profiles (1) and (2) are shown respectively in Table 15 and FIG. 20C.

peak of the 2 D position as the focal point for near vision, and the peak of the 1.5 D position as the focal point for intermediate vision. There is a difference in the peak appearance position due to varying the addition power, but in regards to the mode of the intensity distribution, it shows the same characteristics as those of example 1.

This example is useful as a multi-focal contact lens for patients with advanced presbyopia but who still have a certain amount of their own residual power of accommodation, reading is possible with a 2 D focal point for near vision, and vision is ensured for the relatively near intermediate distance such as for personal computer work or the like using the 1.5 D focal point set for intermediate vision.

[Example 16] (Example of Synthesis of Three or More Profiles (Part 1))

Next, this example 16 shows the image characteristics of the composite profile in the case of three or more starting profiles. With this example, three profiles, profiles (1), (2), and (3), are prepared as starting profiles, and an example is shown of the composite profile obtained by synthesizing their respective phase functions.

The zone diameter of profile (1) was set using the standard setting equation of Equation 11 so that the addition power is

TABLE 15

[Example 15]

| Profile (1) Addition power $P_1 = 2D$ | | Profile (2) Addition power $P_2 = 1.5D$ | | Composite profile (Example 15) | | | | |
|---|---|---|---|---|---|---|---|---|
| Zone radius | | Zone radius | | | Zone radius (mm) | | Phase | |
| Zone No. n | (mm) $r_n$ | Phase constant h | Zone No. m | (mm) $r_m$ | Phase constant h | Zone No. i | Outer radius $r_i$ | Inner radius $r_{i-1}$ | (radians) $\phi_i'$ | $\phi_{i-1}'$ |
| 1 | 0.7389 | 0.45 | 1 | 0.8532 | 0.35 | 1 | 0.7389 | 0 | −2.2186 | 2.5133 |
| 2 | 1.0450 | 0.45 | 2 | 1.2066 | 0.35 | 2 | 0.8532 | 0.7389 | −0.7418 | 0.6088 |
| 3 | 1.2798 | 0.45 | 3 | 1.4778 | 0.35 | 3 | 1.0450 | 0.8532 | −1.5074 | 1.4573 |
| 4 | 1.4778 | 0.45 | 4 | 1.7065 | 0.35 | 4 | 1.2066 | 1.0450 | −1.6321 | 1.3201 |
| 5 | 1.6523 | 0.45 | 5 | 1.9079 | 0.35 | 5 | 1.2798 | 1.2066 | −0.9077 | 0.5670 |
| 6 | 1.8100 | 0.45 | 6 | 2.0900 | 0.35 | 6 | 1.4778 | 1.2798 | −2.5133 | 1.9197 |
| 7 | 1.9550 | 0.45 | | | | 7 | 1.6523 | 1.4778 | −1.9920 | 2.5133 |
| 8 | 2.0900 | 0.45 | | | | 8 | 1.7065 | 1.6523 | −0.6574 | 0.8354 |
| | | | | | | 9 | 1.8100 | 1.7065 | −1.4443 | 1.5417 |
| | | | | | | 10 | 1.9079 | 1.8100 | −1.5947 | 1.3831 |
| | | | | | | 11 | 1.9550 | 1.9079 | −0.8831 | 0.6044 |
| | | | | | | 12 | 2.0900 | 1.9550 | −2.5133 | 1.9443 |

This example is the same as example 1 except for the addition power of profile (1) being set to 2 D (the phase constant is changed as noted in Table 15). Therefore, the structure of the composite profile is almost the same as that of example 1, and the number of zones synchronized is also the same as with example 1.

Figure 20D:
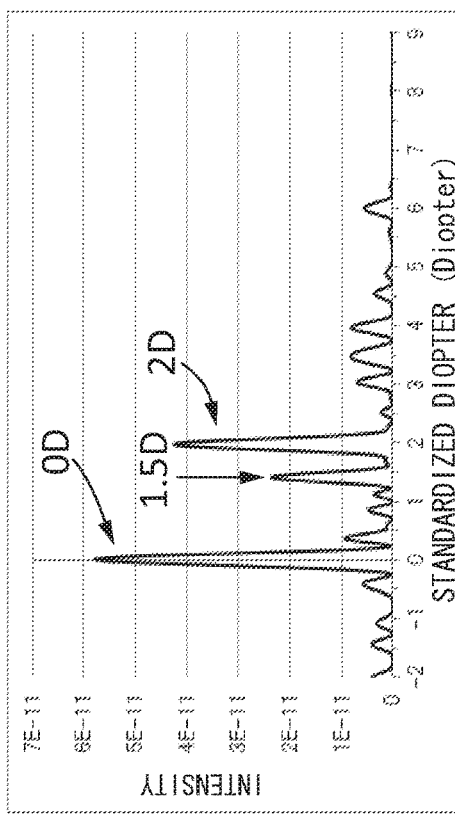

Also, the intensity distribution of the composite profile of this example is as noted in FIG. 20D, and three peaks are formed, the peak of 0 D as the focal point for far vision, the $P_1=4$ D. With profile (2), the zone diameter was set based on the standard setting equation of Equation 12 so that the addition power is $P_2=P_1\times(2/3)=2.666$ D. Next, the addition power of profile (3) was set based on the standard setting equation of Equation 20 so that $P_3=P_1\times(1/3)=1.333$ D. The phase constants of profiles (1), (2), and (3) were respectively set to 0.4, 0.3, and 0.25. The details of each profile and the composite profile are shown in Table 16 and FIGS. 21A to 21D.

TABLE 16

[Example 16]

| Profile (1) Addition power $P_1 = 4D$ | | Profile (2) Addition power $P_2 = 2.666D$ | | Profile (3) Addition power $P_3 = 1.333D$ | | Composite profile (Example 16) | | | | |
|---|---|---|---|---|---|---|---|---|---|---|
| Zone | | Zone | | Zone | | Zone radius (mm) | | | | |
| Zone No. n | radius (mm) $r_n$ | Phase constant h | Zone No. m | radius (mm) $r_m$ | Phase constant h | Zone No. q | radius (mm) $r_q$ | Phase constant h | Zone No. i | Outer radius $r_i$ | Inner radius $r_{i-1}$ | Phase (radians) $\phi_i'$ | $\phi_{i-1}'$ |
| 1 | 0.5225 | 0.4 | 1 | 0.6399 | 0.3 | 1 | 0.9050 | 0.25 | 1 | 0.5225 | 0 | −1.9747 | 2.9845 |
| 2 | 0.7389 | 0.4 | 2 | 0.9050 | 0.3 | 2 | 1.2798 | 0.25 | 2 | 0.6399 | 0.5225 | −1.3748 | 0.5386 |
| 3 | 0.9050 | 0.4 | 3 | 1.1084 | 0.3 | 3 | 1.5675 | 0.25 | 3 | 0.7389 | 0.6399 | −1.5153 | 0.5101 |
| 4 | 1.0450 | 0.4 | 4 | 1.2798 | 0.3 | 4 | 1.8100 | 0.25 | 4 | 0.9050 | 0.7389 | −2.9845 | 0.9980 |
| 5 | 1.1683 | 0.4 | 5 | 1.4309 | 0.3 | 5 | 2.0236 | 0.25 | 5 | 1.0450 | 0.9050 | −1.4129 | 2.9845 |
| 6 | 1.2798 | 0.4 | 6 | 1.5675 | 0.3 | 6 | 2.2168 | 0.25 | 6 | 1.1084 | 1.0450 | −1.0444 | 1.1004 |
| 7 | 1.3824 | 0.4 | 7 | 1.6931 | 0.3 | | | | 7 | 1.1683 | 1.1084 | −1.2914 | 0.8406 |
| 8 | 1.4778 | 0.4 | 8 | 1.8100 | 0.3 | | | | 8 | 1.2793 | 1.1683 | −2.9845 | 1.2219 |
| 9 | 1.5675 | 0.4 | 9 | 1.9198 | 0.3 | | | | 9 | 1.3824 | 1.2798 | −1.3683 | 2.9845 |
| 10 | 1.6523 | 0.4 | 10 | 2.0288 | 0.3 | | | | 10 | 1.4309 | 1.3824 | −1.0030 | 1.1450 |
| 11 | 1.7329 | 0.4 | 11 | 2.1224 | 0.3 | | | | 11 | 1.4778 | 1.4309 | −1.2577 | 0.8819 |
| 12 | 1.8100 | 0.4 | 12 | 2.2168 | 0.3 | | | | 12 | 1.5675 | 1.4778 | −2.9845 | 1.2556 |
| 13 | 1.8839 | 0.4 | | | | | | | 13 | 1.6523 | 1.5675 | −1.3506 | 2.9845 |
| 14 | 1.9550 | 0.4 | | | | | | | 14 | 1.6931 | 1.6523 | −0.9856 | 1.1627 |
| 15 | 2.0236 | 0.4 | | | | | | | 15 | 1.7329 | 1.6931 | −1.2429 | 0.8994 |
| 16 | 2.0900 | 0.4 | | | | | | | 16 | 1.8100 | 1.7329 | −2.9845 | 1.2704 |
| 17 | 2.1548 | 0.4 | | | | | | | 17 | 1.8839 | 1.8100 | −1.3410 | 2.9845 |
| 18 | 2.2168 | 0.4 | | | | | | | 18 | 1.9198 | 1.8839 | −0.9760 | 1.1723 |
| | | | | | | | | | 19 | 1.9550 | 1.9198 | −1.2345 | 0.9090 |
| | | | | | | | | | 20 | 2.0236 | 1.9550 | −2.9845 | 1.2788 |
| | | | | | | | | | 21 | 2.0900 | 2.0236 | −1.3350 | 2.9845 |
| | | | | | | | | | 22 | 2.1224 | 2.0900 | −0.9699 | 1.1782 |
| | | | | | | | | | 23 | 2.1543 | 2.1224 | −1.2291 | 0.9151 |
| | | | | | | | | | 24 | 2.2168 | 2.1543 | −2.9845 | 1.2842 |

The addition power of profile (2), because it is set so as to be (2/3) of $P_1$, the zone diameter of the third, sixth, ninth, and so on of profile (1) and the zone diameters of the second, fourth, sixth, and so on of profile (2) match. On the other hand, the addition power of profile (3) is set to be (1/3) of $P_1$, so the zone diameters of the third, sixth, ninth, and so on of profile (1) and the zone diameters of the first, second, third, and so on of profile (3) match. Also, between profiles (2) and (3), the zone diameters of the second, fourth, sixth, and so on of profile (2) and of the first, second, third, and so on of profile (3) match.

With the composite profile, the zone positions for which all three profile zone diameters match are the fourth, eighth, twelfth, sixteenth, . . . zone positions. With these zone positions, three profile zones are synchronized, so the steps of the blaze at the zones in front of and behind these zone positions (the fourth, fifth, eighth, ninth, twelfth, thirteenth, sixteenth, seventeenth, and so on zone numbers of the composite profile) are at their maximum size, and a repeated structure appears with a synchronous structure for which the region in which all the zone diameters of the three profiles match is the periodic unit.

FIG. 21E shows the intensity distribution of that composite profile.

We can see that in addition to the peak of the 0th order diffracted light set for far vision, peaks are generated at the points corresponding to the addition power of each starting profile. Also, with the combination of phase constants set with the starting profiles of this example, we can see that the strength of each peak is almost equal.

With the profile synthesized from three profiles as noted with this example, when used as a multi-focal ophthalmic lens, one more focal point is formed in the intermediate region, and vision in the intermediate region range is further ensured. Also, in addition to use as a multi-focal ophthalmic lens, this is also useful as a lens element for general use in the optical field that needs multi-focal characteristics.

[Example 17] (Example of Synthesis of Three or More Profiles (Part 2))

Profile (1) is made to be the same as with example 16, and with profile (2), the zone diameter was set based on the standard setting equation of Equation 12 so that the addition power is $P_2=P_1\times(3/4)=3$ D. Next, setting was done based on the standard setting equation of Equation 20 so that the addition power of profile (3) is $P_3=P_1\times(1/2)=2$ D. The phase constant of profiles (1), (2), and (3) are respectively set to 0.3, 0.35, and 0.25. A composite profile was obtained for which the phase functions of these three profiles were added. The details of the starting profiles and the composite profile are shown in Table 17 and FIGS. 22A to 22D.

TABLE 17

[Example 17]

| | Profile (1) Addition power $P_1 = 4D$ | | | Profile (2) Addition power $P_2 = 3D$ | | | Profile (3) Addition power $P_3 = 2D$ | | | Composite profile (Example 17) | | | |
|---|---|---|---|---|---|---|---|---|---|---|---|---|---|
| | Zone | | | Zone | | | Zone | | | Zone radius (mm) | | | |
| Zone No. n | radius (mm) $r_n$ | Phase constant h | Zone No. m | radius (mm) $r_m$ | Phase constant h | Zone No. q | radius (mm) $r_q$ | Phase constant h | Zone No. i | Outer radius $r_i$ | Inner radius $r_{i-1}$ | Phase (radians) $\phi_i'$ | $\phi_{i-1}'$ |
| 1 | 0.5225 | 0.3 | 1 | 0.6033 | 0.35 | 1 | 0.7389 | 0.25 | 1 | 0.5225 | 0 | −2.0727 | 2.8274 |
| 2 | 0.7389 | 0.3 | 2 | 0.8532 | 0.35 | 2 | 1.0450 | 0.25 | 2 | 0.6033 | 0.5225 | −1.3882 | −0.1978 |
| 3 | 0.9050 | 0.3 | 3 | 1.0450 | 0.35 | 3 | 1.2798 | 0.25 | 3 | 0.7389 | 0.6033 | −1.8215 | 0.8409 |
| 4 | 1.0450 | 0.3 | 4 | 1.2066 | 0.35 | 4 | 1.4778 | 0.25 | 4 | 0.8532 | 0.7389 | −1.2558 | 1.6342 |
| 5 | 1.1683 | 0.3 | 5 | 1.3491 | 0.35 | 5 | 1.6528 | 0.25 | 5 | 0.9050 | 0.8532 | −0.5034 | 0.9433 |
| 6 | 1.2798 | 0.3 | 6 | 1.4778 | 0.35 | 6 | 1.8100 | 0.25 | 6 | 1.0450 | 0.9050 | −2.8274 | 1.3816 |
| 7 | 1.3824 | 0.3 | 7 | 1.5962 | 0.35 | 7 | 1.9550 | 0.25 | 7 | 1.1683 | 1.0450 | −1.5604 | 2.8274 |
| 8 | 1.4778 | 0.3 | 8 | 1.7065 | 0.35 | 8 | 2.0900 | 0.25 | 8 | 1.2066 | 1.1583 | −1.1008 | 0.3246 |
| 9 | 1.5675 | 0.3 | 9 | 1.8100 | 0.35 | | | | 9 | 1.2798 | 1.2060 | −1.7686 | 1.0935 |
| 10 | 1.5523 | 0.3 | 10 | 1.9079 | 0.35 | | | | 10 | 1.3491 | 1.2798 | −1.1935 | 1.6973 |
| 11 | 1.7329 | 0.3 | 11 | 2.0010 | 0.35 | | | | 11 | 1.3824 | 1.3491 | −0.4401 | 1.0056 |
| 12 | 1.5100 | 0.3 | 12 | 2.0900 | 0.35 | | | | 12 | 1.4778 | 1.3824 | −2.8274 | 1.4449 |
| 13 | 1.3839 | 0.3 | | | | | | | 13 | 1.5676 | 1.4778 | −1.5297 | 2.8274 |
| 14 | 1.9550 | 0.3 | | | | | | | 14 | 1.5962 | 1.5075 | −1.0774 | 0.3553 |
| 15 | 2.0236 | 0.3 | | | | | | | 15 | 1.6523 | 1.5962 | −1.7462 | 1.1217 |
| 16 | 2.0900 | 0.3 | | | | | | | 16 | 1.7065 | 1.6523 | −1.1780 | 1.7095 |
| | | | | | | | | | 17 | 1.7329 | 1.7065 | −0.4229 | 1.0212 |
| | | | | | | | | | 18 | 1.8100 | 1.7329 | −2.8274 | 1.4621 |
| | | | | | | | | | 19 | 1.8839 | 1.8100 | −1.5181 | 2.8274 |
| | | | | | | | | | 20 | 1.9079 | 1.8839 | −1.0653 | 0.3669 |
| | | | | | | | | | 21 | 1.9550 | 1.9079 | −1.7410 | 1.1808 |
| | | | | | | | | | 22 | 2.0010 | 1.9550 | −1.1709 | 1.7148 |
| | | | | | | | | | 23 | 2.0236 | 2.0010 | −0.4149 | 1.0282 |
| | | | | | | | | | 24 | 2.0900 | 2.0236 | −2.8274 | 1.4701 |

With this example, the profile (1) fourth, eighth, twelfth, ... and the profile (2) third, sixth, ninth, ... zone diameters match. Between profiles (1) and (3), the profile (1) second, fourth, sixth, eighth, ... and the profile (3) first, second, third, fourth, ... zone diameters match. Furthermore, between profiles (2) and (3), the profile (2) third, sixth, ninth, ... and the profile (3) second, fourth, sixth, ... zone diameters match.

With the profiles synthesized based on this relationship, as shown in FIG. 22D, the steps of the blaze are at their maximum at the zones in front of and behind the point where all three profile zone diameters match (sixth, seventh and twelfth, thirteenth zones, ... continues thereafter). Also, the blaze steps are the next biggest at the zones in front of and behind the location where only profiles (1) and (3) match (third, fourth and ninth, tenth, ... continues thereafter). With this composite profile as well, a repeated structure appears for which the region for which all the three profile zone diameters match is the periodic unit.

FIG. 22E shows the intensity distribution of this composite profile. We can see that peaks are generated at the points corresponding to the set addition power of each profile. From this intensity distribution, the multi-focal lens of this example is useful as a multi-focal ophthalmic lens for near vision such as reading or the like, but also for which visual acuity is assured for a broad range from TV viewing distance to personal computer monitor distance. It also has value with use as an optical element that similarly requires multi-focal characteristics like those of the previous examples.

For this example, we will describe hereafter the characteristics of the synchronous structure when three or more profiles are synthesized as shown in the thirteenth mode with the Means for Solving the Problems section described previously. The addition power $P_2$ and $P_3$ of profile (2) and profile (3) are expressed with Equation 8 and Equation 21 noted above using the addition power $P_1$ of profile (1).

When a, b, d, and e of Equation 8 and Equation 21 are integers of zero or greater, and z is the greatest common divisor of (b×e), (a×e), and (b×d), there is a synchronous structure for which continuous zone pitches are mutually the same for (b×e)/z with the first zone profile, (a×e)/z with the second zone profile, and (b×d)/z with the third zone profile. In other words, with this example, since a=3, b=4, d=1, and e=2, (b×e)=8, (a×e)=6, and (b×d)=4, the quotients when each of these is divided by 2 which is the greatest common divisor are 4, 3, and 2, and the pitch of this number of zones is the same between any of the profiles. This synchronous structure is clear from FIGS. 22A, 22B, and 22C. Incidentally, with example 16, zone pitches counts of 3, 2, and 1 are synchronized in relation to profiles (1), (2), and (3) from that relational expression. In this way, by determining the addition power of the respective zones using the relational expressions of Equation 8 and Equation 21, it is possible to form a synchronous structure for three or more profiles.

[Example 18] (Example of Synthesis of Three or More Profiles (Part 3))

Other than the fact that a zone pitch was newly set based on the standard setting equation of Equation 20 with the addition power of profile (3) with example 17 noted above being set to $P_3=P_1\times(1/4)=1$ D, the specifications are the same as those of example 17. The phase constants of profiles (1), (2), and (3) are 0.4, 0.2, and 0.2. The details of each profile and the composite profile are shown in Table 18 and FIGS. 23A to 23D.

TABLE 18

[Example 18]

| | Profile (1) Addition power $P_1 = 4D$ | | | Profile (2) Addition power $P_2 = 3D$ | | | Profile (3) Addition power $P_3 = 1D$ | | | Composite profile (Example 18) | | | |
|---|---|---|---|---|---|---|---|---|---|---|---|---|---|
| | Zone | | | Zone | | | Zone | | | Zone radius (mm) | | | |
| Zone No. n | radius (mm) $r_n$ | Phase constant h | Zone No. m | radius (mm) $r_m$ | Phase constant h | Zone No. q | radius (mm) $r_q$ | Phase constant h | Zone No. i | Outer radius $r_i$ | Inner radius $r_{i-1}$ | Phase (radians) $\phi_i'$ | $\phi_{i-1}'$ |
| 1 | 0.5225 | 0.4 | 1 | 0.6033 | 0.2 | 1 | 1.0450 | 0.2 | 1 | 0.5225 | 0 | −1.7166 | 2.5133 |
| 2 | 0.7389 | 0.4 | 2 | 0.8532 | 0.2 | 2 | 1.4775 | 0.2 | 2 | 0.6033 | 0.5225 | −0.4075 | 0.7967 |
| 3 | 0.9050 | 0.4 | 3 | 1.0450 | 0.2 | 3 | 1.8100 | 0.2 | 3 | 0.7389 | 0.6033 | −1.5704 | 0.8491 |
| 4 | 1.0450 | 0.4 | 4 | 1.2066 | 0.2 | 4 | 2.0900 | 0.2 | 4 | 0.8532 | 0.7389 | −1.4994 | 0.9429 |
| 5 | 1.1683 | 0.4 | 5 | 1.3491 | 0.2 | | | | 5 | 0.9050 | 0.8532 | −1.4275 | −0.2427 |
| 6 | 1.2798 | 0.4 | 6 | 1.4778 | 0.2 | | | | 6 | 1.0450 | 0.9050 | −2.5133 | 1.0858 |
| 7 | 1.3824 | 0.4 | 7 | 1.5962 | 0.2 | | | | 7 | 1.1683 | 1.0450 | −1.3169 | 2.5133 |
| 8 | 1.4778 | 0.4 | 8 | 1.7065 | 0.2 | | | | 8 | 1.2066 | 1.1683 | −0.0763 | 1.1964 |
| 9 | 1.5675 | 0.4 | 9 | 1.8100 | 0.2 | | | | 9 | 1.2798 | 1.2056 | −1.3276 | 1.1804 |
| 10 | 1.6523 | 0.4 | 10 | 1.9079 | 0.2 | | | | 10 | 1.3491 | 1.2798 | −1.3229 | 1.1856 |
| 11 | 1.7329 | 0.4 | 11 | 2.0010 | 0.2 | | | | 11 | 1.3524 | 1.3491 | −1.3047 | −0.0563 |
| 12 | 1.8100 | 0.4 | 12 | 2.0900 | 0.2 | | | | 12 | 1.4778 | 1.3624 | −2.5133 | 1.2686 |
| 13 | 1.8839 | 0.4 | | | | | | | 13 | 1.5675 | 1.4778 | −1.2908 | 2.5133 |
| 14 | 1.9550 | 0.4 | | | | | | | 14 | 1.5962 | 1.5675 | −0.0440 | 1.2227 |
| 15 | 2.0236 | 0.4 | | | | | | | 15 | 1.6523 | 1.5962 | −1.2988 | 1.2127 |
| 16 | 2.0900 | 0.4 | | | | | | | 16 | 1.7065 | 1.6523 | −1.2971 | 1.2145 |
| | | | | | | | | | 17 | 1.7329 | 1.7065 | −1.2863 | −0.0404 |
| | | | | | | | | | 18 | 1.8100 | 1.7329 | −2.5133 | 1.2270 |
| | | | | | | | | | 19 | 1.8839 | 1.8100 | −1.2803 | 2.5133 |
| | | | | | | | | | 20 | 1.9079 | 1.8839 | −0.0309 | 1.2330 |
| | | | | | | | | | 21 | 1.9550 | 1.9079 | −1.2866 | 1.2257 |
| | | | | | | | | | 22 | 2.0010 | 1.9550 | −1.2868 | 1.2266 |
| | | | | | | | | | 23 | 2.0236 | 2.0010 | −1.2581 | −0.0291 |
| | | | | | | | | | 24 | 2.0900 | 2.0236 | −2.5133 | 1.2361 |

The same as the group of examples noted above (examples 16 and 17), this example also has the same synchronous structure shown in FIG. 23D. The intensity distribution of the composite profile is shown in FIG. 23E. We can see that a peak is generated at the points correlating to the set addition power of each profile.

[Example 19] (Example of Synthesis of Three or More Profiles (Part 4))

Profile (1) is the same as with the group of examples noted above (examples 16 to 18), and the respective zone pitches are set based on the standard setting equations Equation 12 and Equation 20 such that the addition power of profile (2) is $P_2 = P_1 \times (4/5) = 3.2$ D, and the addition power of profile (3) is $P_3 = P_1 \times (2/5) = 1.6$ D. The phase constants of profiles (1), (2), and (3) are respectively set to 0.4, 0.25, and 0.3. The details of each profile and the composite profile are shown in Table 19 and FIGS. 24A to 24D. Also, the intensity distribution is shown in FIG. 24E.

TABLE 19

[Example 19]

| | Profile (1) Addition power $P_1 = 4D$ | | | Profile (2) Addition power $P_2 = 3.2D$ | | | Profile (3) Addition power $P_3 = 1.6D$ | | | Composite profile (Example 19) | | | |
|---|---|---|---|---|---|---|---|---|---|---|---|---|---|
| | Zone | | | Zone | | | Zone | | | Zone radius (mm) | | | |
| Zone No. n | radius (mm) $r_n$ | Phase constant h | Zone No. m | radius (mm) $r_m$ | Phase constant h | Zone No. q | radius (mm) $r_q$ | Phase constant h | Zone No. i | Outer radius $r_i$ | Inner radius $r_{i-1}$ | Phase (radians) $\phi_i'$ | $\phi_{i-1}'$ |
| 1 | 0.5225 | 0.4 | 1 | 0.5842 | 0.25 | 1 | 0.8261 | 0.3 | 1 | 0.5225 | 0 | −2.1259 | 2.9845 |
| 2 | 0.7389 | 0.4 | 2 | 0.8261 | 0.25 | 2 | 1.1683 | 0.3 | 2 | 0.6842 | 0.5225 | −0.6353 | 0.3874 |
| 3 | 0.9050 | 0.4 | 3 | 1.0118 | 0.25 | 3 | 1.4309 | 0.3 | 3 | 0.7389 | 0.5842 | −2.2193 | 0.9355 |
| 4 | 1.0450 | 0.4 | 4 | 1.1683 | 0.25 | 4 | 1.6528 | 0.3 | 4 | 0.8261 | 0.7389 | −1.7912 | 0.2940 |
| 5 | 1.1683 | 0.4 | 5 | 1.3062 | 0.25 | 5 | 1.8478 | 0.3 | 5 | 0.9050 | 0.8261 | −0.6302 | 1.6646 |
| 6 | 1.2798 | 0.4 | 6 | 1.4309 | 0.25 | 6 | 2.0236 | 0.3 | 6 | 1.0118 | 0.9050 | −1.6266 | 1.8831 |
| 7 | 1.3524 | 0.4 | 7 | 1.5456 | 0.25 | | | | 7 | 1.0460 | 1.0113 | −1.0073 | 0.0442 |
| 8 | 1.4778 | 0.4 | 8 | 1.6623 | 0.25 | | | | 8 | 1.1683 | 1.0450 | −2.9845 | 1.4460 |
| 9 | 1.5875 | 0.4 | 9 | 1.7525 | 0.25 | | | | 9 | 1.2798 | 1.1683 | −1.5995 | 2.9845 |

TABLE 19-continued

[Example 19]

| | Profile (1) Addition power $P_1 = 4D$ | | | Profile (2) Addition power $P_2 = 3.2D$ | | | Profile (3) Addition power $P_3 = 1.6D$ | | | Composite profile (Example 19) | | | |
|---|---|---|---|---|---|---|---|---|---|---|---|---|---|
| | Zone | | | Zone | | | Zone | | | Zone radius (mm) | | | |
| Zone No. n | radius (mm) $r_n$ | Phase constant h | Zone No. m | radius (mm) $r_m$ | Phase constant h | Zone No. q | radius (mm) $r_q$ | Phase constant h | Zone No. i | Outer radius $r_i$ | Inner radius $r_{i-1}$ | Phase (radians) $\phi_i'$ | $\phi_{i-1}'$ |
| 10 | 1.6523 | 0.4 | 10 | 1.8473 | 0.25 | | | | 10 | 1.3062 | 1.2798 | −0.2231 | 0.9135 |
| 11 | 1.7329 | 0.4 | 11 | 1.9375 | 0.25 | | | | 11 | 1.3824 | 1.3062 | −2.0249 | 1.3477 |
| 12 | 1.8100 | 0.4 | 12 | 2.0236 | 0.25 | | | | 12 | 1.4309 | 1.3824 | −1.7488 | 0.4884 |
| 13 | 1.8839 | 0.4 | | | | | | | 13 | 1.4778 | 1.4309 | −0.5713 | 1.7069 |
| 14 | 1.9550 | 0.4 | | | | | | | 14 | 1.5456 | 1.4778 | −1.4612 | 1.9420 |
| 15 | 2.0236 | 0.4 | | | | | | | 15 | 1.5675 | 1.5456 | −1.0144 | 0.1099 |
| | | | | | | | | | 16 | 1.6523 | 1.5675 | −2.9846 | 1.4985 |
| | | | | | | | | | 17 | 1.7329 | 1.6523 | −1.5721 | 2.9845 |
| | | | | | | | | | 18 | 1.7525 | 1.7329 | −0.1937 | 0.9411 |
| | | | | | | | | | 19 | 1.8190 | 1.7525 | −2.0053 | 1.3771 |
| | | | | | | | | | 20 | 1.8473 | 1.8100 | −1.7404 | 0.5079 |
| | | | | | | | | | 21 | 1.3839 | 1.8473 | −0.5572 | 1.7153 |
| | | | | | | | | | 22 | 1.9375 | 1.8839 | −1.4438 | 1.9561 |
| | | | | | | | | | 23 | 1.9550 | 1.9376 | −0.9998 | 0.1270 |
| | | | | | | | | | 24 | 2.0236 | 1.9550 | −2.9845 | 1.5134 |

With the composite profile of this example as well, we can see that peaks are generated at points correlating to the set addition power of each respective profile. Also, with the phase constants set with this example, the near and two intermediate region peak strengths are almost equal. By having that intensity distribution, for example with an ophthalmic lens, this is an item that achieves balance of vision from near to a broad intermediate region.

[Example 20] (Example of Synthesis of Three or More Profiles (Part 5) When the Rational Number Denominator Differs)

Profile (1) is the same as with the group of examples noted above (examples 16 to 19), and the zone diameters are set based on the standard setting equations of Equation 12 and Equation 20 such that the addition power of profile (2) is $P_2 = P_1 \times (3/4) = 3$ D, and the addition power of profile (3) is $P_3 = P_1 \times (1/3) \approx 1.333$ D. The phase constants of profiles (1), (2), and (3) are respectively 0.3, 0.4, and 0.3. The details of each profile and the composite profile are shown in Table 20 and FIGS. 25A to 25D. Also, the intensity distribution is shown in FIG. 25E.

TABLE 20

[Example 20]

| | Profile (1) Addition power $P_1 = 4D$ | | | Profile (2) Addition power $P_2 = 3D$ | | | Profile (3) Addition power $P_3 = 1.333D$ | | | Composite profile (Example 20) | | | |
|---|---|---|---|---|---|---|---|---|---|---|---|---|---|
| | Zone | | | Zone | | | Zone | | | Zone radius (mm) | | | |
| Zone No. n | radius (mm) $r_n$ | Phase constant h | Zone No. m | radius (mm) $r_m$ | Phase constant h | Zone No. q | radius (mm) $r_q$ | Phase constant h | Zone No. i | Outer radius $r_i$ | Inner radius $r_{i-1}$ | Phase (radians) $\phi_i'$ | $\phi_{i-1}'$ |
| 1 | 0.5225 | 0.3 | 1 | 0.8033 | 0.4 | 1 | 0.9030 | 0.3 | 1 | 0.5225 | 0 | −2.0082 | 8.1416 |
| 2 | 0.7389 | 0.3 | 2 | 0.8532 | 0.4 | 2 | 1.2793 | 0.3 | 2 | 0.6033 | 0.5225 | −1.3323 | −0.1232 |
| 3 | 0.9050 | 0.3 | 3 | 1.0450 | 0.4 | 3 | 1.5875 | 0.3 | 3 | 0.7389 | 0.8033 | −1.8461 | 1.1810 |
| 4 | 1.0450 | 0.3 | 4 | 1.2066 | 0.4 | 4 | 1.8100 | 0.3 | 4 | 0.8532 | 0.7389 | −2.4463 | 0.2389 |
| 5 | 1.1883 | 0.3 | 5 | 1.3491 | 0.4 | 5 | 2.0236 | 0.3 | 5 | 0.9050 | 0.8532 | −1.8067 | 0.0670 |
| 6 | 1.2798 | 0.3 | 6 | 1.4778 | 0.4 | 6 | 2.2168 | 0.3 | 6 | 1.0450 | 0.9050 | −1.9606 | 2.4632 |
| 7 | 1.3824 | 0.3 | 7 | 1.5962 | 0.4 | 7 | 2.3944 | 0.3 | 7 | 1.1683 | 1.0450 | −1.9852 | 2.4376 |

TABLE 20-continued

[Example 20]

| | Profile (1) Addition power $P_1 = 4D$ | | | Profile (2) Addition power $P_2 = 3D$ | | | Profile (3) Addition power $P_3 = 1.333D$ | | Composite profile (Example 20) | | | | |
|---|---|---|---|---|---|---|---|---|---|---|---|---|---|
| | Zone | | | Zone | | | Zone | | Zone radius (mm) | | | |
| Zone No. n | Zone radius (mm) $r_n$ | Phase constant h | Zone No. m | Zone radius (mm) $r_m$ | Phase constant h | Zone No. q | Zone radius (mm) $r_q$ | Phase constant h | Zone No. i | Outer radius $r_i$ | Inner radius $r_{i-1}$ | Phase (radians) $\phi_i'$ | $\phi_{i-1}'$ |
| 8 | 1.4778 | 0.3 | 8 | 1.7065 | 0.4 | | | | 8 | 1.2066 | 1.1683 | −1.5383 | −0.1002 |
| 9 | 1.5675 | 0.3 | 9 | 1.8100 | 0.4 | | | | 9 | 1.2798 | 1.2066 | −1.9199 | 0.9770 |
| 10 | 1.6523 | 0.3 | 10 | 1.9070 | 0.4 | | | | 10 | 1.3491 | 1.2798 | −1.0979 | 1.8500 |
| 11 | 1.7329 | 0.3 | 11 | 2.0010 | 0.4 | | | | 11 | 1.3824 | 1.8491 | −0.0656 | 1.4154 |
| 12 | 1.8100 | 0.3 | 12 | 2.0900 | 0.4 | | | | 12 | 1.4778 | 1.8824 | −2.5541 | 1.8193 |
| 13 | 1.8839 | 0.3 | 13 | 2.1759 | 0.4 | | | | 13 | 1.5675 | 1.4778 | −2.5311 | 1.8441 |
| 14 | 1.9550 | 0.3 | 14 | 2.2574 | 0.4 | | | | 14 | 1.5962 | 1.5675 | −0.2347 | 1.2388 |
| 15 | 2.0236 | 0.3 | 15 | 2.3367 | 0.4 | | | | 15 | 1.6523 | 1.5962 | −0.6801 | 2.2786 |
| 16 | 2.0900 | 0.3 | | | | | | | 16 | 1.7085 | 1.6523 | −1.7185 | 1.2049 |
| 17 | 2.1543 | 0.3 | | | | | | | 17 | 1.7329 | 1.7065 | −0.6717 | 0.7947 |
| 18 | 2.2168 | 0.3 | | | | | | | 18 | 1.8100 | 1.7329 | −3.1416 | 1.3132 |
| 19 | 2.2775 | 0.3 | | | | | | | 19 | 1.8839 | 1.8100 | −1.2927 | 3.1416 |
| 20 | 2.3367 | 0.3 | | | | | | | 20 | 1.9079 | 1.8839 | −0.8716 | 0.5923 |
| | | | | | | | | | 21 | 1.9550 | 1.9079 | −1.2945 | 1.6416 |
| | | | | | | | | | 22 | 2.0010 | 1.9550 | −2.3210 | 0.5904 |
| | | | | | | | | | 23 | 2.0236 | 2.0010 | −1.2670 | 0.1923 |
| | | | | | | | | | 24 | 2.0900 | 2.0236 | −1.9043 | 2.5029 |
| | | | | | | | | | 25 | 2.1543 | 2.0900 | −1.9131 | 2.4939 |
| | | | | | | | | | 26 | 2.1753 | 2.1543 | −1.4868 | −0.0281 |
| | | | | | | | | | 27 | 2.2168 | 2.1753 | −1.8968 | 1.0267 |
| | | | | | | | | | 28 | 2.2574 | 2.2168 | −1.0657 | 1.8733 |
| | | | | | | | | | 29 | 2.2775 | 2.2574 | −0.0245 | 1.4476 |
| | | | | | | | | | 30 | 2.3367 | 2.2775 | −2.5292 | 1.8604 |

This example is an example for which with setting of the addition power of profiles (2) and (3), the number of denominators is made to be different when displaying with rational numbers. This is (3/4) with profile (2), and (1/3) with profile (3). Even in a case when the rational number denominators are made to be different as with this example, it is possible to know the details of the synchronous structure using the numeric expression for determining the addition power of each profile.

Specifically, with this example, a=3, b=4, d=1, and e=3 with Equation 8 and Equation 21, and from the relational expression of the synchronous structure described with example 17, (b×e)/z=12, (a×e)/z=9, and (b×d)/z=4 respectively in relation to profiles (1), (2), and (3). The synchronous structure has continuous zone pitches with these numerical values. This synchronous structure is clear from FIGS. 25A, 25B, and 25C. With synthesis of profiles with different denominators in this way as well, peaks are generated at points correlating to the set addition power of each profile (FIG. 25E).

[Example 21] (Example of Synthesis of Three or More Profiles (Part 6) Example 1 of Synthesizing Four Profiles)

Next, we will describe this synthesis example with four profiles. Profile (1) is the same as with the group of examples noted above (examples 16 to 20). Setting was done with the standard setting equations Equation 12 and Equation 20 such that with profile (2), the addition power is $P_2=P_1\times(3/4)=3$ D, and with profile (3), the addition power is $P_3=P_1\times(2/4)=2$ D. Also, with profile (4), the zone diameter is set with $P_3=P_4$ substituted in the standard setting equation of Equation 20 so that the addition power is $P_4=P_1\times(1/4)=1$ D. With the examples hereafter, when synthesizing four or more profiles, the setting of the zone pitch of the fourth, fifth and so on profiles is done substituting with the standard setting equation of Equation 20 which is the setting equation for the third zone profile, or with the general setting equation of Equation 18. The phase constants for profiles (1), (2), (3), and (4) are respectively set to 0.3, 0.3, 0.15, and 0.15. The composite profile is obtained by synthesizing the phase function of these four profiles. The details of profiles (1) to (4) and the composite profile are shown in Table 21 and FIGS. 26A to 26E.

TABLE 21

[Example 21]

| Profile (1) Addition power $P_1$ = 4D | | | Profile (2) Addition power $P_1$ = 3D | | | Profile (3) Addition power $P_1$ = 2D | | | Profile (4) Addition power $P_1$ = 1D | | | Composite profile (Example 21) | | | | |
|---|---|---|---|---|---|---|---|---|---|---|---|---|---|---|---|---|
| Zone | Zone radius (mm) | Phase constant | Zone | Zone radius (mm) | Phase constant | Zone | Zone radius (mm) | Phase constant | Zone | Zone radius (mm) | Phase constant | Zone | Zone radius (mm) Outer radius | Inner radius | Phase (radians) | |
| No. n | $r_n$ | h | No. m | $r_n$ | h | No. q | $r_n$ | h | No. u | $r_n$ | h | No. i | $r_i$ | $r_{i-1}$ | $\phi_i'$ | $\phi_{i-1}'$ |
| 1 | 0.5225 | 0.3 | 1 | 0.6033 | 0.3 | 1 | 0.7389 | 0.15 | 1 | 1.0450 | 0.15 | 1 | 0.5225 | 0 | −1.8376 | 2.8374 |
| 2 | 0.7369 | 0.3 | 2 | 0.8532 | 0.3 | 2 | 1.0450 | 0.15 | 2 | 1.4778 | 0.15 | 2 | 0.6033 | 0.5225 | −1.0752 | 0.0573 |
| 3 | 0.9053 | 0.3 | 3 | 1.0450 | 0.3 | 3 | 1.2798 | 0.15 | 3 | 1.8100 | 0.15 | 3 | 0.7389 | 0.6053 | −1.6892 | 0.8098 |
| 4 | 1.0453 | 0.3 | 4 | 1.2066 | 0.3 | 4 | 1.4778 | 0.15 | 4 | 2.0900 | 0.15 | 4 | 0.8532 | 0.7389 | −1.4765 | 1.1363 |
| 5 | 1.1683 | 0.3 | 5 | 1.3491 | 0.3 | 5 | 1.6523 | 0.15 | | | | 5 | 0.9050 | 0.6532 | −0.8939 | 0.4064 |
| 6 | 1.2796 | 0.3 | 6 | 1.4776 | 0.3 | 6 | 1.8100 | 0.15 | | | | 6 | 1.0450 | 0.9050 | −2.5274 | 0.9911 |
| 7 | 1.3824 | 0.3 | 7 | 1.5962 | 0.3 | 7 | 1.9550 | 0.15 | | | | 7 | 1.1683 | 1.0450 | −1.2693 | 2.8274 |
| 8 | 1.4778 | 0.3 | 8 | 1.7065 | 0.3 | 8 | 2.0900 | 0.15 | | | | 8 | 1.3056 | 1.1683 | −0.7059 | 0.6257 |
| 9 | 1.5675 | 0.3 | 9 | 1.8100 | 0.3 | | | | | | | 9 | 1.2798 | 1.2066 | −1.4801 | 1.1790 |
| 10 | 1.6523 | 0.3 | 10 | 1.9079 | 0.3 | | | | | | | 10 | 1.3891 | 1.2798 | −1.3217 | 1.3473 |
| 11 | 1.7329 | 0.3 | 11 | 2.0010 | 0.3 | | | | | | | 11 | 1.3824 | 1.3491 | −0.7680 | 0.5632 |
| 12 | 1.8100 | 0.3 | 12 | 2.0900 | 0.3 | | | | | | | 12 | 1.4778 | 1.3824 | −2.8274 | 1.1169 |
| 13 | 1.6839 | 0.3 | | | | | | | | | | 13 | 1.8675 | 1.4778 | −1.2233 | 2.8274 |
| 14 | 1.9550 | 0.3 | | | | | | | | | | 14 | 1.5962 | 1.5573 | −0.6727 | 0.6616 |
| 15 | 2.0236 | 0.3 | | | | | | | | | | 15 | 1.6523 | 1.5962 | −1.4532 | 1.2122 |
| 16 | 2.0903 | 0.3 | | | | | | | | | | 16 | 1.7065 | 1.6523 | −1.2956 | 1.3743 |
| | | | | | | | | | | | | 17 | 1.7329 | 1.7065 | −0.7451 | 0.5883 |
| | | | | | | | | | | | | 18 | 1.8100 | 1.7329 | −2.8274 | 1.1398 |
| | | | | | | | | | | | | 19 | 1.8839 | 1.8100 | −1.3095 | 2.8274 |
| | | | | | | | | | | | | 20 | 1.9079 | 1.6839 | −0.6595 | 0.6755 |
| | | | | | | | | | | | | 21 | 1.9550 | 1.9079 | −1.4418 | 1.2255 |
| | | | | | | | | | | | | 22 | 2.0010 | 1.9550 | −1.2856 | 1.3856 |
| | | | | | | | | | | | | 23 | 2.0236 | 2.0010 | −0.7347 | 0.5994 |
| | | | | | | | | | | | | 24 | 2.0900 | 2.0236 | −2.8274 | 1.1502 |

Even when the number of starting profiles is increased to four, the blase step becomes the maximum size at the zones in front of and behind the point for which all the zone diameters of each profile match (sixth, seventh, twelfth, thirteenth, eighteenth, nineteenth, and so on of the composite profile). A repeated structure appears that has as the periodic unit the region for which all the zone diameters of the four profiles match. The intensity distribution of that composite profile is shown in FIG. 26F. We can see that peaks are generated at the points correlating to the set addition power of each profile. Also, the peak intensity of the three intermediate regions with combining of the phase constants of this example are almost equal. The profiles that give this intensity distribution generate further many focal points, so this is useful as an ophthalmic lens that can ensure vision for a broad region.

Also, as with this example, by further increasing the number of zone profiles constituting the composite profile by mutually overlapping them compared to the examples noted previously, the number of focal points also increases accordingly, so the value of use increases as various types of optical elements for other optical fields in addition to as an ophthalmic lens.

[Example 22] (Example of Synthesis of Three or More Profiles (Part 7) Example 2 of Synthesizing Four Profiles)

Profile (1) is the same as with the group of examples noted above (examples 16 to 21). The zone pitches of the respective profiles were set using the standard setting equations of Equation 12 and Equation 20 such that with profile (2), the addition power is $P_2=P_1\times(4/5)=3.2$ D, with profile (3), the addition power is $P_3=P_1\times(2/5)=1.6$ D, and with profile (4), the addition power is $P_4=P_1\times(1/5)=0.8$ D. The phase constants of profiles (1), (2), (3), and (4) are set respectively at 0.4, 0.2, 0.2, and 0.2.

The composite profile was obtained by adding the phase functions of the four profiles. The details of profiles (1) to (4) and the composite profile are shown in Table 22 and FIGS. 27A to 27E.

TABLE 22

[Example 22]

| | Profile (1) Addition power $P_1$ = 4D | | | Profile (2) Addition power $P_1$ = 3.2D | | | Profile (3) Addition power $P_1$ = 1.6D | | | Profile (4) Addition power $P_1$ = 0.8D | | Composite profile (Example 22) | | | | |
|---|---|---|---|---|---|---|---|---|---|---|---|---|---|---|---|---|
| | Zone | | | Zone | | | Zone | | | Zone | | Zone | Zone radius (mm) | | Phase (radians) | |
| Zone No. n | radius (mm) $r_n$ | Phase constant h | Zone No. m | radius (mm) $r_n$ | Phase constant h | Zone No. q | radius (mm) $r_n$ | Phase constant h | Zone No. u | radius (mm) $r_n$ | Phase constant h | No. i | Outer radius $r_i$ | Inner radius $r_{i-1}$ | $\phi_i'$ | $\phi_{i-1}'$ |
| 1 | 0.5225 | 0.4 | 1 | 0.5842 | 0.2 | 1 | 0.8261 | 0.2 | 1 | 1.1683 | 0.2 | 1 | 0.5225 | 0 | −1.6524 | 3.1415 |
| 2 | 0.7389 | 0.4 | 2 | 0.8261 | 0.2 | 2 | 1.1683 | 0.2 | 2 | 1.6523 | 0.2 | 2 | 0.5842 | 0.5225 | −0.3481 | 0.6509 |
| 3 | 0.9050 | 0.4 | 3 | 1.0118 | 0.2 | 3 | 1.4309 | 0.2 | 3 | 2.0236 | 0.2 | 3 | 0.6745 | 0.5842 | −0.8449 | 0.9085 |
| 4 | 1.0450 | 0.4 | 4 | 1.1683 | 0.2 | 4 | 1.6523 | 0.2 | | | | 4 | 0.7889 | 0.6745 | −2.0941 | −0.8449 |
| 5 | 1.1683 | 0.4 | 5 | 1.3062 | 0.2 | 5 | 1.8473 | 0.2 | | | | 5 | 0.8261 | 0.7389 | −1.5802 | 0.4192 |
| 6 | 1.2798 | 0.4 | 6 | 1.4389 | 0.2 | 6 | 2.0236 | 0.2 | | | | 6 | 0.9053 | 0.8261 | −1.1683 | 0.9331 |
| 7 | 1.3824 | 0.4 | 7 | 1.5456 | 0.2 | | | | | | | 7 | 0.9539 | 0.9350 | −0.0976 | 1.8450 |
| 8 | 1.4778 | 0.4 | 8 | 1.6523 | 0.2 | | | | | | | 8 | 1.0118 | 0.9539 | −1.8027 | −0.0976 |
| 9 | 1.5675 | 0.4 | 9 | 1.7585 | 0.2 | | | | | | | 9 | 1.0450 | 1.0118 | −1.5557 | −0.5461 |
| 10 | 1.5523 | 0.4 | 10 | 1.8473 | 0.2 | | | | | | | 10 | 1.1683 | 1.0450 | −3.1415 | 0.9475 |
| 11 | 1.7329 | 0.4 | 11 | 1.9375 | 0.2 | | | | | | | 11 | 1.2796 | 1.1683 | −1.2111 | 0.1416 |
| 12 | 1.8100 | 0.4 | 12 | 2.0236 | 0.2 | | | | | | | 12 | 1.3088 | 1.2496 | 0.2201 | 1.3022 |
| 13 | 1.8839 | 0.4 | | | | | | | | | | 13 | 1.3491 | 1.3082 | −0.3213 | 1.4767 |
| 14 | 1.9550 | 0.4 | | | | | | | | | | 14 | 1.3824 | 1.3491 | −1.7195 | −0.3213 |
| 15 | 2.0236 | 0.4 | | | | | | | | | | 15 | 1.4309 | 1.3824 | −1.3311 | 0.7937 |
| | | | | | | | | | | | | 16 | 1.4778 | 1.4309 | −0.9561 | 1.1622 |
| | | | | | | | | | | | | 17 | 1.5083 | 1.4778 | 0.1166 | 1.5572 |
| | | | | | | | | | | | | 18 | 1.5455 | 1.5063 | −1.6441 | 0.1166 |
| | | | | | | | | | | | | 19 | 1.5675 | 1.5456 | −1.4416 | −0.3874 |
| | | | | | | | | | | | | 20 | 1.6523 | 1.5675 | −3.1416 | 1.0716 |
| | | | | | | | | | | | | 21 | 1.7529 | 1.6523 | −1.1754 | 3.1416 |
| | | | | | | | | | | | | 22 | 1.7525 | 1.7529 | 0.2613 | 1.3379 |
| | | | | | | | | | | | | 23 | 1.7847 | 1.7525 | −0.2733 | 1.5179 |
| | | | | | | | | | | | | 24 | 1.8100 | 1.7847 | −1.6834 | −0.2733 |
| | | | | | | | | | | | | 25 | 1.8473 | 1.8100 | −1.3009 | 0.8899 |
| | | | | | | | | | | | | 26 | 1.8839 | 1.8473 | −0.9361 | 1.2124 |
| | | | | | | | | | | | | 27 | 1.9079 | 1.8839 | 0.1523 | 1.5872 |
| | | | | | | | | | | | | 28 | 1.9375 | 1.9079 | −1.6164 | 0.1523 |
| | | | | | | | | | | | | 29 | 1.9550 | 1.9375 | −1.4195 | −0.3597 |
| | | | | | | | | | | | | 30 | 2.0336 | 1.9550 | −3.1416 | 1.0938 |

This example is an example when the rational number denominator of each profile is 5, and a repeated structure appears for which the periodic unit is the region for which all the zone diameters of the four profiles match. The intensity distribution of the composite profile (FIG. 27F) has peaks generated at points correlating to the set addition power of each profile. This example has four zone profiles synthesized, the same as with example 21, but the addition power of each zone profile is varied and set, and we can see that each focal point peak is generated at different positions from those of example 21. In this way, the setting of each peak position can be performed freely even with the number of starting profiles increased.

[Example 23] (Example of Synthesis of Three or More Profiles (Part 8) Example of Synthesizing Five Profiles)

This example is an example when five profiles are synthesized. Profile (1) is the same as with the group of examples noted above (examples 16 to 22). The zone diameters of the respective profiles were set using the standard setting equations of Equation 12 and Equation 20 such that with profile (2), the addition power is $P_2=P_1\times(4/5)=3.2$ D, with profile (3), the addition power is $P_3=P_1\times(3/5)=2.4$ D, with profile (4), the addition power is $P_4=P_1\times(2/5)=1.6$ D, and with profile (5), the addition power is $P_5=P_1\times(1/5)=0.8$ D. The phase constants of profiles (1), (2), (3), (4), and (5) are respectively set at 0.4, 0.25, 0.25, 0.1, and 0.1.

The composite profile was obtained by synthesizing the phase functions of those five profiles. The details of profiles (1) to (5) and the composite profile are shown in Table 23 and FIGS. 28A to 28F.

TABLE 23

[Example 23]

| Profile (1) Addition power $P_1$ = 4D | | | Profile (2) Addition power $P_1$ = 3.2D | | | Profile (3) Addition power $P_1$ = 2.4D | | | Profile (4) Addition power $P_1$ = 1.6D | | |
|---|---|---|---|---|---|---|---|---|---|---|---|
| Zone No. n | Zone radius (mm) $r_n$ | Phase constant h | Zone No. m | Zone radius (mm) $r_n$ | Phase constant h | Zone No. q | Zone radius (mm) $r_n$ | Phase constant h | Zone No. q | Zone radius (mm) $r_n$ | Phase constant h |
| 1 | 0.5225 | 0.4 | 1 | 0.5842 | 0.25 | 1 | 0.8745 | 0.25 | 1 | 0.8261 | 0.1 |
| 2 | 0.7389 | 0.4 | 2 | 0.8261 | 0.25 | 2 | 0.9639 | 0.25 | 2 | 1.1683 | 0.1 |
| 3 | 0.9050 | 0.4 | 3 | 1.0118 | 0.25 | 3 | 1.1663 | 0.25 | 3 | 1.4309 | 0.1 |
| 4 | 1.0450 | 0.4 | 4 | 1.1683 | 0.25 | 4 | 1.3491 | 0.25 | 4 | 1.6523 | 0.1 |
| 5 | 1.1683 | 0.4 | 5 | 1.3062 | 0.25 | 5 | 1.5083 | 0.25 | 5 | 1.8473 | 0.1 |
| 6 | 1.2798 | 0.4 | 6 | 1.4309 | 0.25 | 6 | 1.6523 | 0.25 | 6 | 2.0236 | 0.1 |
| 7 | 1.3824 | 0.4 | 7 | 1.5456 | 0.25 | 7 | 1.7847 | 0.25 | | | |
| 8 | 1.4778 | 0.4 | 8 | 1.6523 | 0.25 | 8 | 1.9079 | 0.25 | | | |
| 9 | 1.5675 | 0.4 | 9 | 1.7525 | 0.25 | 9 | 2.0236 | 0.25 | | | |
| 10 | 1.6523 | 0.4 | 10 | 1.8473 | 0.25 | | | | | | |
| 11 | 1.7329 | 0.4 | 11 | 1.9375 | 0.25 | | | | | | |
| 12 | 1.8100 | 0.4 | 12 | 2.0236 | 0.25 | | | | | | |
| 13 | 1.8839 | 0.4 | | | | | | | | | |
| 14 | 1.9550 | 0.4 | | | | | | | | | |
| 15 | 2.0236 | 0.4 | | | | | | | | | |

| Profile (5) Addition power $P_1$ = 0.8D | | | Composite profile (Example 23) | | | |
|---|---|---|---|---|---|---|
| Zone No. q | Zone radius (mm) $r_n$ | Phase constant h | Zone No. i | Outer radius $r_i$ | Inner radius $r_{i-1}$ | Phase (radians) $\phi_i'$ \ $\phi_{i-1}'$ |
| 1 | 1.1683 | 0.1 | 1 | 0.5225 | 0 | −2.3576 \ 3.4558 |
| 2 | 1.6523 | 0.1 | 2 | 0.5842 | 0.5225 | −0.9500 \ 0.1557 |
| 3 | 2.0236 | 0.1 | 3 | 0.6745 | 0.5842 | −1.3431 \ 0.6306 |
| | | | 4 | 0.7399 | 0.6745 | −1.3854 \ 0.2277 |
| | | | 5 | 0.8261 | 0.7389 | −1.3590 \ 1.1288 |
| | | | 6 | 0.9050 | 0.8261 | −1.6517 \ 0.5392 |
| | | | 7 | 0.9829 | 0.9050 | −0.8228 \ 0.9616 |
| | | | 8 | 1.0118 | 0.9539 | −1.3417 \ 0.7480 |
| | | | 9 | 1.0450 | 1.0118 | −1.0214 \ 0.2391 |
| | | | 10 | 1.1683 | 1.0450 | −3.4558 \ 1.4918 |
| | | | 11 | 1.3798 | 1.1683 | −1.7085 \ 3.4558 |
| | | | 12 | 1.3062 | 1.2798 | −0.4694 \ 0.8048 |
| | | | 13 | 1.3491 | 1.3062 | −1.0187 \ 1.1014 |
| | | | 14 | 1.3824 | 1.3491 | −1.1358 \ 0.5521 |
| | | | 15 | 1.4309 | 1.3824 | −1.1691 \ 1.3775 |
| | | | 16 | 1.4778 | 1.4309 | −1.5057 \ 1.0300 |
| | | | 17 | 1.5083 | 1.4778 | −0.6910 \ 1.0076 |
| | | | 18 | 1.5456 | 1.5083 | −1.2353 \ 0.6798 |
| | | | 19 | 1.5875 | 1.5456 | −0.9318 \ 0.3365 |
| | | | 20 | 1.6523 | 1.5675 | −3.4558 \ 1.5815 |
| | | | 21 | 1.7829 | 1.6523 | −1.6746 \ 3.4558 |
| | | | 22 | 1.7525 | 1.7329 | −0.4354 \ 0.8387 |
| | | | 23 | 1.7847 | 1.7525 | −0.9880 \ 1.1554 |
| | | | 24 | 1.8100 | 1.7847 | −1.1975 \ 0.5843 |
| | | | 25 | 1.8173 | 1.8100 | −1.1411 \ 1.4058 |
| | | | 26 | 1.8839 | 1.8473 | −1.4890 \ 1.0581 |
| | | | 27 | 1.9079 | 1.8839 | −0.6670 \ 1.0313 |
| | | | 28 | 1.9375 | 1.9079 | −1.2140 \ 0.9037 |
| | | | 29 | 1.9650 | 1.9375 | −0.9127 \ 0.3688 |
| | | | 30 | 2.0236 | 1.9550 | −3.4558 \ 1.6006 |

The blaze steps are at maximum size at the points for which the zone diameters of each profile all match, even when the number of starting profiles is increased to five (tenth, eleventh, twentieth, twenty-first, and so on of the composite profile). Also, a repeated structure appears for which the period unit is the region for which the zone diameters of the five profiles all match. The intensity distribution of that composite profile is shown in FIG. 28G.

From the intensity distribution diagram of this example, we can see that peaks are generated at points correlating to the set addition power of each profile. Therefore, an item having this composite profile, equipped with a plurality of focal point positions, the same as example 22 noted above and the like, can have the plurality of required focal points set efficiently and with good precision, and can also be used as another optical element, not just as an ophthalmic lens.

Next, we will describe the specifications of a multi-focal lens for which the adjustment method of the intensity distribution on the optical axis and the strength ratio of the focal point peaks of the diffractive multi-focal lens of the present invention are varied. Specifically, as the method of varying the peak strength ratio of the diffractive multi-focal lens of the present invention, we will describe a method of varying the phase constants of each starting profile based on the examples hereafter.

[Example 24] (Example of Method for Controlling Intensity Distribution with the Phase Constant of the Starting Profiles Varied)

Figure 11D:
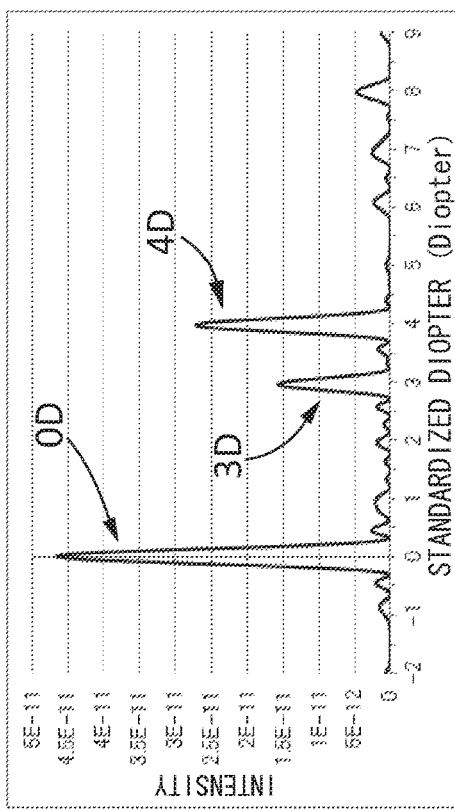

The composite profile was obtained by varying the phase constants of profiles (1) and (2) which are the starting profiles in order to vary the strength ratio of the near region peak (4 D) and the intermediate region peak (3 D) of the composite profile of example 6. As shown in Table 24, when the phase constants are varied, the intensity distributions are respectively shown in FIGS. 29A, 29B, 29C, and 29D. FIG. 29A is the same as the item in FIG. 11D of example 6. With example 6, the peak intensity of the intermediate region is set low.

The intensity distribution of the composite profile when the phase constants of profiles (1) and (2) of example 6 are varied as 0.3 and 0.4 respectively is shown in FIG. 29B. In this case, the peak strength of the intermediate region is greater than the peak strength of the near region. Items with this profile structure have specifications for an ophthalmic lens for the many users who work with personal computers.

When the phase constants are varied at 0.35 and 0.35, the intensity distribution is as shown in FIG. 29C. The peak strength of near and intermediate are approximately equal. In this case, this is one lens specification for which the visions for near work and intermediate work are approximately equal.

Furthermore, when the phase constants are varied at 0.45 and 0.4, the peak strengths for far, intermediate and near are approximately equal. In this case, this is a lens specification for which balance is achieved so that the respective visions for the far, near, and intermediate regions are approximately equal. It is possible to vary freely the strength of each peak by varying the phase constants of the starting profiles in this way.

TABLE 24

[Example 24] Combination of phase constant of starting profiles

| | Profile (1) | Profile (2) | Note |
|---|---|---|---|
| Phase constant (h) | 0.4 | 0.3 | FIG. 28A (Example 6) |
| | 0.3 | 0.4 | FIG. 28B |
| | 0.35 | 0.35 | FIG. 28C |
| | 0.45 | 0.4 | FIG. 28D |

Furthermore, the phase constants can also be constant for the entire zone region of the starting profiles, or can be partially different. For example, it is possible to have the peak intensity of the intermediate focal point for when the aperture diameter is small be low, and to have the peak intensity of the intermediate focal point be high for when the aperture diameter is large by varying the phase constants of the starting profiles among the different regions. The method for controlling the intensity distribution when varying the phase constants of the starting profiles among the different regions and the lens specification obtained by this are described based on example 25.

[Example 25] (Example of Varying the Phase Constants of the Starting Profile)

A composite profile was obtained with the phase constants of profiles (1) and (2) constituting from the first to seventh zones of the composite profile of example 6 respectively set at 0.45 and 0.15, and with the phase constants of profiles (1) and (2) constituting from the eighth to nineteenth zones respectively set at 0.4 and 0.5.

Figure 30A:
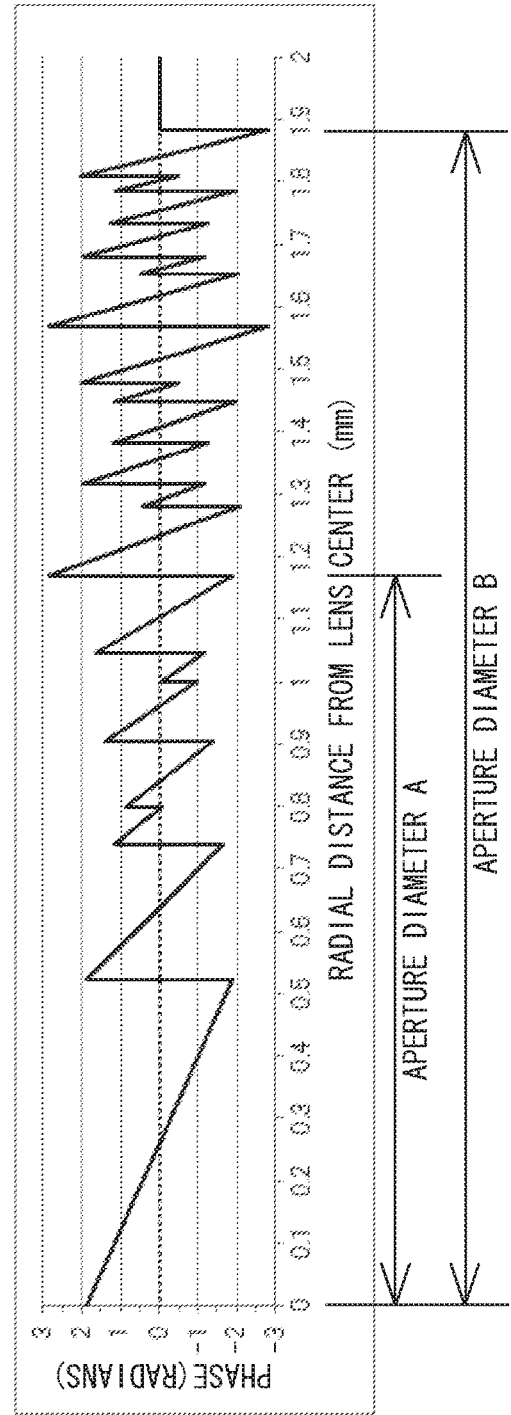
FIGS. 30A-30C are drawings relating to the diffractive multi-focal lens as example 25 of the present invention, where
Figure 30C:
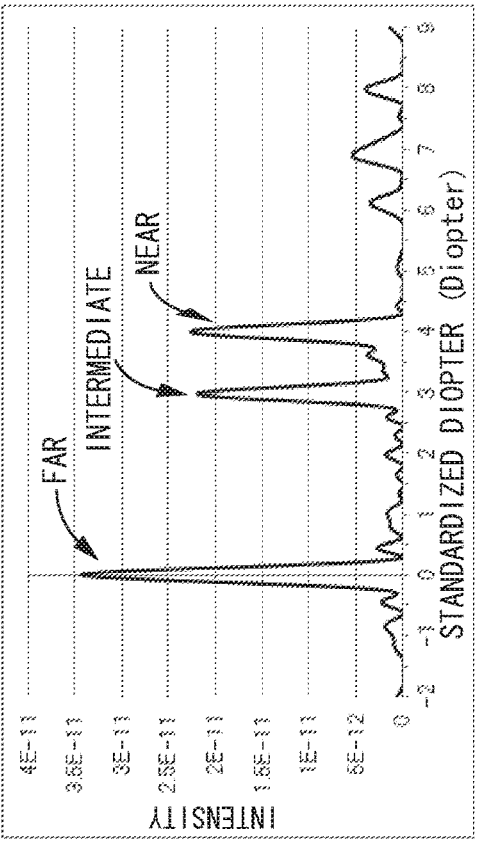
Figure 30B:
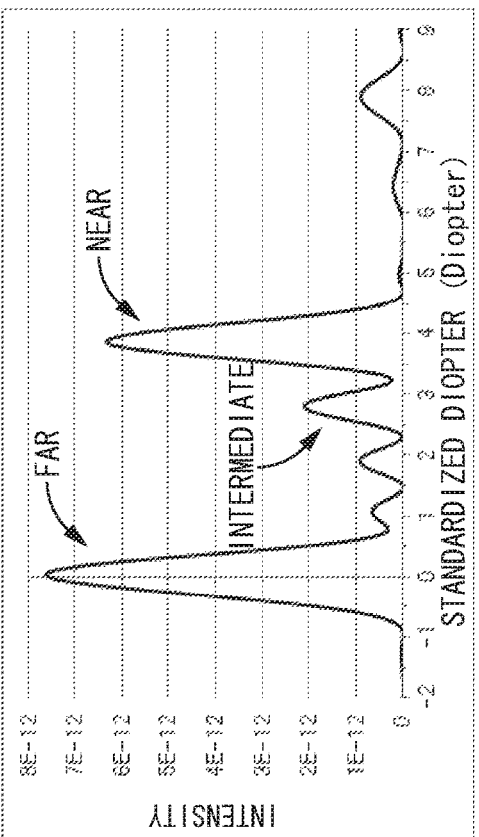

The details of the composite profile are shown in Table 25 and FIG. 30A. In the drawing, the region noted as aperture diameter A is the region for which the phase constants of profiles (1) and (2) are set to 0.45 and 0.15, and the aperture diameter B shows the overall region including the region for which the phase constants of profiles (1) and (2) are set as 0.4 and 0.5. The intensity distribution for the zones from the first to seventh, and up to the nineteenth of the profiles are respectively shown in FIGS. 30B and 30C.

With the aperture diameter A region, the intensity distribution has the peak intensity of the intermediate region set low. This region corresponds to the pupil diameter in an environment with high illuminance such as outdoors in fine weather, and in this environment, there are cases when it is possible to not have the peak strength of the intermediate region be that high, with the setting specifications made as necessary.

In the aperture diameter B region, an intermediate focal point peak is clearly formed. In other words, when the pupil dilates when the illuminance decreases, this is a lens specification that will ensure clear intermediate visual acuity. By partially varying the phase constant of the starting profiles in this way as well, it is possible to have specifications of an ophthalmic lens for giving suitable intensity distribution in accordance with the environment.

TABLE 25

[Example 25]

Composite profile

| | Zone radius (mm) | | Phase (radians) | | Profile (1) | Profile (2) |
|---|---|---|---|---|---|---|
| Zone No. i | Outer radius $r_i$ | Inner radius $r_{i-1}$ | $\phi_i'$ | $\phi_{i-1}'$ | Phase constant | Phase constant |
| 1 | 0.5225 | 0 | −1.8850 | 1.8850 | 0.45 | 0.15 |
| 2 | 0.7389 | 0.5225 | −1.6825 | 1.8850 | | |
| 3 | 0.7981 | 0.7389 | −0.0655 | 1.1449 | | |
| 4 | 0.9050 | 0.7981 | −1.4401 | 0.8770 | | |
| 5 | 1.0005 | 0.9050 | −0.9865 | 1.3873 | | |
| 6 | 1.0450 | 1.0005 | −1.1923 | −0.0440 | | |
| 7 | 1.1683 | 1.0450 | −1.8850 | 1.6351 | | |
| 8 | 1.2798 | 1.1683 | −2.0758 | 2.8274 | 0.4 | 0.5 |
| 9 | 1.3149 | 1.2798 | −1.1737 | 0.4375 | | |
| 10 | 1.3824 | 1.3149 | −1.2941 | 1.9679 | | |
| 11 | 1.4467 | 1.3824 | −2.0081 | 1.2192 | | |
| 12 | 1.4778 | 1.4467 | −0.4953 | 1.1335 | | |
| 13 | 1.5675 | 1.4778 | −2.8274 | 2.0180 | | |
| 14 | 1.6523 | 1.5675 | −2.0620 | 2.8274 | | |
| 15 | 1.6796 | 1.6523 | −1.1653 | 0.1413 | | |
| 16 | 1.7329 | 1.6796 | −1.2805 | 1.9763 | | |
| 17 | 1.7847 | 1.7329 | −2.0017 | 1.2328 | | |
| 18 | 1.8100 | 1.7847 | −0.4874 | 1.1399 | | |
| 19 | 1.8839 | 1.8100 | −2.8274 | 2.0259 | | |

As can be seen from examples 24 and 25 noted above, by varying the phase constant of the starting profiles, it is possible to control the peak intensity of each region as desired. The value of the phase constant of the starting profile is not necessarily set in a specific range when obtaining the target intensity distribution, but in fact it is possible to selectively set an item that will give a suitably desirable combination with the phase constants of other starting profiles or the like. In addition, it is also possible to vary the phase shift with Equation 22 as another method for varying the phase of the starting profile.

Above, we gave a detailed description of the embodiments of carrying out the present invention while showing a number of representative examples, but the present invention is not to be interpreted as being limited by those specific noted contents, and it is possible to add various changes, revisions, improvements or the like based on the knowledge of a person skilled in the art, and any such mode is included in the scope of the claims of the invention as long as it does not stray from the gist of the invention.

For example, the diffractive structure that realizes the zone profiles set with phase adjustment implemented can be set on either the front surface or back surface of the target optical lens. It is also possible to install it on the lens interior, and for example as noted in Japanese Unexamined Patent Publication No. JP-A-2001-042112, it is also possible to form the diffractive structure of the present invention on a laminated surface comprising two materials for which the refractive index is different.

Also, for the lens for which the present invention can be applied as well, this is not limited to being an ophthalmic lens, and it can be applied to a multi-focal optic lens or the like for an electrical device, a mechanical device or the like in addition to for a generally optical device. As the ophthalmic lens to which the present invention is applied, specific subjects can include contact lenses, glasses, intraocular lenses or the like, and subjects can also include a cornea insertion lens, an artificial cornea or the like for correcting vision embedded substantially within the cornea. Also, with contact lenses, it is possible to suitably use these for hard contact lenses that are hard and oxygen permeable, soft contact lenses that are hydrogel or non-hydrogel, soft contact lenses that are oxygen permeable hydrogel or non-hydrogel containing a silicon component, or the like. For intraocular lenses as well, it is possible to suitably use these for any intraocular lens such as a hard intraocular lens, a soft intraocular lens that can be bent and inserted in the eye, and the like.

The invention claimed is:

1. A diffractive multi-focal lens comprising a diffractive structure comprising a plurality of zones in a concentric circle form, the diffractive structure including an overlapping region for which at least two zone profiles are overlapped on the same region in at least a portion thereof, wherein
   at the overlapping region, at least a portion of a first zone profile of the at least two zone profiles has a zone pitch expressed by Equation 1, and at least a portion of a second zone profile of the at least two zone profiles has a zone pitch expressed by Equation 2, and an addition power $P_1$ given by the first zone profile and an addition power $P_2$ given by the second zone profile are determined by a relational expression of Equation 3, where a and b are mutually different integers of zero or greater, while quotients when a and b are divided by a mutual greatest common divisor thereof are both an integer other than 1, and a value of a/b is a value that cannot be expressed by a natural number X or by 1/X, and
   the overlapping region generates at least three focal points $$r_n = \sqrt{r_1^2 + \frac{2\lambda(n-1)}{P_1}}$$ [Equation 1]

$\lambda$: Design wavelength
$r_n$: nth zone radius of the first zone profile
$r_1$: First zone radius of the first zone profile
$P_1$: Addition power of the first zone profile
n: Natural number $$r_m = \sqrt{r_1'^2 + \frac{2\lambda(m-1)}{P_2}}$$ [Equation 2]

$\lambda$: Design wavelength
$r_m$: mth zone radius of the second zone profile
$r_1'$: First zone radius of the second zone profile
$P_2$: Addition power of the second zone profile
m: Natural number $$P_2 = \frac{a}{b} \times P_1.$$ [Equation 3]

2. The diffractive multi-focal lens according to claim 1, wherein a and b in Equation 3 are set to be a/b>1/2.

3. The diffractive multi-focal lens according to claim 1, wherein in regards to a and b in Equation 3, a synchronous structure, for which a b-number of zone pitches that are continuous in the first zone profile and an a-number of zone pitches that are continuous in the second zone profile are mutually the same within the same region, is set for at least a portion of the overlapping region of the diffractive structure.

4. The diffractive multi-focal lens according to claim 1, wherein a first zone radius $r_1$ of the first zone profile and a first zone radius $r_1'$ of the second zone profile are expressed respectively by Equation 4 and Equation 5

$$r_1 = \sqrt{\frac{2\lambda}{P_1}}$$ [Equation 4]

$$r_1' = \sqrt{\frac{2\lambda}{P_2}}.$$ [Equation 5]

5. The diffractive multi-focal lens according to claim 1, wherein the diffractive structure comprises a relief structure reflecting an optical path length correlating to a phase.

6. The diffractive multi-focal lens according to claim 1, wherein the diffractive multi-focal lens is an ophthalmic lens.

7. The diffractive multi-focal lens according to claim 1, wherein the at least three focal points are generated with a lens aperture diameter of a predetermined setting diameter or greater.

8. The diffractive multi-focal lens according to claim 1, wherein in the overlapping region, at least one type of equal-pitch zone is provided for which two or more zones are provided at equal pitches on at least one of the first zone profile and the second zone profile.

9. The diffractive multi-focal lens according to claim 8, wherein the equal-pitch zone is provided adjacent in a lens radial direction in relation to at least one of the region for which the zone pitch is represented by Equation 1 with the first zone profile, and the region for which the zone pitch is represented by Equation 2 with the second zone profile.

10. The diffractive multi-focal lens according to claim 8, wherein the at least one type of equal-pitch zone comprises a plurality of types of equal-pitch zones for which mutually different zone pitches are set.

11. The diffractive multi-focal lens according to claim 1, wherein the diffractive multi-focal lens is an ophthalmic lens for which of the three focal points, one focal point is used for far vision, and another focal point is used for near vision, and the other focal point is used for intermediate vision.

12. The diffractive multi-focal lens according to claim 11, wherein the focal point for far vision is given by a 0th order diffracted light of the diffractive structure, and the focal point for near vision and the focal point for intermediate vision are given by a +1 order diffracted light by the first zone profile and the second zone profile.

13. The diffractive multi-focal lens according to claim 1, wherein with a position of an outer diameter radius of an nth zone, n being a natural number, of the first zone profile being a boundary radius position,
  at one side of an inner circumference side and an outer circumference side of the boundary radius position, the diffractive structure of the first zone profile is provided but the diffractive structure of the second zone profile is not provided, and
  at the other side of the inner circumference side and the outer circumference side of the boundary radius position, the diffractive structure for which the first zone profile and the second zone profile are overlapped is provided.

14. The diffractive multi-focal lens according to claim 13, wherein
  at the inner circumference side of the boundary radius position, the diffractive structure of the first zone profile is provided but the diffractive structure of the second zone profile is not provided, and
  at the outer circumference side of the boundary radius position, the diffractive structure for which the first zone profile and the second zone profile are overlapped is provided.

15. The diffractive multi-focal lens according to claim 1, wherein in addition to the first zone profile and the second zone profile, a third zone profile is set, and the diffractive structure includes the first, second, and third zone profiles overlapped on the same region.

16. The diffractive multi-focal lens according to claim 15, wherein at least a portion of the diffractive structure has a synchronous structure for which, with $c_1$, $c_2$ and $c_3$ all being mutually different natural numbers, a $c_3$-number of zone pitches continuous in the third zone profile is the same as either a $c_1$-number of zone pitches continuous in the first zone profile or a $c_2$-number of zone pitches continuous in the second zone profile.

17. The diffractive multi-focal lens according to claim 15, wherein an addition power $P_3$ given by the third zone profile is determined by Equation 8, and with a greatest common divisor being z for three integers of (b×e), (a×e), and (b×d) expressed using d and e in Equation 8 and a and b in Equation 3, at least a portion of the diffractive structure has a synchronous structure for which a (b×e)/z-number of continuous zone pitches in the first zone profile, an (a×e)/z-number of continuous zone pitches in the second zone profile, and a (b×d)/z-number of continuous zone pitches in the third zone profile are mutually the same $$P_3 = \frac{d}{e} \times P_1 \qquad \text{[Equation 8]}$$

(d, e: Mutually different integers of zero or greater).

18. The diffractive multi-focal lens according to claim 15, wherein at least a portion of the third zone profile has a zone pitch given by Equation 6, and an addition power $P_3$ given by the third zone profile is different from both of the addition powers given by the first and second zone profiles $$r_q = \sqrt{r_1''^2 + \frac{2\lambda(q-1)}{P_3}} \qquad \text{[Equation 6]}$$

$\lambda$: Design wavelength
$r_q$: qth zone radius of the third zone profile
$r_1''$: First zone radius of the third zone profile
$P_3$: Addition power of the third zone profile
q: Natural number.

19. The diffractive multi-focal lens according to claim 18, wherein a first zone radius $r_1''$ of the third zone profile is expressed by Equation 7

$$r_1'' = \sqrt{\frac{2\lambda}{P_3}}. \qquad \text{[Equation 7]}$$

20. The diffractive multi-focal lens according to claim 15, wherein in addition to the first zone profile, the second zone profile, and the third zone profile, a fourth zone profile is also set, and the diffractive structure includes the first, second, third, and fourth zone profiles overlapped on the same region.

21. The diffractive multi-focal lens according to claim 20, wherein in addition to the first zone profile, the second zone profile, the third zone profile, and the fourth zone profile, a fifth zone profile is also set, and the diffractive structure includes the first, second, third, fourth, and fifth zone profiles overlapped on the same region.

22. The diffractive multi-focal lens according to claim 1, wherein the diffractive structure is formed with a diffractive structure characterized by a phase function to modulate a phase of a light.

23. The diffractive multi-focal lens according to claim 22, wherein the phase function comprises a blaze shaped function.

24. The diffractive multi-focal lens according to claim 23, wherein the blaze shaped phase function $\phi(r)$ is expressed by Equation 9

$$\phi(r) = \frac{\phi_i - \phi_{i-1}}{r_i - r_{i-1}} \times r + \frac{\phi_{i-1} \times r_i - \phi_i \times r_{i-1}}{r_i - r_{i-1}} + \tau \qquad \text{[Equation 9]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift.

25. A method for manufacturing a diffractive multi-focal lens having a diffractive structure comprising a plurality of zones in a concentric circle form, comprising
  forming an overlapping region for which a first zone profile and a second zone profile are overlapped on the same region in at least a portion of the diffractive structure, the first zone profile having a zone pitch expressed by Equation 10 in at least a portion thereof and the second zone profile having a zone pitch expressed by Equation 11 in at least a portion thereof, and an addition power $P_1$ given by the first zone profile and an addition power $P_2$ given by the second zone profile being determined by a relational expression of Equation 12, where a and b are mutually different integers of zero or greater, while being set so that quotients when a and b are divided by a mutual greatest common divisor thereof are both an integer other than 1, and a value of a/b is a value that cannot be expressed by a natural number X or by 1/X, and wherein the overlapping region is formed so that it generates at least three focal points $$r_n = \sqrt{r_1^2 + \frac{2\lambda(n-1)}{P_1}}$$ [Equation 10]

$\lambda$: Design wavelength
$r_n$: nth zone radius of the first zone profile
$r_1$: First zone radius of the first zone profile
$P_1$: Addition power of the first zone profile
n: Natural number $$r_m = \sqrt{r_1'^2 + \frac{2\lambda(m-1)}{P_2}}$$ [Equation 11]

$\lambda$: Design wavelength
$r_m$: mth zone radius of the second zone profile
$r_1'$: First zone radius of the second zone profile
$P_2$: Addition power of the second zone profile
m: Natural number $$P_2 = \frac{a}{b} \times P_1.$$ [Equation 12]

26. The method for manufacturing the diffractive multifocal lens according to claim 25, wherein a and b in Equation 12 are set to values that satisfy a relationship of a/b>1/2.

27. The method for manufacturing the diffractive multifocal lens according to claim 25, wherein by adjusting at least one of a phase constant and a phase shift for at least one of the first zone profile and the second zone profile that are overlapped with each other, an intensity distribution in an optical axis direction is adjusted and set.

28. The method for manufacturing the diffractive multifocal lens according to claim 27, wherein the at least one of the phase constant and the phase shift for the zone profile is adjusted to be mutually different between regions in a lens radial direction in the zone profile.

\* \* \* \* \*